US011408894B2

(12) United States Patent
Min et al.

(10) Patent No.: US 11,408,894 B2
(45) Date of Patent: Aug. 9, 2022

(54) DEVICES, COMPOSITIONS AND METHODS FOR IMAGING WITH RAMAN SCATTERING

(71) Applicant: THE TRUSTEES OF COLUMBIA UNIVERSITY IN THE CITY OF NEW YORK, New York, NY (US)

(72) Inventors: Wei Min, Edgewater, NJ (US); Lu Wei, Anhui (CN); Zhixing Chen, Beijing (CN); Fanghao Hu, New York, NY (US); Yihui Shen, Jiangsu (CN)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/717,634

(22) Filed: Dec. 17, 2019

(65) Prior Publication Data
US 2020/0200763 A1 Jun. 25, 2020

Related U.S. Application Data

(60) Division of application No. 14/974,992, filed on Dec. 18, 2015, which is a continuation-in-part of application No. PCT/US2014/042936, filed on Jun. 18, 2014.

(60) Provisional application No. 61/836,235, filed on Jun. 18, 2013.

(51) Int. Cl.
*G01N 33/58* (2006.01)
*A61K 49/00* (2006.01)
*G01N 21/65* (2006.01)
*G01N 33/50* (2006.01)

(52) U.S. Cl.
CPC ....... *G01N 33/583* (2013.01); *A61K 49/0013* (2013.01); *G01N 33/5005* (2013.01); *G01N 2021/655* (2013.01)

(58) Field of Classification Search
None
See application file for complete search history.

(56) References Cited

U.S. PATENT DOCUMENTS

| 4,693,993 | A | 9/1987 | Stewart et al. |
| 2004/0166118 | A1 | 8/2004 | Meloen et al. |
| 2006/0054506 | A1 | 3/2006 | Natan et al. |
| 2015/0192590 | A1 | 7/2015 | Sodeoka et al. |

OTHER PUBLICATIONS

Saar et al. Imaging drug delivery to skin with stimulated raman scattering microscopy. 2011 Mol. Pharm. 8: 969-975. (Year: 2011).*
Etchegoin et al. Evidence of natural isotopic distribution from single-molecule SERS. 2009 J. Am. Chem. Soc. 131:2713-2716. (Year: 2009).*
Fu et al., "Quantitative Chemical Imaging with Multiplex Stimulated Raman Scattering Microscopy," J Am Chem Soc. vol. 134, pp. 3623-3626 Feb. 29, 2012 [From Parent U.S. Appl. No. 14/974,992, filed Dec. 18, 2015].
Wei et al. "Vibrational Imaging of Newly Synthesized Proteins in Live Cells by Stimulated Raman Scattering Microscopy," PNAS, vol. 110, pp. 11226-11231 Jun. 24, 2013 [From Parent U.S. Appl. No. 14/974,992, filed Dec. 18, 2015].
Senlian Hong et al., "Live-Cell Stimulated Raman Scattering Imaging of Alkyne-Tagged Biomolecules," Angew. Chem. Int. Ed. vol. 53, pp. 5827-5831, 2014 [From Parent U.S. Appl. No. 14/974,992, filed Dec. 18, 2015].
Zhixing Chen et al., "Multicolor Live-Cell Chemical Imaging by Isotopically Edited Alkyne Vibrational Palette," J. Am. Chem. Soc., vol. 136, gs. 8027-8033, 2014 [From Parent U.S. Appl. No. 14/974,992, filed Dec. 18, 2015].
Lu Wei et al., "Live-Cell Bioorthogonal Chemical Imaging: Stimulated Raman Scattering Microscopy of Vibrational Probes," Acc. Chem. Res., vol. 49, pp. 1494-1502, 2016 [From Parent U.S. Appl. No. 14/974,992, filed Dec. 18, 2015].
International Search Report and Written Opinion dated Jun. 4, 2019 for International Application No. PCT/US2019/023358 [From Parent U.S. Appl. No. 14/974,992, filed Dec. 18, 2015].
Hershey, John W.B. et al., "Principles of Translational Control: An Overview," Cold Spring Harbor Perspect Biol, vol. 4, pp. 1-11, 2012 [From Parent U.S. Appl. No. 14/974,992, filed Dec. 18, 2015].
Resch-Genger U, et al (2008) Quantum dots versus organic dyes as fluorescent labels. Nature methods 5:763-775. [From Parent U.S. Appl. No. 14/974,992, filed Dec. 18, 2015].
Knoll B, Keilmann F (1999) Near-field probing of vibrational absorption for chemical microscopy. Nature 399:7-10. [From Parent U.S. Appl. No. 14/974,992, filed Dec. 18, 2015].
Lim Rk V, Lin Q (2010) Bioorthogonal chemistry: recent progress and future directions. Chemical communications (Cambridge, England) 46:1589-600. [From Parent U.S. Appl. No. 14/974,992, filed Dec. 18, 2015].
Yamakoshi H et al. (2011) Imaging of EdU, an alkyne-tagged cell proliferation probe, by Raman microscopy. Journal of the American Chemical Society 133:6102-5. [From Parent U.S. Appl. No. 14/974,992, filed Dec. 18, 2015].

(Continued)

*Primary Examiner* — Jennifer Lamberski
(74) *Attorney, Agent, or Firm* — Hunton Andrews Kurth LLP

(57) ABSTRACT

Methods, systems and computer-accessible medium for imaging a living cell or a living organism with bond-edited compounds using stimulated Raman scattering are disclosed. The method comprises the steps of introducing one or more bond-edited compounds into a live cell or a living organism, and detecting a vibrational tag in the cell or organism with stimulated Raman scattering. Also disclosed are methods for detecting a disease condition in a subject, methods for monitoring treatment for a disease condition, methods for screening an agent, methods for tracing a cellular process in a live cell using bond-edited compounds in combination with stimulated Raman scattering. Also disclosed are a composition for labeling a target cell with at least one bond-edited compound and devices for imaging bond-edited compounds by stimulated Raman scattering.

13 Claims, 38 Drawing Sheets

(56) References Cited

OTHER PUBLICATIONS

Yamakoshi H et al. (2012) Alkyne-tag Raman imaging for visualization of mobile small molecules in live cells. Journal of the American Chemical Society 134:20681-9. [From Parent U.S. Appl. No. 14/974,992, filed Dec. 18, 2015].
Bloembergen N (1967) The Stimulated Raman Effect. American Journal of Physics 35:989-1023. [From Parent U.S. Appl. No. 14/974,992, filed Dec. 18, 2015].
Martin KC, et al. (2000) Local protein synthesis and its role in synapse-specific plasticity, Curr. Opin. Neurobiol. 10:587-592. [From Parent U.S. Appl. No. 14/974,992, filed Dec. 18, 2015].
Schoenheimer R et al.(1938) Application of isotopes to the study of intermediary metabolism. Science 87:221-226. [From Parent U.S. Appl. No. 14/974,992, filed Dec. 18, 2015].
Mann M (2006) Functional and quantitative proteomics using SILAC. Nat. Rev. Mol. Cell. Biol. 7:952-958. [From Parent U.S. Appl. No. 14/974,992, filed Dec. 18, 2015].
Harsha HC et al.(2008) Quantitative proteomics using stable isotope labeling with amino acids in cell culture. Nat. Protoc. 3:505-516. [From Parent U.S. Appl. No. 14/974,992, filed Dec. 18, 2015].
Evans CL et al.(2008) Coherent anti-Stokes Raman scattering microscopy: chemical imaging for biology and medicine. Annu. Rev. Anal. Chem. 1:883-909. [From Parent U.S. Appl. No. 14/974,992, filed Dec. 18, 2015].
Pezacki JP et al. (2011) Chemical contrast for imaging living systems: molecular vibrations drive CARS microscopy. Nat. Chem. Biol. 7:137-145. [From Parent U.S. Appl. No. 14/974,992, filed Dec. 18, 2015].
Ploetz E et al. (2007) Femtosecond stimulated Raman microscopy. Appl. Phys. B 87:389-393. [From Parent U.S. Appl. No. 14/974,992, filed Dec. 18, 2015].
Okayasu T et al. (1997) The amino acid composition of mammalian and bacterial cells. Amino Acids 13:379-391. [From Parent U.S. Appl. No. 14/974,992, filed Dec. 18, 2015].
Phair RD et al. (2000) High mobility of proteins in the mammalian cell nucleus. Nature 404: 604-609. [From Parent U.S. Appl. No. 14/974,992, filed Dec. 18, 2015].
Andersen JS et al. (2005) Nucleolar proteome dynamics. Nature 433:77-83. [From Parent U.S. Appl. No. 14/974,992, filed Dec. 18, 2015].
Van Manen HJ et al. (2008) Noninvasive imaging of protein metabolic labeling in single human cells using stable isotopes and Raman microscopy. Anal. chem. 80:9 [From Parent U.S. Appl. No. 14/974,992, filed Dec. 18, 2015].
Cui et al. (2009) Comparing coherent and spontaneous Raman scattering under biological imaging conditions. Opt. Lett. 34(16): 773-775. [From Parent U.S. Appl. No. 14/974,992, filed Dec. 18, 2015].
Yuste, R. Fluorescence microscopy today. Nat. Methods 2, 902-904 (2005). [From Parent U.S. Appl. No. 14/974,992, filed Dec. 18, 2015].
Myers, A B. Molecular electronic spectral broadening in liquids and glasses. Annu. Rev. Phys. Chem. 49, 267-295 (1998). [From Parent U.S. Appl. No. 14/974,992, filed Dec. 18, 2015].
Nemkovich, N., et al. "Inhomogeneous Broadening of Electronic Spectra of Dye Molecules in Solutions". Top. Fluoresc. Spectrosc. SE—8 2, 367-428 (2002). [From Parent U.S. Appl. No. 14/974,992, filed Dec. 18, 2015].
Results, E. Probe-frequency dependence of the resonant Inverse Raman band shape. Oct. 89, 3945-3950 (1988). [From Parent U.S. Appl. No. 14/974,992, filed Dec. 18, 2015].
Suhalim JL, et al. (2012) The need for speed. J. Biophotonics 5:387-95. [From Parent U.S. Appl. No. 14/974,992, filed Dec. 18, 2015].
Ozeki Y, et al. (2009) Analysis and experimental assessment of the sensitivity of stimulated Raman scattering microscopy. Opt. express. 17:3651-3658. [From Parent U.S. Appl. No. 14/974,992, filed Dec. 18, 2015].
Nandakumar P, et al. (2009) Vibrational imaging based on stimulated Raman scattering microscopy. New J. Phys. 11:033026. [From Parent U.S. Appl. No. 14/974,992, filed Dec. 18, 2015].
Zhang D, et al (2011) Highly sensitive vibrational imaging by femtosecond pulse Stimulated raman Loss. J. Phys. Chem. Lett. 2:1248-1253 [From Parent U.S. Appl. No. 14/974,992, filed Dec. 18, 2015].
Wang MC, et al. (2011) RNAi screening for fat regulatory genes with SRS microscopy. Nat. methods 8:135-138. [From Parent U.S. Appl. No. 14/974,992, filed Dec. 18, 2015].
Zhang X et al. (2012) Label-free live-cell imaging of nucleic acids using stimulated Raman scattering microscopy. Chemphyschem. 13:1054-1059. [From Parent U.S. Appl. No. 14/974,992, filed Dec. 18, 2015].
Fu D et al. (2012) Quantitative chemical imaging with multiplex stimulated Raman scattering microscopy. J. Am. Chem. Soc. 134: 3623-3626 [From Parent U.S. Appl. No. 14/974,992, filed Dec. 18, 2015].
Ozeki Y et al. (2012) High-speed molecular spectral imaging of tissue with stimulated Raman scattering. Nature Photon. 6:845-851 [From Parent U.S. Appl. No. 14/974,992, filed Dec. 18, 2015].
Einstein A (1917) On the quantum theory of radiation. Phys. Z. 18:121-128. [From Parent U.S. Appl. No. 14/974,992, filed Dec. 18, 2015].
Min W (2011) Label-free optical imaging of nonfluorescent molecules by stimulated radiation. Curr. Opin. Chem. Biol. 15:831-837. [From Parent U.S. Appl. No. 14/974,992, filed Dec. 18, 2015].
Boisvert FM et al. (2012) A quantitative spatial proteomics analysis of proteome turnover in human cells. Mol. Cell. Proteomics. 11(3) [From Parent U.S. Appl. No. 14/974,992, filed Dec. 18, 2015].
Piez KA and Eagle H (1957) The free amino acid pool of cultured human cells. J. Biol. Chem. 231: 533-545 [From Parent U.S. Appl. No. 14/974,992, filed Dec. 18, 2015].
Lechene CP, et al. (2007) Quantitative imaging of nitrogen fixation by individual bacteria within animal cells. Science 317:1563-1566 [From Parent U.S. Appl. No. 14/974,992, filed Dec. 18, 2015].
Zhang DS et al. (2012) Multi-isotope imaging mass spectrometry reveals slow protein turnover in hair-cell stereocilia. Nature 481:520-524. [From Parent U.S. Appl. No. 14/974,992, filed Dec. 18, 2015].
Ji Minbiao et al. (2013) Rapid, label-free detection of brain tumors with stimulated Raman scattering miscroscopy. Sci. Transl. Med. 5(201) [From Parent U.S. Appl. No. 14/974,992, filed Dec. 18, 2015].
Saar et al. (2011) Imaging drug delivery to skin with stimulated Raman scattering microscopy. Mol. Pharm. 8(3):969-75. [From Parent U.S. Appl. No. 14/974,992, filed Dec. 18, 2015].
Petrov et al. (2007) Comparision of coherent and spontaneous Raman microspectroscopies for noninvasive detection of single bacterial endospores. Proc. Natl. Acad. Sci. U [From Parent U.S. Appl. No. 14/974,992, filed Dec. 18, 2015].
Asher, S. A. UV resonance Raman studies of molecular structure and dynamics: applications in physical and biophysical chemistry. Annu. Rev. Phys. Chem. 39, 537-588 (1988) [From Parent U.S. Appl. No. 14/974,992, filed Dec. 18, 2015].
Nie, S., et al. Probing individual molecules with confocal fluorescence microscopy. Science 266, 1018-1021 (1994). [From Parent U.S. Appl. No. 14/974,992, filed Dec. 18, 2015].
Moerner, et al. Illuminating single molecules in condensed matter. Science 283, 1670-1676 (1999). [From Parent U.S. Appl. No. 14/974,992, filed Dec. 18, 2015].
Denk, W., et al. Two-photon laser scanning fluorescence microscopy. Science 248, 73-76 (1990). [From Parent U.S. Appl. No. 14/974,992, filed Dec. 18, 2015].
Hell, S. W. et al. Breaking the diffraction resolution limit by stimulated emission: stimulated-emission-depletion fluorescence microscopy. Opt. Lett. 19, 780-2 (1994). [From Parent U.S. Appl. No. 14/974,992, filed Dec. 18, 2015].
Betzig, E. et al. Imaging intracellular fluorescent proteins at nanometer resolution. Science 313, 1642-1645 (2006). [From Parent U.S. Appl. No. 14/974,992, filed Dec. 18, 2015].

(56) References Cited

OTHER PUBLICATIONS

Rust, M. et al. Sub-diffraction-limit imaging by stochastic optical reconstruction microscopy (STORM). Nat. Methods 3, 793-795 (2006). [From Parent U.S. Appl. No. 14/974,992, filed Dec. 18, 2015].
Ha, T. et al. Probing the interaction between two single molecules: fluorescence resonance energy transfer between a single donor & a single acceptor. PNAS 93, 6264-68 (1996) [From Parent U.S. Appl. No. 14/974,992, filed Dec. 18, 2015].
Gaiduk, A., et al. Room-temperature detection of a single molecule's absorption by photothermal contrast. Science 330, 353-356 (2010). [From Parent U.S. Appl. No. 14/974,992, filed Dec. 18, 2015].
Chong, S., et al. Ground-state depletion microscopy: Detection sensitivity of single-molecule optical absorption at room temperature. J. Phys. Chem. Lett. 1, 3316-3322 (2010) [From Parent U.S. Appl. No. 14/974,992, filed Dec. 18, 2015].
Kukura, P., et al. Single-molecule sensitivity in optical absorption at room temperature. J. Phys. Chem. Lett. 1, 3323-3327 (2010). [From Parent U.S. Appl. No. 14/974,992, filed Dec. 18, 2015].
Giesen, C. et al. Highly multiplexed imaging of tumor tissues with subcellular resolution by mass cytometry. Nat. Methods 11, 417-22 (2014). [From Parent U.S. Appl. No. 14/974,992, filed Dec. 18, 2015].
Angelo, M. et al. Multiplexed ion beam imaging of human breast tumors. Nat. Med. 20, 436-42 (2014). [From Parent U.S. Appl. No. 14/974,992, filed Dec. 18, 2015].
Barlogie, B. et al. Flow Cytometry in Clinical Cancer Research Flow Cytometry in Clinical Cancer Research1. 43, 3982-3997 (1983). [From Parent U.S. Appl. No. 14/974,992, filed Dec. 18, 2015].
Geiger, B. et al. Environmental sensing through focal adhesions. Nat. Rev. Mol. Cell Biol. 10, 21-33 (2009). [From Parent U.S. Appl. No. 14/974,992, filed Dec. 18, 2015].
Nie, S. Probing Single Molecules and Single Nanoparticles by Surface-Enhanced Raman Scattering. Science. 275, 1102-1106 (1997). [From Parent U.S. Appl. No. 14/974,992, filed Dec. 18, 2015].
Kneipp, K. et al. Single molecule detection using surface-enhanced Raman scattering (SERS). Phys. Rev. Lett. 78, 1667-1670 (1997). [From Parent U.S. Appl. No. 14/974,992, filed Dec. 18, 2015].
Freudiger, C. et al. Label-free biomedical imaging with high sensitivity by stimulated Raman scattering microscopy. Science (80-. ). 322, 1857-1861 (2008). [From Parent U.S. Appl. No. 14/974,992, filed Dec. 18, 2015].
Wei, L. et al. Live-cell imaging of alkyne-tagged small biomolecules by stimulated Raman scattering. Nat. Methods 11, 410-2 (2014). [From Parent U.S. Appl. No. 14/974,992, filed Dec. 18, 2015].
Yamakoshi, H. et al. Alkyne-tag Raman imaging for visualization of mobile small molecules in live cells. J. Am. Chem. Soc. 134, 20681-20689 (2012) [From Parent U.S. Appl. No. 14/974,992, filed Dec. 18, 2015].
McCamant, et al. Femtosecond Broadband Stimulated Raman: A New Approach for High-Performance Vibrational Spectroscopy. Appl. Spectrosc. 57, 1317-1323 (2003) [From Parent U.S. Appl. No. 14/974,992, filed Dec. 18, 2015].
Kim, H. M., et al. Time-gated pre-resonant femtosecond stimulated Raman spectroscopy of diethylthiatricarbocyanine iodide. Phys. Chem. Chem. Phys. 16, 5312-8 (2014). [From Parent U.S. Appl. No. 14/974,992, filed Dec. 18, 2015].
Chalfie M. et al., (1994) Green fluorescent protein as a marker gene expression. Science 263:802-804 [From Parent U.S. Appl. No. 14/974,992, filed Dec. 18, 2015].
Tsien R. Y., (1998) The Green Fluorescent. Annu. Rev. Biochemistry 67:509-544. [From Parent U.S. Appl. No. 14/974,992, filed Dec. 18, 2015].
Miyawaki A. et al., (2003) Lighting up cells: labelling proteins with fluorophores. Nature cell biology :S1-S7 [From Parent U.S. Appl. No. 14/974,992, filed Dec. 18, 2015].
Evans C. L. and Xie XS (2008) Coherent anti-stokes Raman scattering microscopy: chemical imaging for biology and medicine. Annual review of analytical chemistry 1:883-909 [From Parent U.S. Appl. No. 14/974,992, filed Dec. 18, 2015].
Freudiger C. et al., (2008) Label-free biomedical imaging with high sensitivity by stimulated Raman scattering microscopy. Science 322:1857-1861 [From Parent U.S. Appl. No. 14/974,992, filed Dec. 18, 2015].
Min W. et al., (2011) Coherent nonlinear optical imaging: beyond fluorescence microscopy. Annual review of physical chemistry 62:507-30 [From Parent U.S. Appl. No. 14/974,992, filed Dec. 18, 2015].
Prescher J. A. and Bertozzi C. R. (2005) Chemistry in living systems. Nature chemical biology 1:13-21 [From Parent U.S. Appl. No. 14/974,992, filed Dec. 18, 2015].
Sletten E. M. and Bertozzi C. R. (2009) Bioorthogonal chemistry: fishing for selectivity in a sea of functionality. Angewandte Chemie (Int'l ed. in English) 48:6974-6998 [From Parent U.S. Appl. No. 14/974,992, filed Dec. 18, 2015].
Saar B. G. et al., (2010) Video-rate molecular imaging in vivo with stimulated Raman scattering. Science 330:1368-1370. [From Parent U.S. Appl. No. 14/974,992, filed Dec. 18, 2015].
Salic A. and Mitchison T. J. (2008) A chemical method for fast and sensitive detection of DNA synthesis in vivo. PNAS, 105:2415-2420 [From Parent U.S. Appl. No. 14/974,992, filed Dec. 18, 2015].
Neef A.B and Luedtke N. W. (2011) Dynamic metabolic labeling of DNA in vivo with arabinosyl nucleosides. PNAS, 108:20404-9 [From Parent U.S. Appl. No. 14/974,992, filed Dec. 18, 2015].
Jao CY and Salic A (2008) Exploring RNA transcription and turnover in vivo by using click chemistry. PNAS, 105:15779-84 [From Parent U.S. Appl. No. 14/974,992, filed Dec. 18, 2015].
Beatty K. E. et al., (2006) Fluorescence visualization of newly synthesized proteins in mammalian cells, Angewandte Chemie (Int'l ed. in English) 45:7364-7 [From Parent U.S. Appl. No. 14/974,992, filed Dec. 18, 2015].
Liu J., et al., (2012) Imaging protein synthesis in cells and tissues with an alkyne analog of puromycin. PNAS, 109:413-8 [From Parent U.S. Appl. No. 14/974,992, filed Dec. 18, 2015].
Jao C.Y. et al., (2009) Metabolic labeling and direct imaging of choline phospholipids in vivo 106:15332-7 [From Parent U.S. Appl. No. 14/974,992, filed Dec. 18, 2015].
Kandel E. R. (2001) The molecular biology of memory storage: a dialogue between genes and synapses. Science 294:1030-1038 [From Parent U.S. Appl. No. 14/974,992, filed Dec. 18, 2015].
Dieterich DC, et al. (2006) Selective identification of newly . . . mammalian cells using bioorthogonal noncanonical amino acid tagging (BONCAT). Proc. Nat. Acad. Sci. 103:9482-9487 [From Parent U.S. Appl. No. 14/974,992, filed Dec. 18, 2015].
Beatty K. E. and Tirrell D. A. (2008) Two-color labeling of temporally defined proteinpopulations in mammalian cells. Bioorg. Med. Chem. Lett. 18:5995-5999 [From Parent U.S. Appl. No. 14/974,992, filed Dec. 18, 2015].
Roche F.K. et al., (2009) Protein synthesis in distal axons is notrequired for growth cone responses to guidance cues. J Neurosci. 29:638-652 [From Parent U.S. Appl. No. 14/974,992, filed Dec. 18, 2015].
Dieterich D.C. et al., (2010) In situ visualization and dynamics of newly synthesizedproteins in rat hippocampal neurons. Nat. Neurosci. 13:897-905 [From Parent U.S. Appl. No. 14/974,992, filed Dec. 18, 2015].
Tcherkezian J. et al., (2010) Transmembrane receptor DCC associates with protein synthesis machinery and regulates translation. Cell 141:632-644 [From Parent U.S. Appl. No. 14/974,992, filed Dec. 18, 2015].
Hinz F. I. et al. (2012) Non-canonical amino acid labeling in vivo to visualize and affinity purify newly synthesized proteins in larval zebrafish. ACS Chem. Neurosci. 3:40-49 [From Parent U.S. Appl. No. 14/974,992, filed Dec. 18, 2015].
Boyce M. and Bertozzi C.R. (2011) Bringing chemistry to life. Nat. Methods 8:638-642 [From Parent U.S. Appl. No. 14/974,992, filed Dec. 18, 2015].
Schoenheimer R, Rittenberg D (1936) Deuterium as an indicator in the study of intermediary metabolism. J. Biol. Chem. 111:163-168 [From Parent U.S. Appl. No. 14/974,992, filed Dec. 18, 2015].

(56) References Cited

OTHER PUBLICATIONS

Ho V.M. et al. (2011) The cell biology of synaptic plasticity. Science 334:623-628 [From Parent U.S. Appl. No. 14/974,992, filed Dec. 18, 2015].

Ong SE et al. (2002) Stable isotope labeling by amino acids in cell culture, SILAC, as a simple & accurate approach to expression proteomics. Mol. Cell. Proteomics 1:376-386 [From Parent U.S. Appl. No. 14/974,992, filed Dec. 18, 2015].

Geiger T. et al., (2011) Use of stable isotope labeling by amino acids in cell culture as a spike-in standard in quantitative proteomics. Nat. Protoc. 6:147-157 [From Parent U.S. Appl. No. 14/974,992, filed Dec. 18, 2015].

Ingolia N.T. et al., (2011) Ribosome profiling of mouse embryonic stem cells reveals the complexity and dynamics of mammalian proteomes. Cell. 147:789-802 [From Parent U.S. Appl. No. 14/974,992, filed Dec. 18, 2015].

Zumbusch A. et al., (1999) Three-dimensional vibrational imaging by coherent anti-Stokes Raman scattering. Phys. Rev. Lett. 82:4142-4145 [From Parent U.S. Appl. No. 14/974,992, filed Dec. 18, 2015].

Cheng J.X. and Xie X.S. (2004) Coherent anti-Stokes Raman scattering microscopy: instrumentation, theory, and applications. J. Phys. Chem. B 108:827-840 [From Parent U.S. Appl. No. 14/974,992, filed Dec. 18, 2015].

International Search Report for International Application No. PCT/US2014/042936 dated Nov. 27, 2015 [From Parent U.S. Appl. No. 14/974,992, filed Dec. 18, 2015].

International Written Opinion for International Application No. PCT/US2014/042936 dated Nov. 27, 2015 [From Parent U.S. Appl. No. 14/974,992, filed Dec. 18, 2015].

Saar et al. "Video-Rate Molecular Imaging in Vivo with Stimulated Raman Scattering," Science, vol. 330, pp. 1368-1370 Dec. 3, 2010 [From Parent U.S. Appl. No. 14/974,992, filed Dec. 18, 2015].

Huang et al., "A Noncoding, Regulatory Mutation Implicates HCFC1 in Nonsyndromic Intellectual Disability," Am J. Hum Genet. vol. 91, pp. 694-702 Oct. 5, 2012 [From Parent U.S. Appl. No. 14/974,992, filed Dec. 18, 2015].

Palonpon et al. Molecular imaging of live cells by Raman microscopy. 2013 Curr. Opin. Chem. Biol. 17: 708-715. Epub Jun. 15, 2013. (Year: 2013).

Fu et al. In vivo metabolic fingerprinting of neutral lipids with hyperspectral stimulated Raman scattering microscopy. 2014 J. Am. Chem. Soc. 136: 8820-8828. Epub Jun. 9, 2014. (Year: 2014).

Notice of Allowance dated Apr. 1, 2022 for U.S. Appl. No. 14/974,992.

* cited by examiner

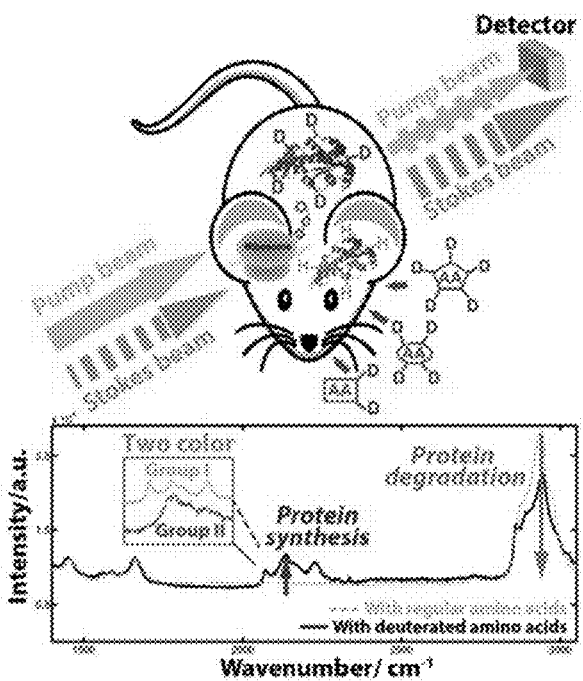
FIG. 1A
FIG. 1B
FIG. 1
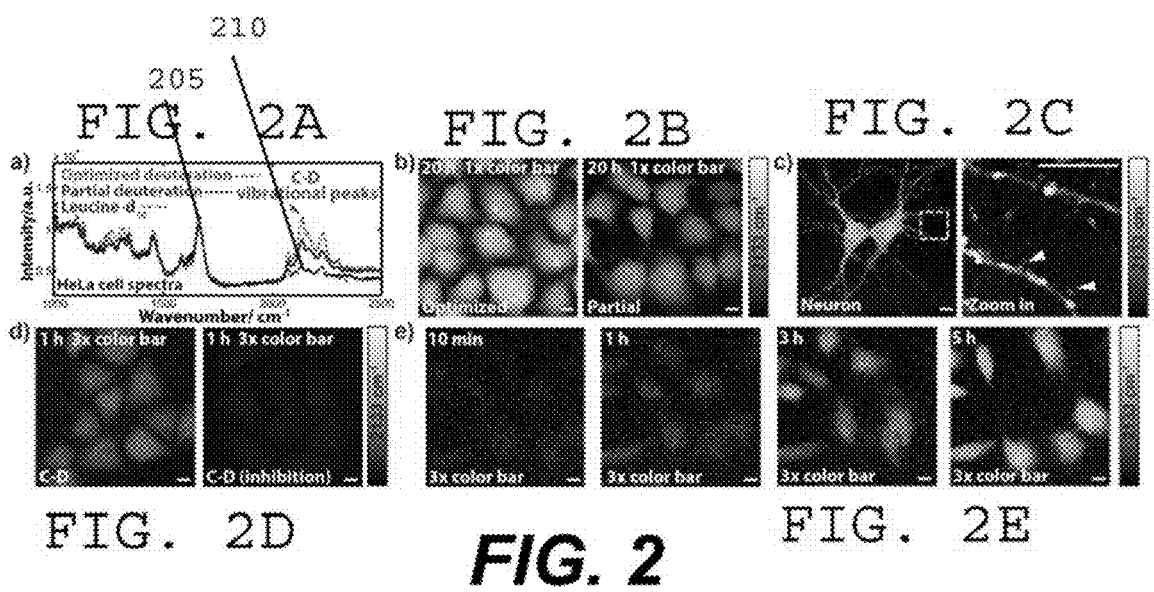
FIG. 2A  FIG. 2B  FIG. 2C
FIG. 2D  FIG. 2E
FIG. 2

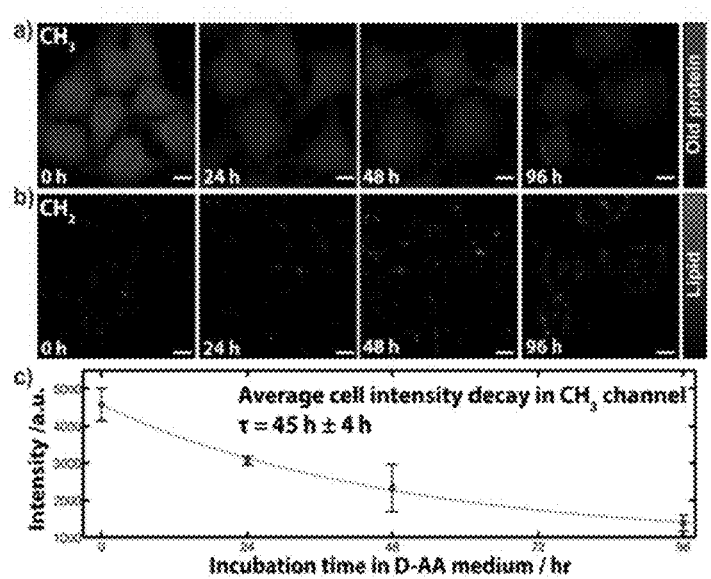
FIG. 3
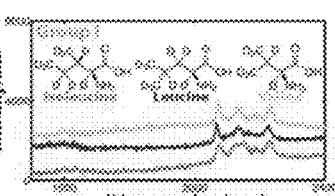 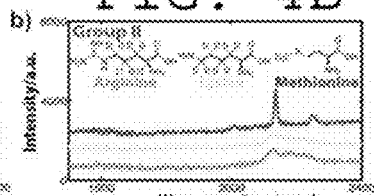
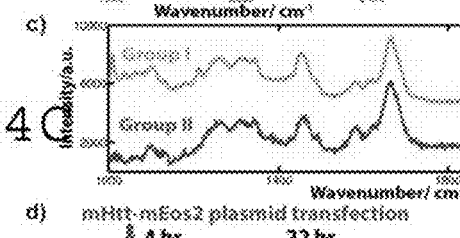
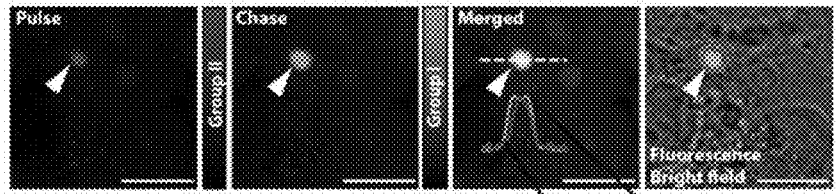
FIG. 4

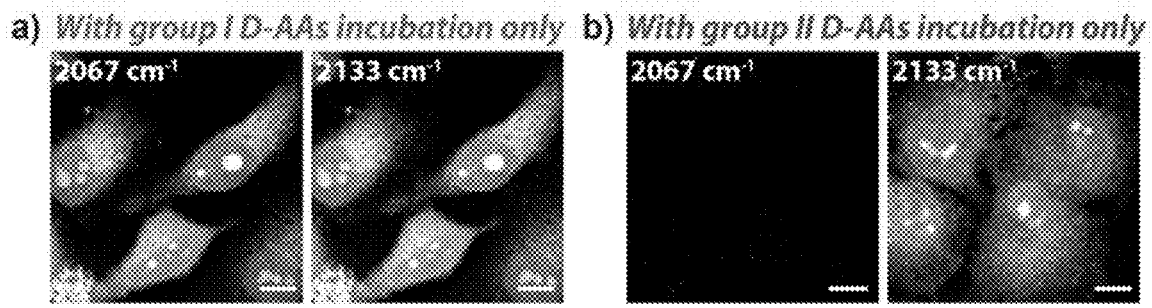
FIG. 7A     FIG. 7     FIG. 7B
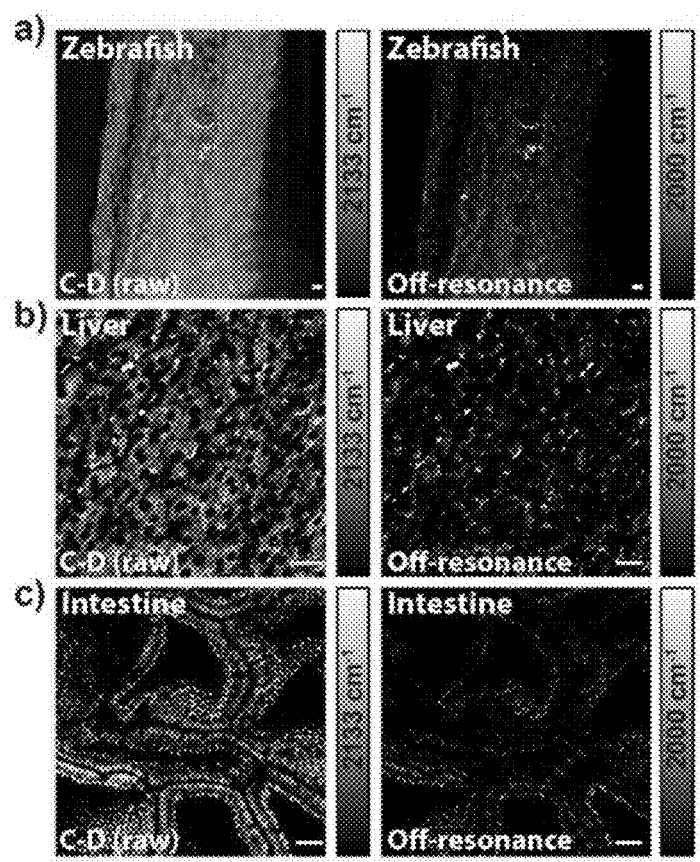
FIG. 8A
FIG. 8B
FIG. 8C
FIG. 8

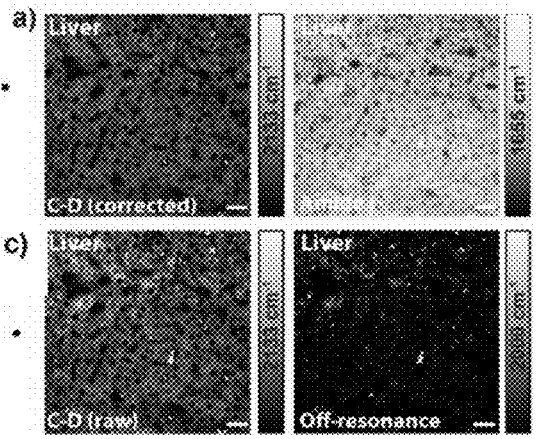
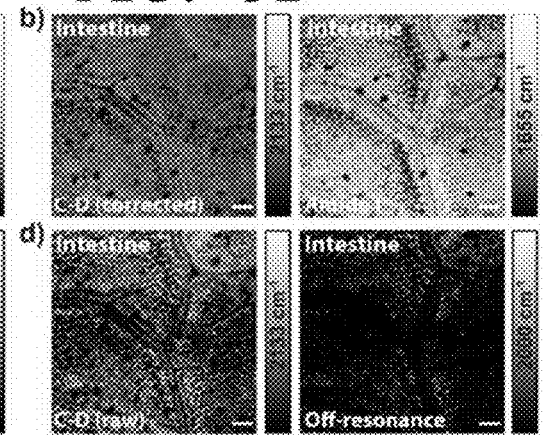
FIG. 9
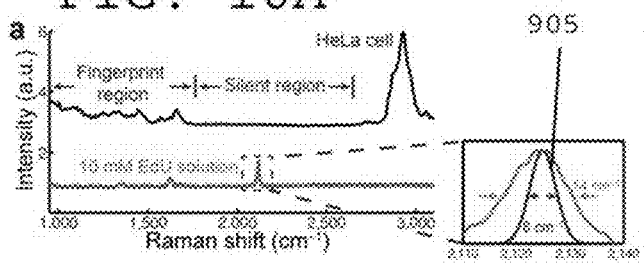
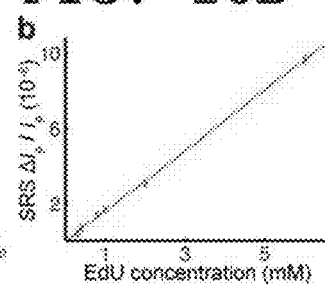
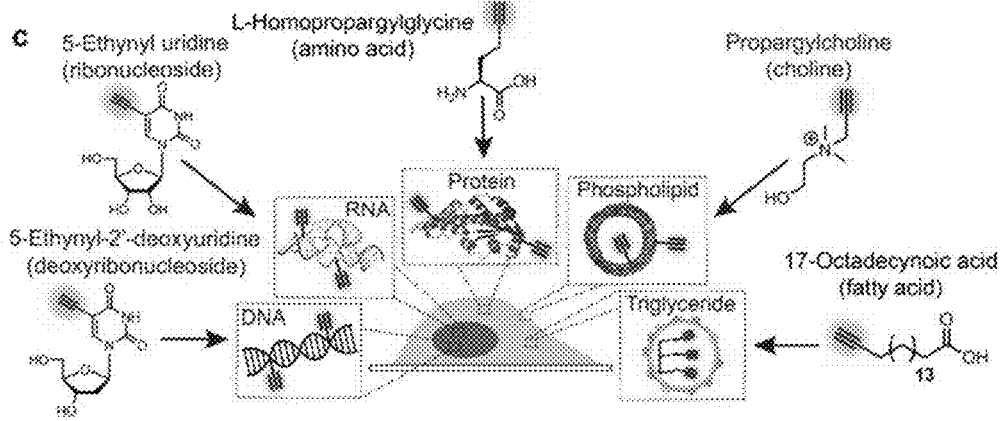
FIG. 10

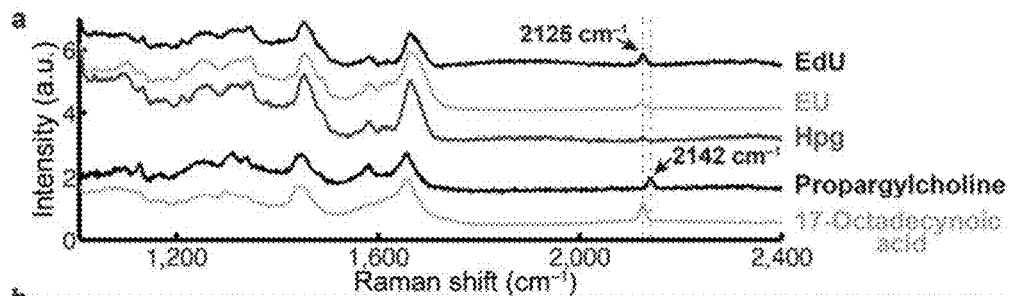
FIG. 12A
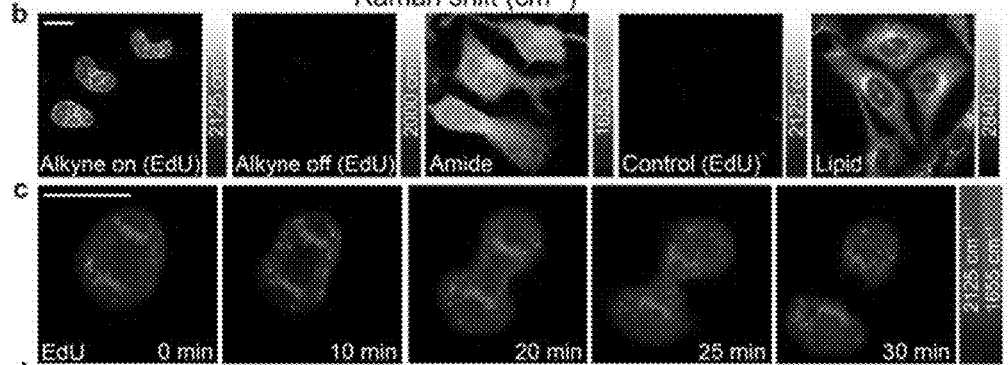
FIG. 12B
FIG. 12C
FIG. 12D
FIG. 12E
FIG. 12F
FIG. 12G  FIG. 12H  FIG. 12  FIG. 12I  FIG. 12J

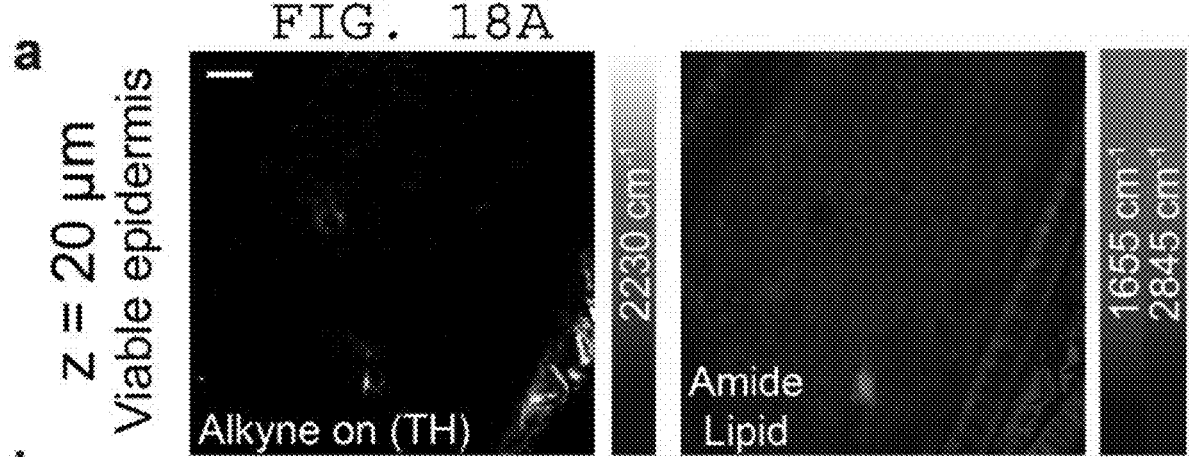
FIG. 18A
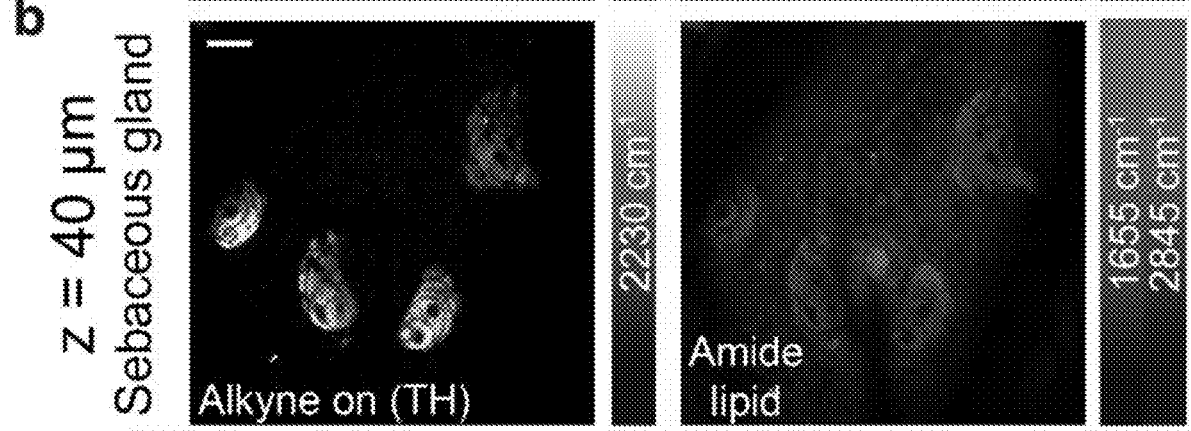
FIG. 18B
FIG. 18

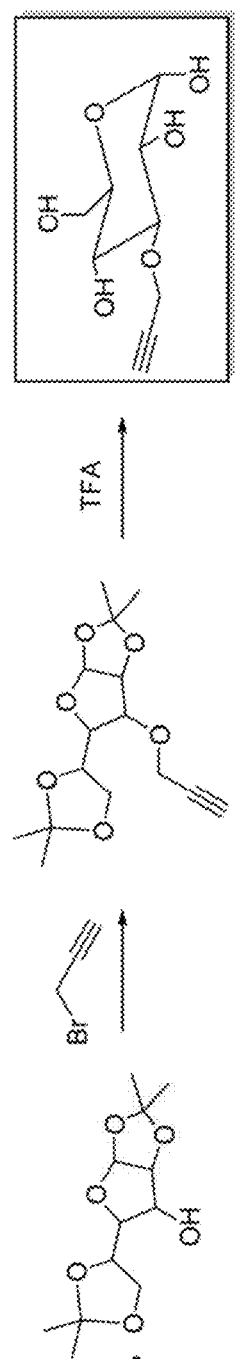
FIG. 20A
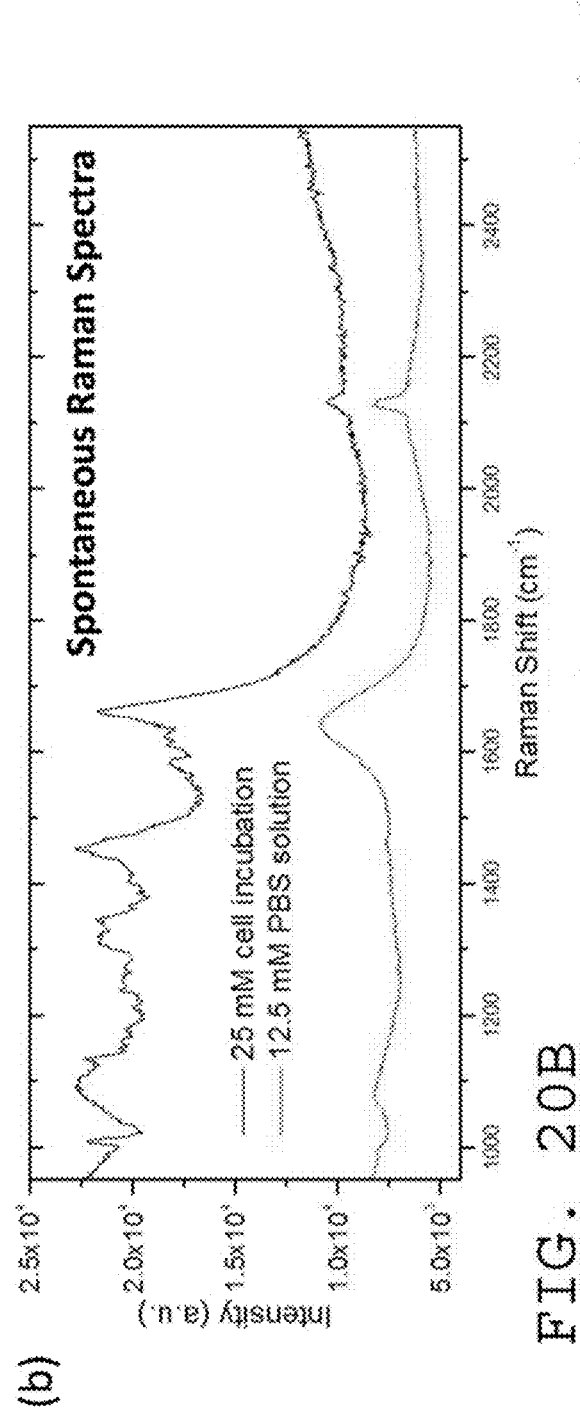
FIG. 20B
FIG. 20

Time-dependent alkyne-glucose (32 mM) uptake in live HeLa cells for 10min, 30 min, 1h, 2h, 3h and 4h time point. The glucose signal inside mammalian cells is increasing over time

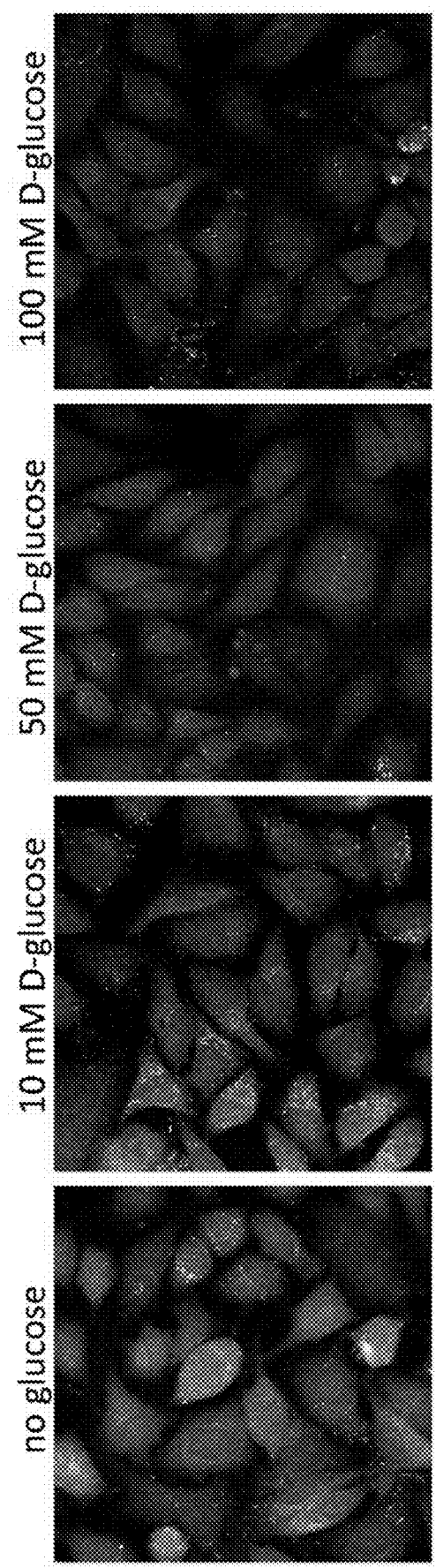
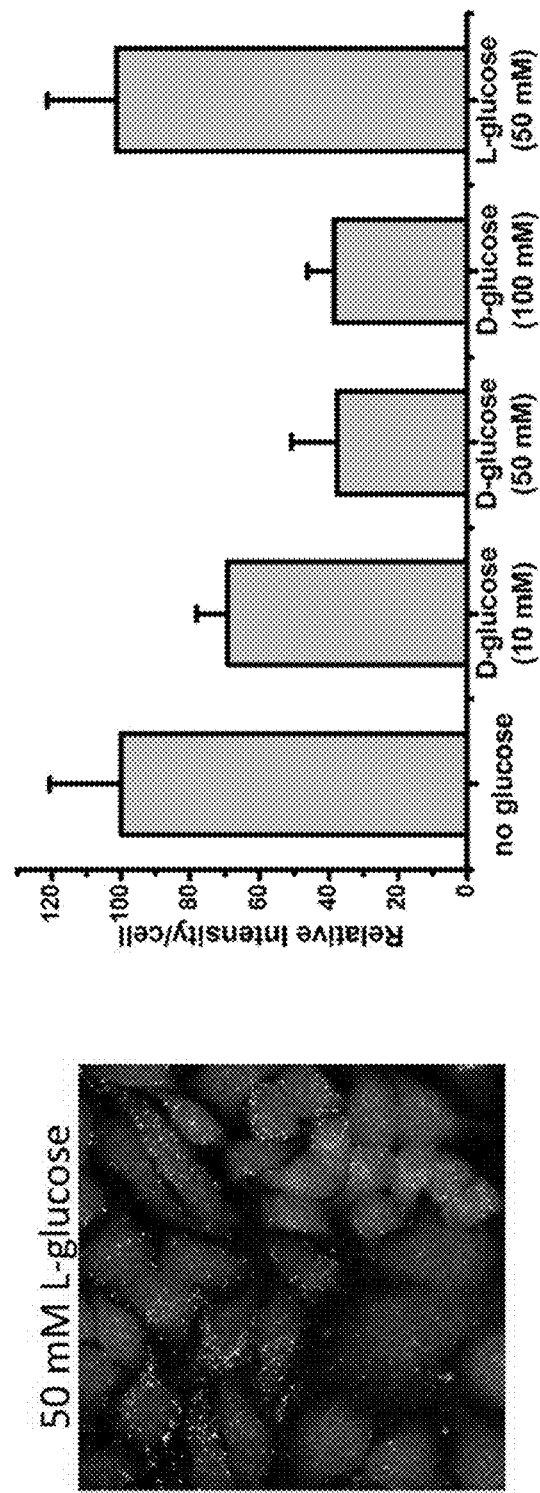
FIG. 22

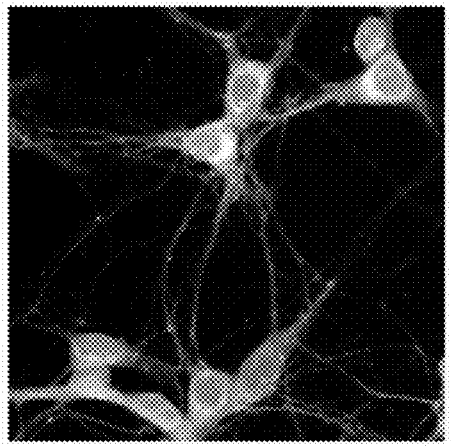
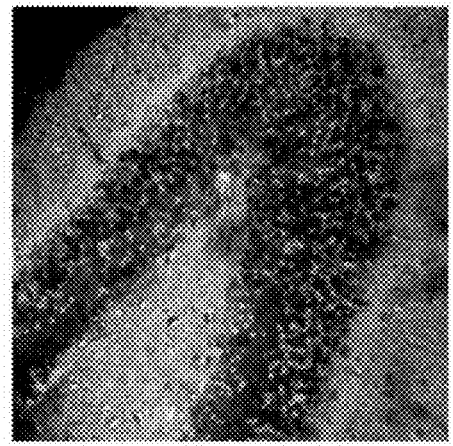
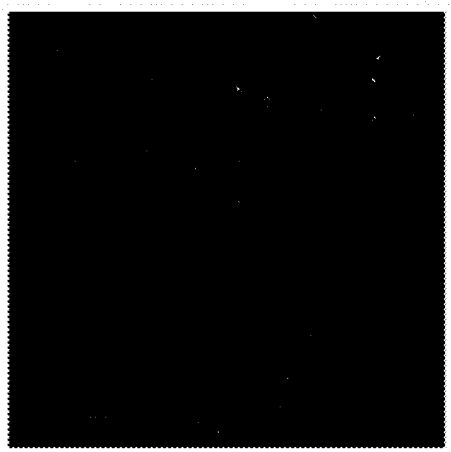
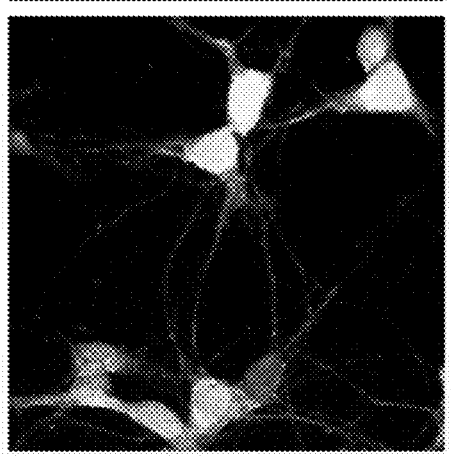
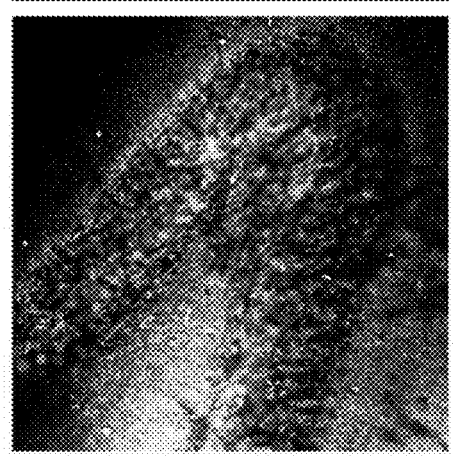
FIG. 23A
FIG. 23B
FIG. 23

Multicolor imaging of DNA synthesis (EdU (1); EdU-$^{13}$C (2) and EdU-$^{13}$C$_2$ (3)).

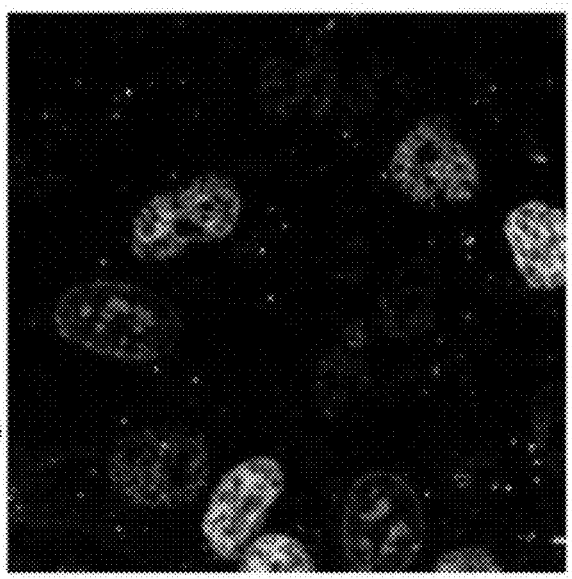
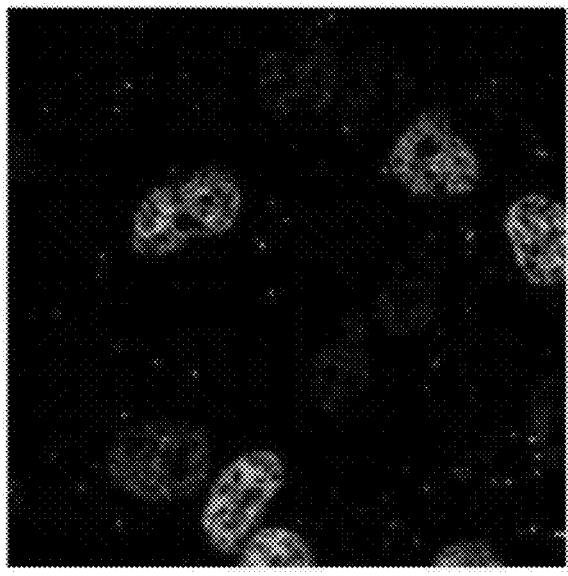
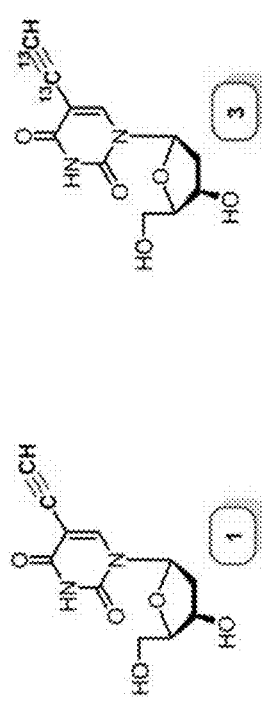
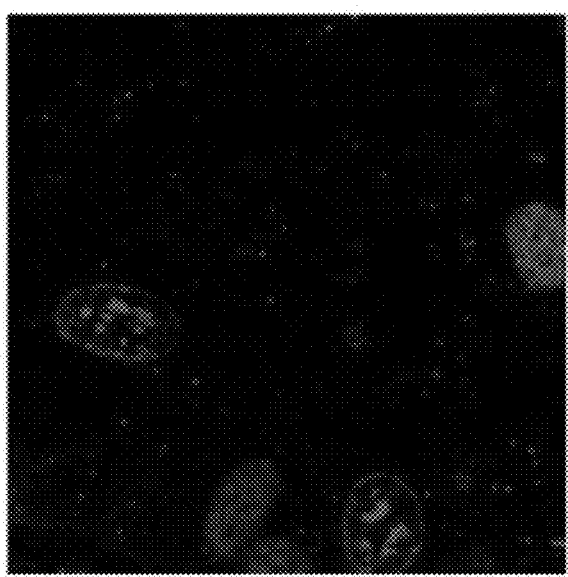
FIG. 25

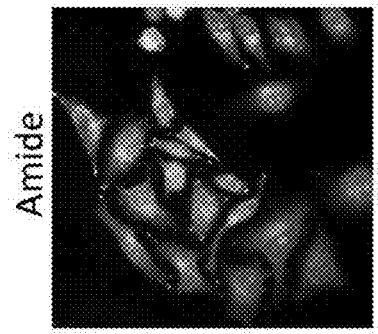
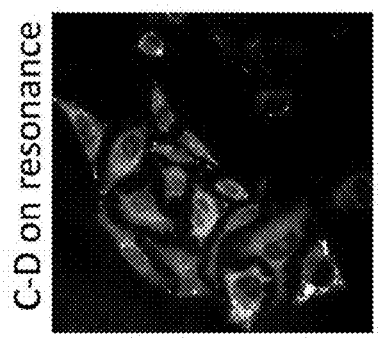
FIG. 28A
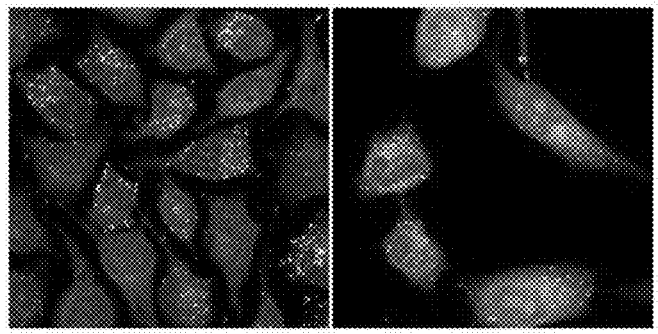
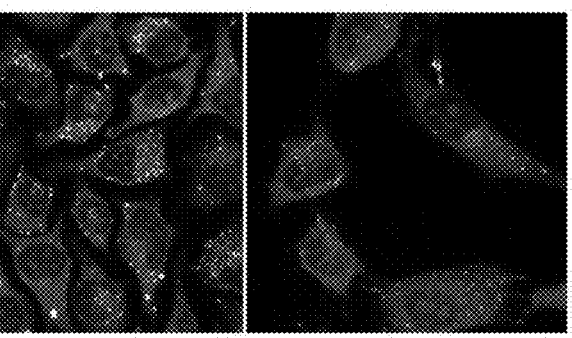
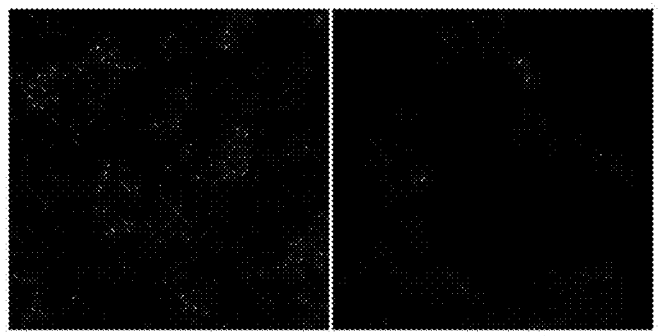
FIG. 28B
FIG. 28

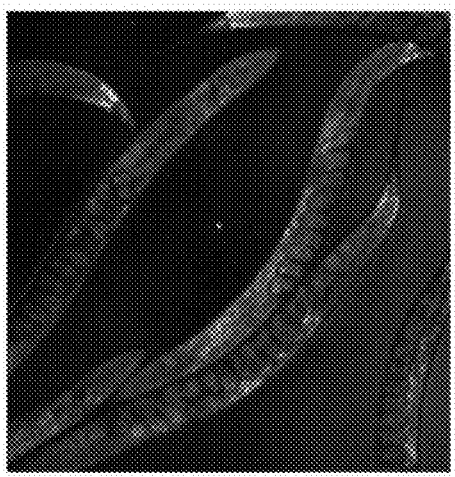
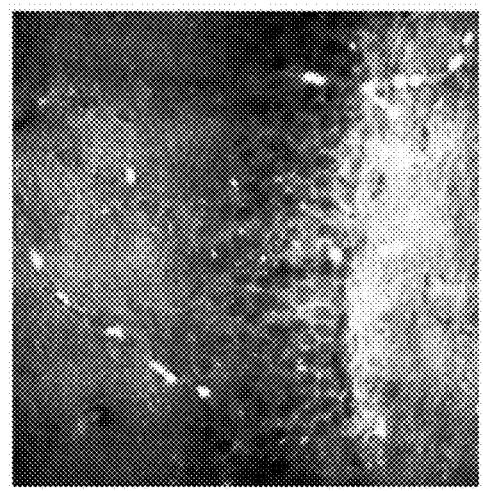
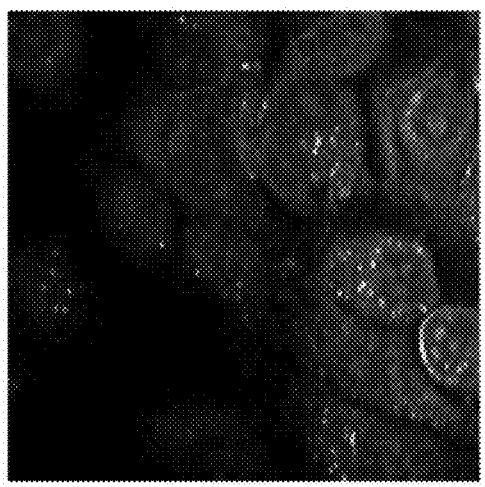
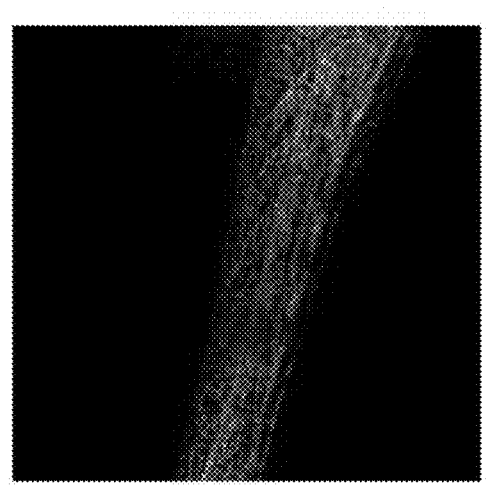
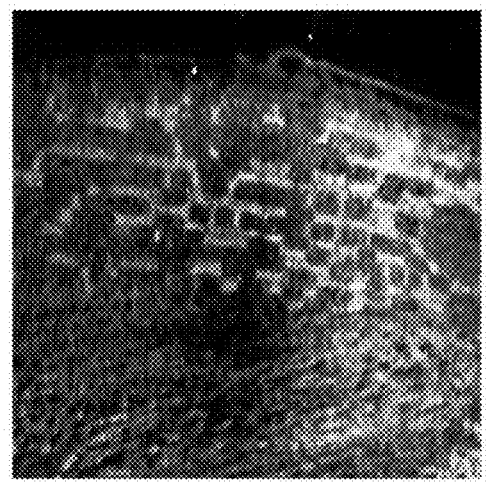
FIG. 31

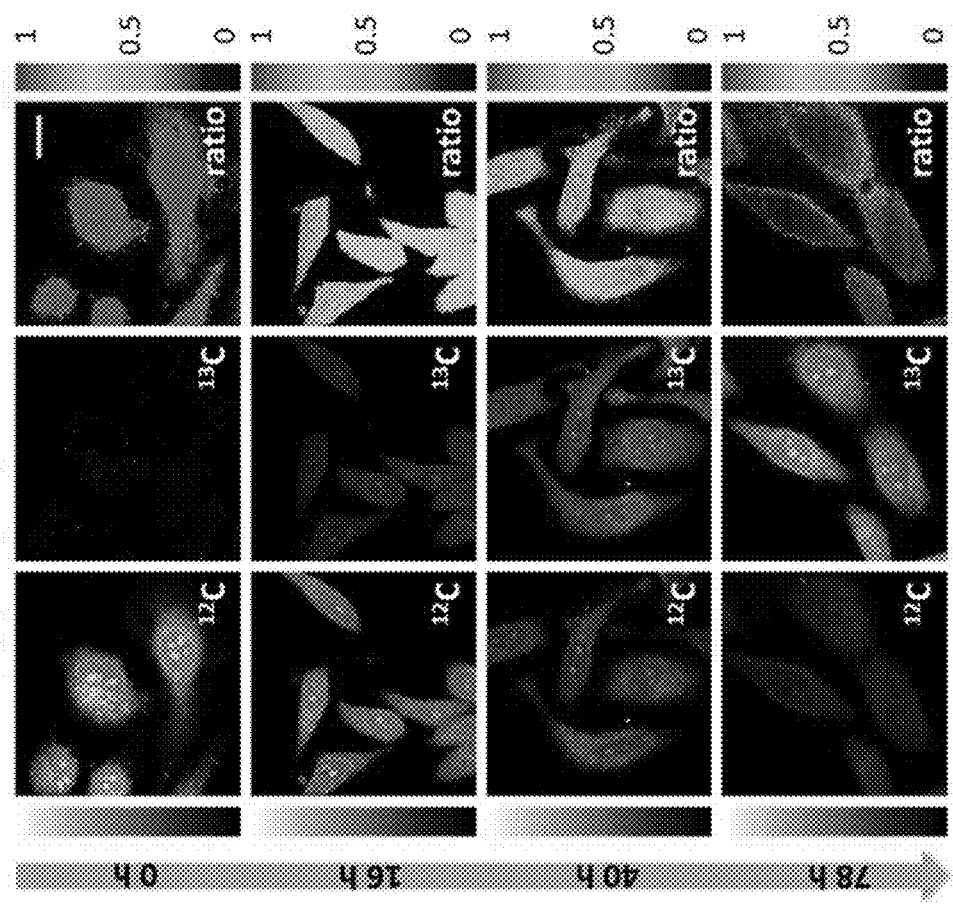
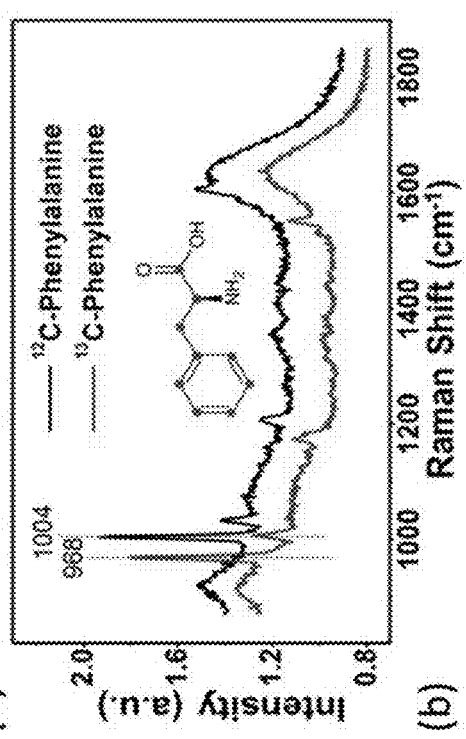
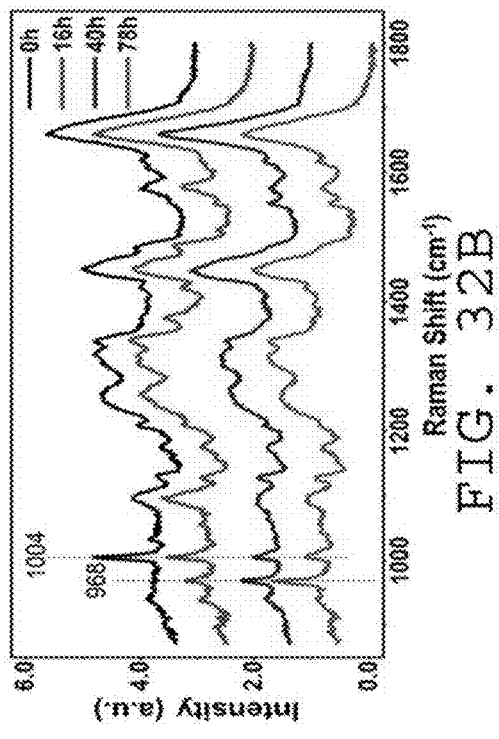
FIG. 32A, FIG. 32B, FIG. 32C
FIG. 32

FIG. 33A  FIG. 33B  FIG. 33C
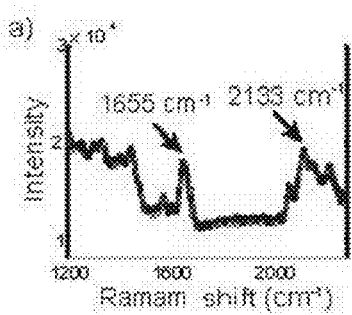 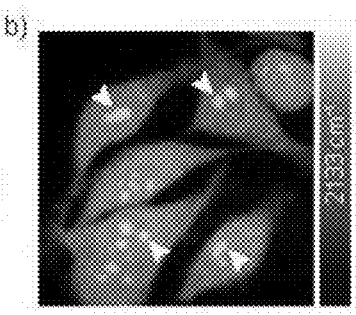 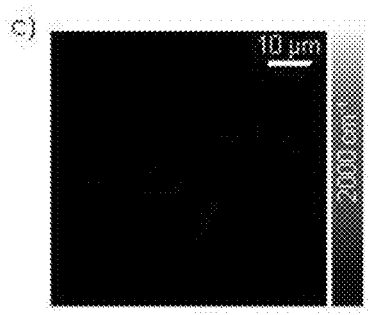
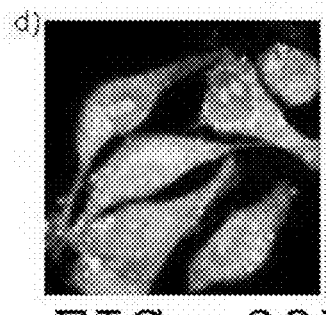 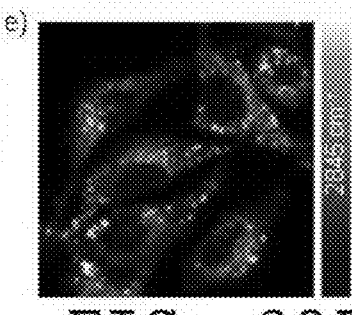 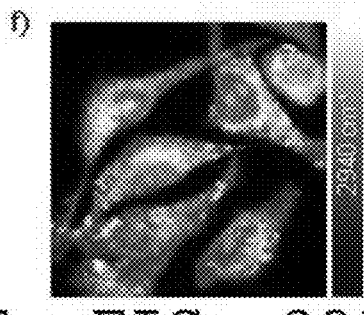
FIG. 33D  FIG. 33E  FIG. 33F
*FIG. 33*

FIG. 35A 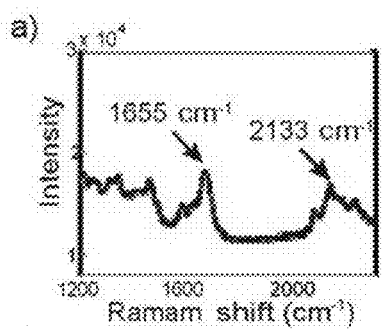 FIG. 35B 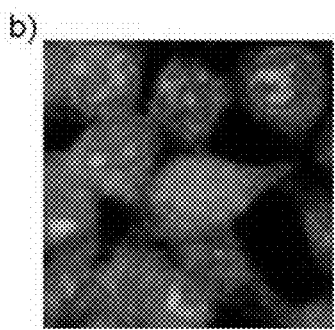 FIG. 35C 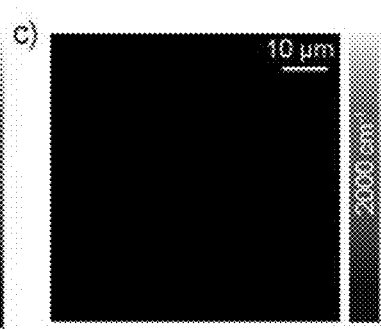
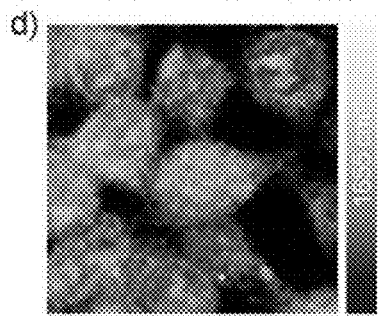 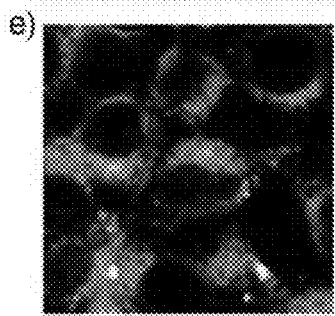 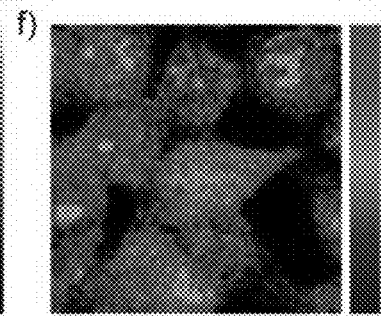
FIG. 35D  FIG. 35E  FIG. 35F
*FIG. 35*

FIG. 36A 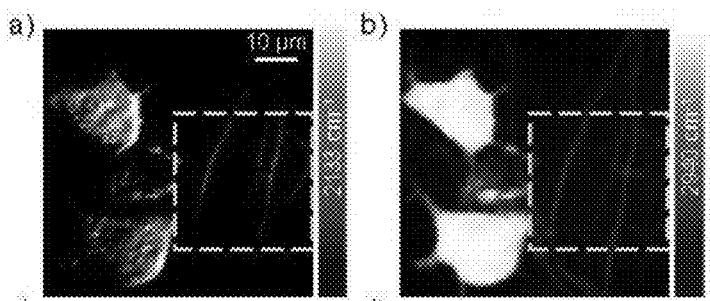 FIG. 36B
FIG. 36C 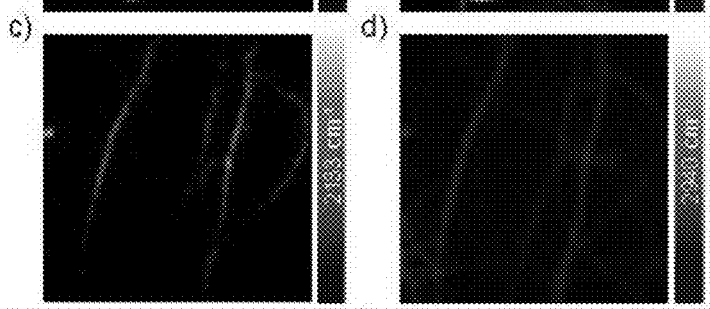 FIG. 36D
FIG. 36E 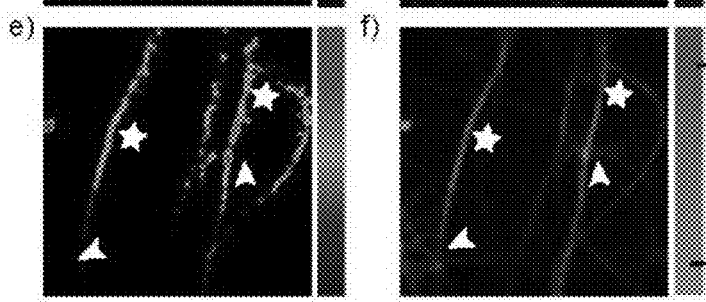 FIG. 36F
*FIG. 36*

Regular recipe for mammalian cell culture from Invitrogen website
*http://www.invitrogen.com/site/us/en/home/support/Product-Technical-Resources/media_formulation.8.html*
11965 - DMEM, high glucose
Catalog Number(s): 11965084 ,11965092 ,11965118 ,11965126 ,11965167 ,11965175

| Components | Molecular Weight | Concentration (mg/L) | mM |
|---|---|---|---|
| Amino Acids | | | |
| Glycine | 75 | 30 | 0.4 |
| L-Arginine hydrochloride | 211 | 84 | 0.398 |
| L-Cystine 2HCl | 313 | 63 | 0.201 |
| L-Glutamine | 146 | 584 | 4 |
| L-Histidine hydrochloride-H2O | 210 | 42 | 0.2 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.4 |
| L-Serine | 105 | 42 | 0.4 |
| L-Threonine | 119 | 95 | 0.798 |
| L-Tryptophan | 204 | 16 | 0.0784 |
| L-Tyrosine disodium salt dihydrate | 261 | 104 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3"9H2O) | 404 | 0.1 | 0.000248 |
| Magnesium Sulfate (MgSO4) (anhyd.) | 120 | 97.67 | 0.814 |
| Potassium Chloride (KCl) | 75 | 400 | 5.33 |
| Sodium Bicarbonate (NaHCO3) | 84 | 3700 | 44.05 |
| Sodium Chloride (NaCl) | 58 | 6400 | 110.34 |
| Sodium Phosphate monobasic (NaH2PO4-H2O) | 138 | 125 | 0.906 |
| Other Components | | | |
| D-Glucose (Dextrose) | 180 | 4500 | 25 |
| Phenol Red | 376.4 | 15 | 0.0399 |

*FIG. 37a*

Our designed corresponding deuterium-labeled recipe

| Components | Molecular Weight | Concentration (mg/L) | mM |
|---|---|---|---|
| Amino Acids | | | |
| Glycine-D2 | 75 | 30 | 0.4 |
| L-Arginine hydrochloride-D7 | 211 | 84 | 0.398 |
| L-Cystine 2HCl - D2 | 313 | 63 | 0.201 |
| L-Glutamine - D5 | 146 | 584 | 4 |
| L-Histidine hydrochloride-H2O | 210 | 42 | 0.2 |
| L-Isoleucine - D10 | 131 | 105 | 0.802 |
| L-Leucine - D10 | 131 | 105 | 0.802 |
| L-Lysine hydrochloride - D8 | 183 | 146 | 0.798 |
| L-Methionine-D3 | 149 | 30 | 0.201 |
| L-Phenylalanine-D8 | 165 | 66 | 0.4 |
| L-Serine-D3 | 105 | 42 | 0.4 |
| L-Threonine-D5 | 119 | 95 | 0.798 |
| L-Tryptophan | 204 | 16 | 0.0784 |
| L-Tyrosine disodium salt dehydrate- D2 | 261 | 104 | 0.398 |
| L-Valine- D8 | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| i-Inositol | 180 | 7.2 | 0.04 |
| Inorganic Salts | | | |
| Calcium Chloride (CaCl2) (anhyd.) | 111 | 200 | 1.8 |
| Ferric Nitrate (Fe(NO3)3"9H2O) | 404 | 0.1 | 0.000248 |
| Magnesium Sulfate (MgSO4) (anhyd.) | 120 | 97.67 | 0.814 |
| Potassium Chloride (KCl) | 75 | 400 | 5.33 |
| Sodium Bicarbonate (NaHCO3) | 84 | 3700 | 44.05 |
| Sodium Chloride (NaCl) | 58 | 6400 | 110.34 |
| Sodium Phosphate monobasic (NaH2PO4-H2O) | 138 | 125 | 0.906 |
| Other Components | | | |
| D-Glucose (Dextrose) | 180 | 4500 | 25 |
| Phenol Red | 376.4 | 15 | 0.0399 |

*All the marked deuterium labeled amino acids are available from Cambridge isotope or signal-aldrich.*

FIG. 37b

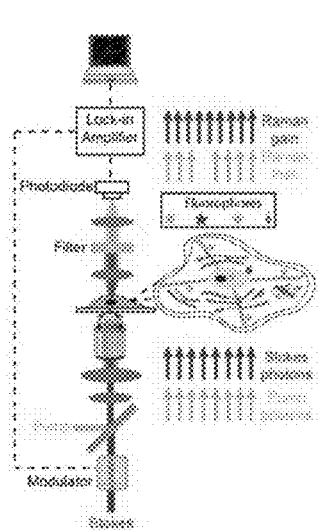
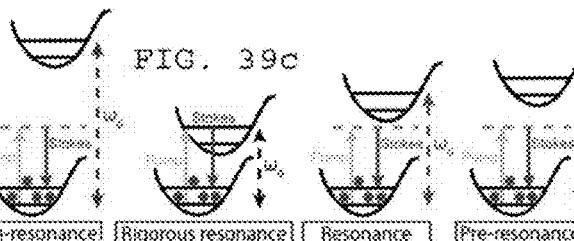
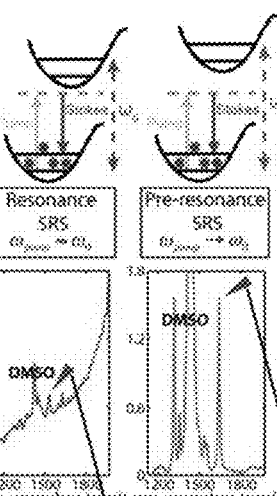
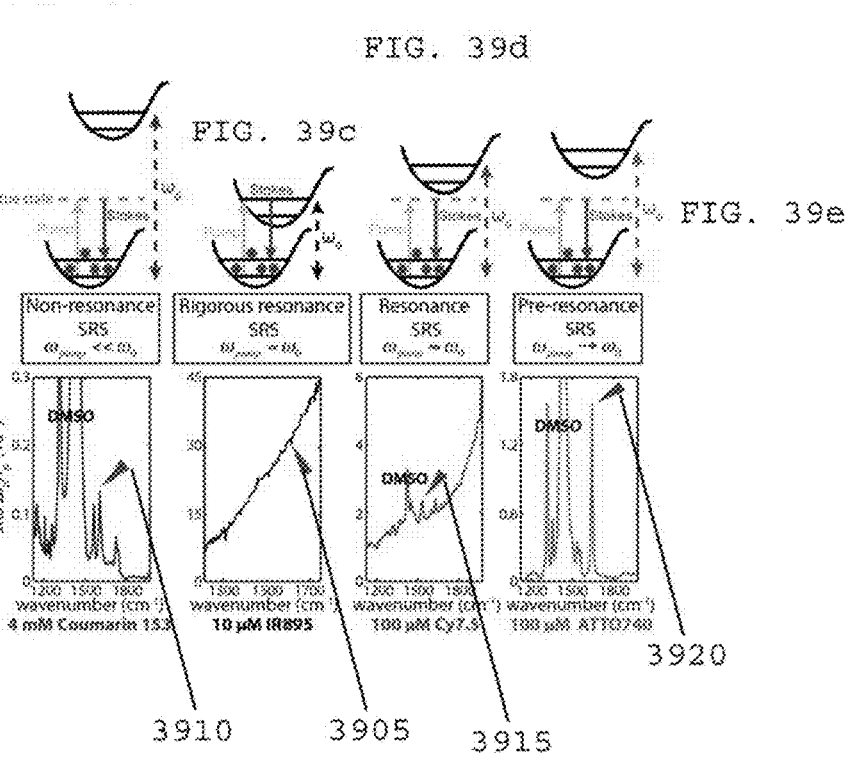
FIG. 39a FIG. 39b FIG. 39c FIG. 39d FIG. 39e FIG. 41a   FIG. 41b
FIG. 41c 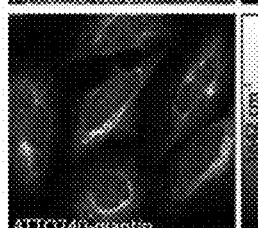  FIG. 41d
FIG. 41e 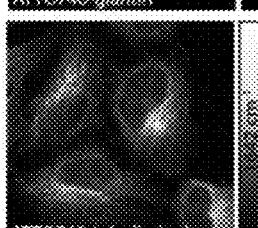  FIG. 41f
FIG. 41g 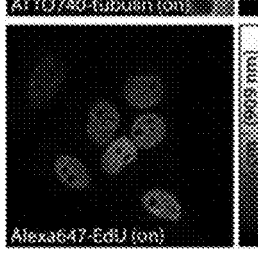  FIG. 41h
FIG. 41i   FIG. 41j

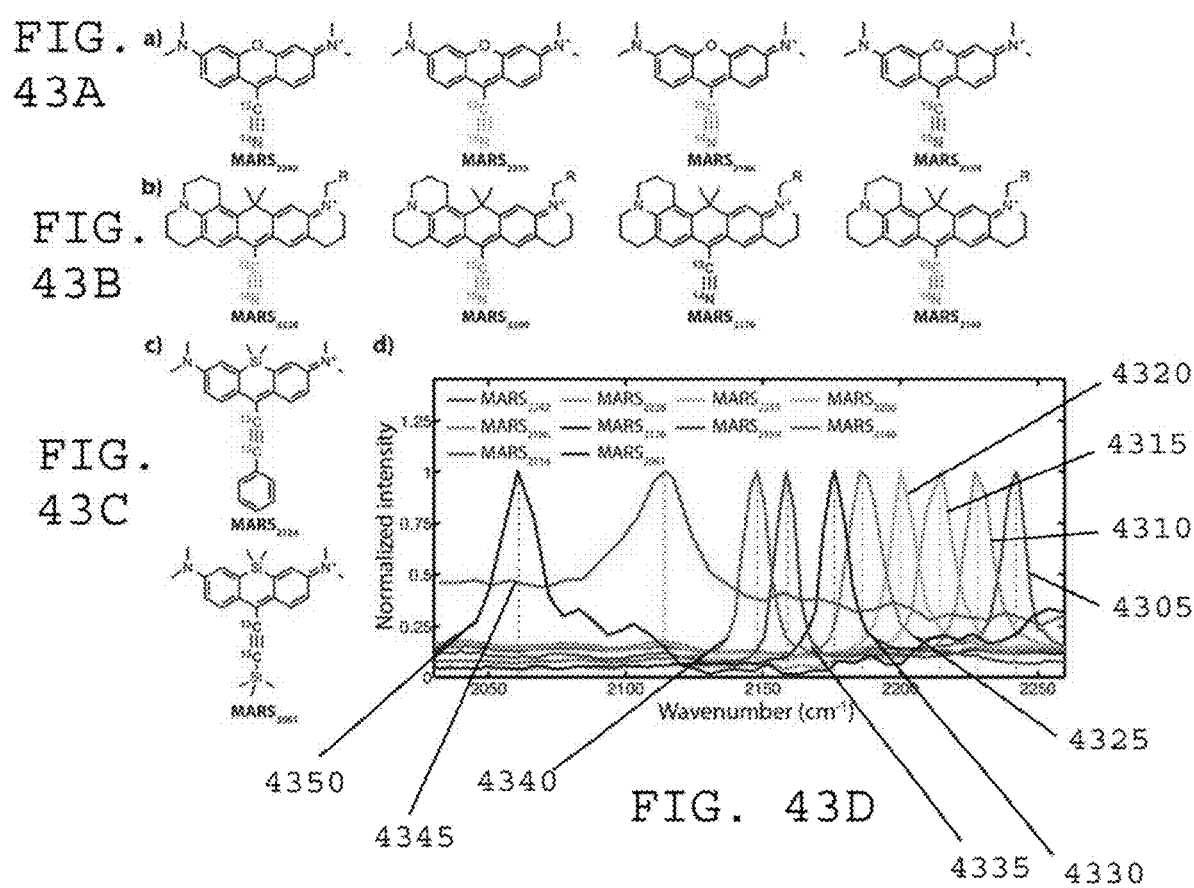

DEVICES, COMPOSITIONS AND METHODS FOR IMAGING WITH RAMAN SCATTERING

CROSS-REFERENCE TO RELATED APPLICATION

This application is a divisional of U.S. Non Provisional patent application Ser. No. 14/974,992 filed on Dec. 18, 2015, which is a continuation-in-part of International Patent Application No. PCT/US2014/042936, filed on Jun. 18, 2014, and published as International Patent Publication WO 2014/205074 on Dec. 24, 2014, which claims the priority of U.S. Provisional Application Nos. 61/836,235, filed Jun. 18, 2013, and 61/946,296, filed Feb. 28, 2014. This application also relates to and claims priority from U.S. Patent Application No. 62/112,906, filed on Feb. 6, 2015. The entire disclosures of the above applications are incorporated herein by reference in their entireties.

STATEMENT REGARDING FEDERALLY SPONSORED RESEARCH

This invention was made with government support under EB016573 and EB020892, awarded by the National Institutes of Health. The government has certain rights in the invention.

FIELD OF THE DISCLOSURE

The present disclosure relates generally to imaging technology, and in particular to vibrational microscopy and spectroscopy with Raman scattering technology.

BACKGROUND INFORMATION

Innovations in light microscopy have expanded the knowledge of biological processes at the microscopic level. In particular, fluorescence microscopy, utilizing versatile fluorescent probes (e.g. genetic labeling of fluorescent proteins, organic dyes and quantum dots) (See, e.g., References 1-3), can facilitate specific detection of molecules of interest in biological systems, facilitating people to actually visualize and understand fundamental processes. Taking advantage of the development of fluorescent probes (e.g. brighter, more photostable, multicolor etc.) (See, e.g., Reference 4), fluorescent microscopy such as confocal microscopy, two-photon microscopy, single molecule microscopy and super-resolution microscopy have enabled detection of structures that can be much deeper and finer than before. However, according to quantum mechanics (e.g. particle in the box), the chromophore within a fluorophore have to be a large conjugation system in order for the efficient absorption in the visible spectrum. Thus, in spite of the significance in various applications such as in cell biology, fluorescent tags intrinsically cannot be properly used for tagging small molecules such as glucose, nucleosides, amino acids, choline, fatty acids and small molecule drugs, for their relatively large size perturbs with the small molecule dynamics.

An opposite strategy for visualizing these important building block small molecules in biological systems can be label-free imaging. Representative imaging procedures of the kind can include vibration microscopies based on infrared absorption and Raman scattering detecting the characteristic vibrational mode of specific chemical bond from the molecules themselves (See, e.g., References 5-9). Other label-free procedures can be second harmonic generation ("SHG"), imaging special non-centrosymmetric structures, third harmonic generation ("THG"), sensing interfaces and optical heterogeneities and optical coherence tomography ("OCT"), measuring the backscattered light from tissues through low-coherence interferometry. However, label-free imaging can suffer from two fundamental problems: first, there can be insufficient specificity because small molecules usually do not have unique spectroscopic signature in the vast pool of other biomolecules; second, there can be unsatisfying sensitivity due to usually low concentration of the small molecules in the biological systems.

As an imaging tag, alkyne (e.g. carbon-carbon triple bond) can offer three advantages over others. First, alkyne is only a chemical bond, second alkyne can enable background-free detection, and third, alkyne can be inert to react with any intrinsic bio-molecules in the biological systems. In fact, alkyne can be widely used in the powerful bioorthogonal chemistry utilizing alkyne-azide specific click-chemistry reaction for various purposes (See, e.g., References 10-12). For example, using alkyne tagged molecule of interest followed by azide tagged detection reagent (e.g. affinity probes or fluorescent tag) can enable detection using mass spectrometry or fluorescence microscopy.

The proteome of a cell can be highly dynamic in nature and tightly regulated by both protein synthesis and degradation to actively maintain homeostasis. Many intricate biological processes, such as cell growth, differentiation, diseases and response to environment stimuli, can require protein synthesis and translational control (See, e.g., Reference 24). In particular, long-lasting forms of synaptic plasticity, such as those underlying long-term memory, can need new protein synthesis in a space- and time-dependent manner (See, e.g., References 26-30). Therefore, direct visualization and quantification of newly synthesized proteins at a global level can be indispensable to unraveling the spatial-temporal characteristics of the proteomes in live cells.

Extensive efforts have been devoted to probing protein synthesis via fluorescence contrast. The inherent fluorescence of green fluorescent protein ("GFP") and its genetic encodability, can the following of a given protein of interest inside living cells with high spatial and temporal resolution (See, e.g., References 29 and 30). However, GFP tagging through genetic manipulation works only on individual proteins, and not at the whole proteome level. To probe newly synthesized proteins at the proteome level, a powerful procedure named bioorthogonal noncanonical amino acid tagging (BONCAT) was developed by metabolic incorporation of unnatural amino acids containing reactive chemical groups such as azide or alkyne. (See, e.g., References 31-37). A related labeling method was recently demonstrated using an alkyne analog of puromycin. (See, e.g., Reference 28). Newly synthesized proteins can then be visualized through subsequent conjugation of the reactive amino acids to fluorescent tags via click chemistry. (See, e.g., Reference 29). Unfortunately, these fluorescence-based methods generally use non-physiological fixation and subsequent dye staining and washing.

In addition to fluorescence tagging, radioisotope or stable isotope, labeling can be another powerful tool to trace and quantify proteome dynamics. Classical radioisotope-labeled amino acids (e.g., 35S-methionine) can provide vigorous analysis of global protein synthesis. However, samples must be fixed and then exposed to film for autoradiography. For stable isotopes, the discovery of deuterium by Urey in 1932 immediately led to the pioneer work of Schoenheimer and Rittenberg studying intermediary metabolism. (See, e.g., References 40 and 51). To study proteome changes between different cells or under different conditions, stable isotope labeling by amino acids in cell culture ("SILAC") coupled with mass spectrometry ("MS") has matured into a popular method for quantitative proteomics (See, e.g., References 42-45). However, SILAC-MS does not usually provide spatial information down to sub-cellular level and its invasive nature limits its application for live cell imaging. The same limitation applies to the recent ribosome profiling study using deep sequencing procedure (See, e.g., Reference 46).

Spontaneous Raman microscopy has been used for label-free molecular and biomedical imaging (See, e.g., References 8, 13, 17, 59 and 73-77). However, this technology suffers from low sensitivity and slow imaging speed.

Among various optical imaging techniques, fluorescence microscopy may be one of the most widely adopted imaging modalities, because it offers single-molecule sensitivity for the visualization of a wide variety of molecules labeled with fluorophores. (See, e.g., References 79-81). Such sensitivity, together with recent technical developments, has enabled the use of a two-photon fluorescence microscopy for deep tissue and in vivo imaging (see, e.g., Reference 82), super-resolution fluorescence microscopy that breaks the diffraction limit for nanometer scale resolution (see, e.g., References 83-85), and fluorescence resonance energy transfer microscopy for imaging intracellular molecular interactions. (See, e.g., Reference 86). However, fluorescence microscopy generally probes the electronic transition of the fluorophores, resulting in both featureless and broadband (e.g., bandwidth of about 50-100 nm) absorption and emission spectra, mainly due to strong electronic state dephasing. (See, e.g., References 87 and 88). Thus, two fluorophores with distinct structures can result in overlapping and unresolvable spectra, which likely limits the simultaneously detected fluorophores (e.g., typically to 4).

Currently, non-fluorescence based imaging techniques offering single-molecule sensitivity are commonly absorption-based methods, such as measuring photothermal contrast, ground state depletion from a single molecule, or using balanced detector and index-matched sample geometry (see, e.g., References 89-91), which can all yield a similar number of colors for simultaneous multiplex imaging as in fluorescence microscopy. Nevertheless, multicolor imaging of up to tens of colors can be highly demanded for real biomedical applications, such as imaging various types of tumor receptors simultaneously in cancer research (see, e.g., References 92 and 93), to detect cancer markers in biomedical diagnostics by flow cytometer (see, e.g., Reference 94), and to follow the highly dynamic focal adhesion complex for the research of cell interactions with the extracellular matrix. (See, e.g., Reference 95).

As an alternative, Raman microscopy can potentially image up to tens or hundreds of molecules simultaneously by probing the vibrational transition of the molecules and offering distinct and sharp Raman peaks with chemical specificity. (See, e.g., Reference 96). Thus, two molecules with close chemical structures could possibly be resolved in Raman spectrum. However, spontaneous Raman, as a single-laser technique, likely suffers from an extremely weak sensitivity that can be about 1010-1012 times weaker than fluorescence. Thus, for imaging biological samples, spontaneous Raman microscopy can be an undesirable technique because of the long acquisition time needed, and the large sample auto-fluorescence background. A current Raman technique, Surfaced Enhanced Raman Scattering ("SERS"), provides a remarkable sensitivity even at single molecule level (see, e.g., References 97 and 98). However, this technique relies on the enhancement from metal surface plasmons that can benefit from nanometer-precision positioning between the sample and the metal surface, therefore prohibiting its application in intracellular cell imaging.

Thus, it may be beneficial to have an imaging strategy that makes up for the gap between fluorescence microscopy and label-free imaging for the sensitive and specific detection of small molecules while offering minimum perturbation to the biological systems (e.g. to have small tags with distinct spectroscopic characteristics), and which can overcome at least some of the deficiencies described herein above.

SUMMARY OF EXEMPLARY EMBODIMENTS

One exemplary aspect of the present disclosure relates to a method for obtaining biological information in a living cell or a living organism with bond-edited compounds using stimulated Raman scattering. The method comprises the steps of introducing one or more bond-edited compounds into a live cell or a living organism, and detecting a vibrational tag in the cell or organism with stimulated Raman scattering.

Another exemplary aspect of the present disclosure relates to methods for making a bond-edited compound.

Another exemplary aspect of the present disclosure relates to a method for detecting a disease condition in a subject, comprising: administering to said subject a composition comprising a bond-edited compound targeting a disease tissue or pathogen, and detecting said bond-edited compound by stimulated Raman scattering.

Another exemplary aspect of the present disclosure relates to a method for monitoring a treatment for a disease condition. The method comprises administering to the subject a composition comprising a bond-edited compound and detecting the bond-edited compound by stimulated Raman scattering at a first time point, performing the treatment after the first time point, further administering to said subject the composition comprising a bond-edited compound, and detecting the bond-edited compound by stimulated Raman scattering at a second time point, and comparing images obtained at the two time points, Another exemplary aspect of the present disclosure relates to a method for screening an agent. The method comprises administering the agent and at least one bond-edited compound to a live cell or organism, detecting the bond-edited compound in the live cell or organism using stimulated Raman scattering, and selecting a candidate agent based on one or more predetermined criteria, such as the uptake, accumulation, trafficking or degradation of the bond-edited compound by the said live cell or organism.

Another exemplary aspect of the present disclosure relates to a device for imaging bond-edited compounds by stimulated Raman scattering. The device comprises a first single-wavelength laser source that produces a pulse laser beam of a first wavelength, a second single-wavelength laser source that produces a pulse laser beam of a second wavelength, a modulator that modulates the pulse laser beam of one of the first or second laser source, a photodetector that is capable of or configured to detect stimulated Raman scattering from a biosample, and a computer.

Another exemplary aspect of the present disclosure relates to a non-transitory computer-accessible medium having stored thereon computer-executable instructions for determining data associated with at least one tissue, wherein, when a computer hardware arrangement executes the instructions, the computer arrangement is configured to perform procedures comprising: receiving first information related to at least one bond between at least two atoms attached to a metabolite; and determining the data based on the at least one bond.

Another exemplary aspect of the present disclosure relates to a method for determining data associated with at least one tissue, comprising: receiving first information related to at least one bond between at least two atoms attached to a metabolite; and using a computer hardware arrangement, determining the data based on the at least one bond.

Another exemplary aspect of the present disclosure relates to a system for determining data associated with at least one tissue, comprising: a computer processing arrangement configured to receive first information related to at least one bond between at least two atoms attached to a metabolite; and determine the data based on the at least one bond.

Another exemplary aspect of the present disclosure relates to a pre-mixed essential amino acid combination, comprising: at least one non-deuterated essential amino acid; and at least 5 deuterated essential amino acids.

Another exemplary aspect of the present disclosure relates to a method for exciting a light absorbing molecule(s) can include, for example, labeling a target molecule(s) to create the light absorbing molecule(s) using a label(s) having a resonance energy level, and forwarding a radiation(s) to the light absorbing molecule(s) at an energy output level so as to excite the light absorbing molecule(s), where a difference between the resonance energy level and the energy output level can be within a predetermined range. The range can be between about 500 cm-1 to about 2000 cm-1. The radiation(s) can include a laser light, and can also include two radiations. The radiation(s) can be generated using a stimulated Raman scattering arrangement. The label(s) can include a chromophore(s).

In certain exemplary embodiments of the present disclosure, the chromophore(s) can include a dye, which can include an alkyne(s). The alkyne(s) can include an isotopically modified alkyne(s). An image(s) can be generated using a resultant radiation received from the excited light absorbing molecule(s) that can be based on the forwarded radiation(s). The light absorbing molecule(s) can include a chromophore or a fluorophore.

In some exemplary embodiments of the present disclosure, a further target molecule(s) can be labeled to create a further light absorbing molecule(s) using a further label(s) having a further resonance energy level, and the radiation(s) can be forwarded to the further light absorbing molecule(s) at the energy output level so as to excite that further light absorbing molecule(s), where the difference between the further resonance energy level and the energy output level can be within the predetermined range. The further resonance energy level can be different than the resonance energy level. A vibrational spectrum of the light absorbing molecule(s) can be different than the vibrational spectrum of the further light absorbing molecule(s).

Another exemplary aspect of the present disclosure relates to a system, which can include, for example, a label(s) of a target molecule(s) having a resonance energy level, and a radiation generating arrangement(s) providing a radiation(s) to the target molecule(s) that can have an energy output level, where a difference between the resonance energy level and the energy output level can be within a predetermined range. The predetermined range can be between about 500 cm-1 to about 2000 cm-1. The radiation generating arrangement(s) can include a stimulated Raman scattering arrangement. The label can include a chromophore(s), which can include a dye.

Still a further exemplary embodiment of the present disclosure can be a label, which can include, for example, a chromophore(s), and an isotopically modified alkyne(s). The label can also include a chemical(s) or a light absorbing protein(s).

A further exemplary embodiment of the present disclosure is a method for imaging a living cell or a living organism, which can include introducing an effective amount of a bond-edited compound into a live cell or a living organism, where the bond-edited compound comprises a vibrational tag, and detecting the vibrational tag in the cell or the organism with stimulated Raman scattering (SRS) imaging. The bond-edited compound can be a small molecule The bond-edited compound can include one, two, three, four, five, six, seven, eight, nine, ten or more vibrational tags. The vibrational tags can be the same type of tags or a mixture of one or more different tags, and can include an alkyne tag, an azide tag, an isotope label, or a combination of an alkyne tag and a carbon-deuterium bond tag. The isotope label can be a carbon-deuterium bond tag. The bond-edited compound can include a vibrational tag(s) of —C≡C—, —C≡N, —N=N=N, —C≡C=C≡C—, —C≡C=C≡N, —C-D, and —C≡C-D, at least one 13C atom or one deuterium atom, an amino acid, a nucleoside or a nucleotide, a fatty acid, a monosaccharide or a disaccharide, glucose, a glucose derivative or propargyl glucose, or a cytokine or chemokine.

In some exemplary embodiments of the present disclosure, the amino acid can be an essential amino acid, and can be histidine, isoleucine, leucine, lysing, methionine, phenylalanine, threonine, tryptophan or valine. The bond-edited compound can also be selected from anti-cancer agents, anti-inflammatory agents, anti-bacterial agents, anti-fungal agents or anti-viral agents. The vibrational tag can be transferred from the bond-edited compound to a down-stream metabolite of the bond-edited compound, and can be detected in the down-stream metabolite.

In yet another exemplary embodiment of the present disclosure is a method for imaging a living cell or a living organism, which can include introducing into the live cell or organism a mixture of two or more bond-edited compounds wherein the two or more bond-edited compounds each comprises a different vibrational tag, and imaging with stimulated Raman scattering at two or more different wavelengths to detect the vibrational tag on each of the two or more bond-edited compounds. The two or more bond-edited compounds can include EU-13C2, EdU-13C and 17-ODYA, and can different cellular components, the same cellular component but at different time period, different types of cells in the living organism, or two or more bond-edited compounds detected using a linear combination algorithm.

In certain exemplary embodiments of the present disclosure, the vibrational tag on each of the two or more bond-edited compounds can be detected using a linear combination algorithm.

Another exemplary embodiment of the present disclosure can be a method for making a alkyne-tagged compound, which can include adding propargyl bromide to a compound of formula S1 in the presence of DMF and sodium hydride to produce a compound of formula S2;

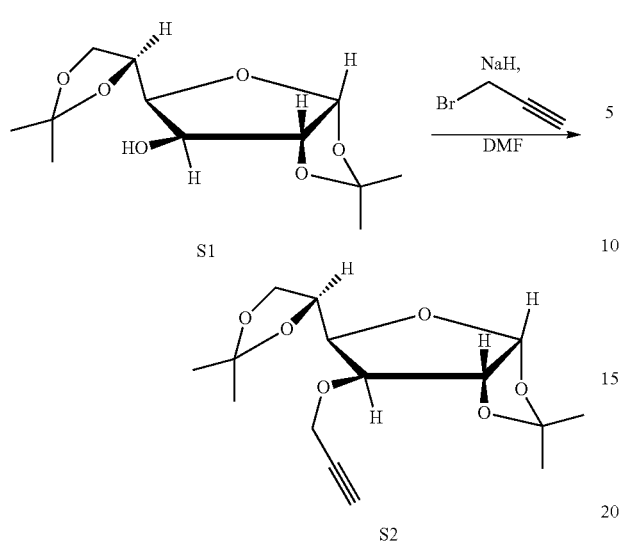

S1

S2 and, adding water and an ion exchange resin to the compound of formula S2 to produce a compound of formula S3

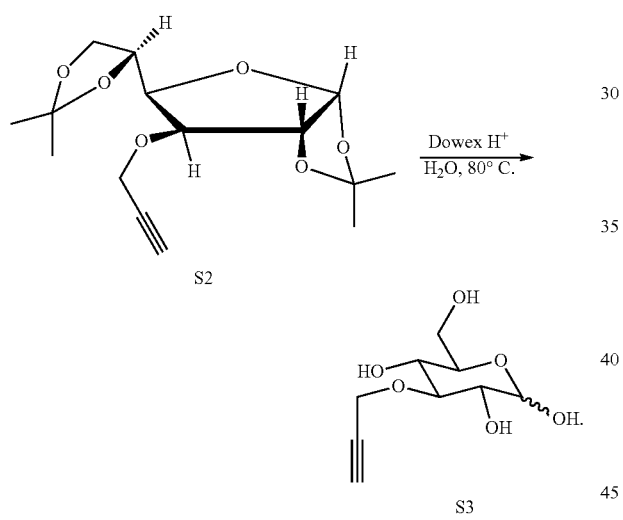

S2

S3

Still a further exemplary embodiment of the present disclosure is a method for making a 13C-tagged compound, which can include reacting a compound of formula 5 with K2CO3, MeOH and H2O to produce the compound of formula 3:

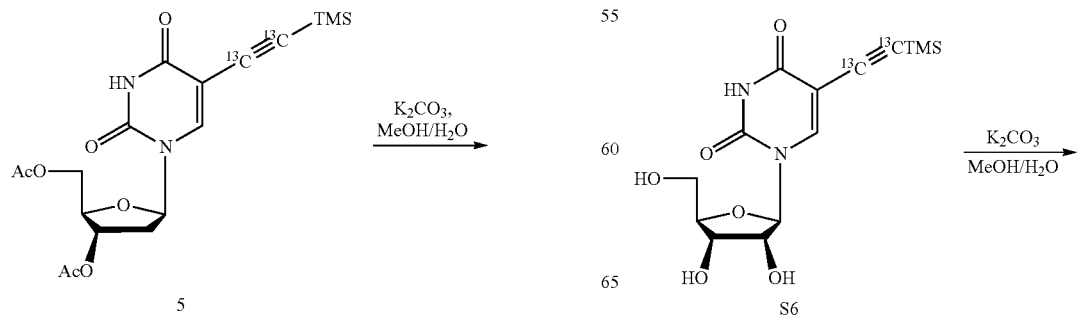

5

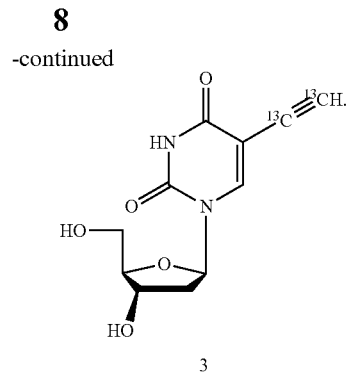

3

Yet a further exemplary embodiment of the present disclosure is a method for making a 13C-tagged compound, which can include reacting a compound of formula 10 with TBAF, K2CO3, MeOH and H2O to produce the compound of formula 2:

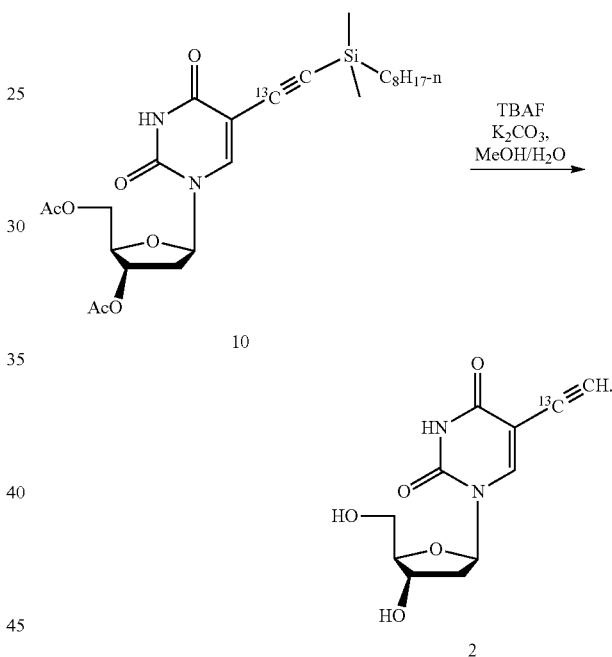

10

2

Yet an even further exemplary embodiment of the present disclosure is a method for making a 13C-tagged compound, comprising: reacting a compound of formula S6 with K2CO3, MeOH and H2O to produce the compound of formula 13:

S6

-continued

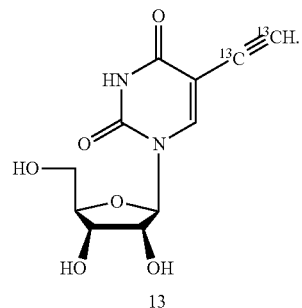
13

An even further exemplary embodiment of the present disclosure is a alkyne-tagged compound of formula S3,

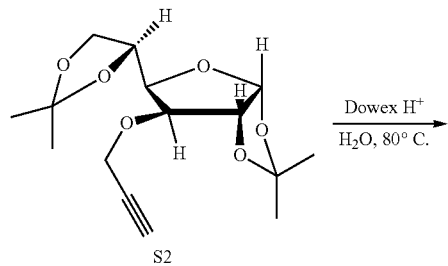

A compound of formula 3 can be

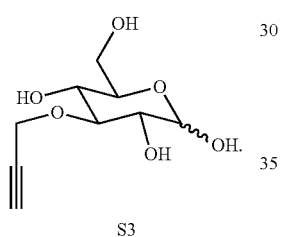
5

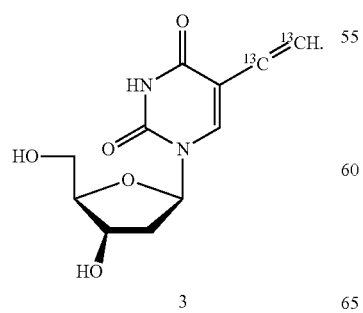
3

A compound of formula 2 can be

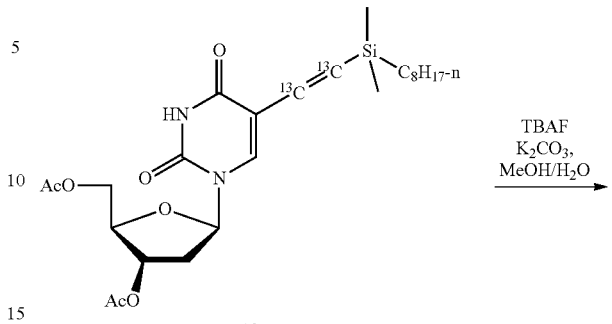

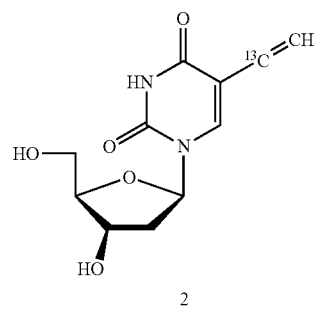
2

A compound of formula 13 can be

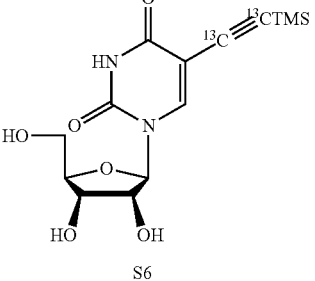

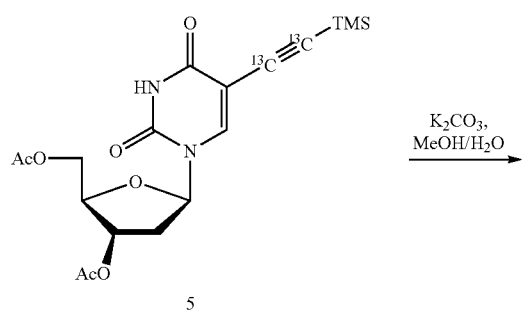

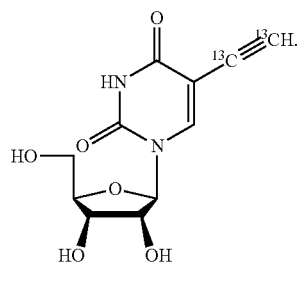
13

An even further exemplary embodiment of the present disclosure is a method for detecting a disease condition in a subject, which can include administering to the subject a composition comprising a bond-edited compound targeting a disease tissue or pathogen, where the bond-edited compound comprises a vibrational tag, and detecting the vibrational tag by stimulated Raman scattering imaging. The disease condition can include cancer, metabolic syndrome, neurodegenerative diseases, inflammatory diseases and microbial infections. The vibrational tag can be transferred from the bond-edited compound to a down-stream metabolite of the bond-edited compound, and can be detected in the down-stream metabolite.

Additionally, a method for monitoring a treatment for a disease condition in a subject, can include administering to the subject a composition comprising a bond-edited compound and detecting the bond-edited compound by stimulated Raman scattering imaging at a first time point, further administering to the subject the composition comprising a bond-edited compound, detecting the bond-edited compound by stimulated Raman scattering imaging at a second time point and comparing images obtained at the two time points. The first time point can be a time point that can be about or prior to the initiation of the treatment and the second time point can be a time point that can be after the initiation of the treatment. The first time point and the second time point can be two time points during the course of the treatment.

A further exemplary embodiment of the present disclosure can include a method for screening a candidate agent, which can include administering the candidate agent and a bond-edited compound(s) to a live cell or organism, detecting the bond-edited compound in the live cell or organism using stimulated Raman scattering imaging and determining an effectiveness of the candidate agent based on one or more predetermined criteria selected from the group consisting of the uptake, accumulation, trafficking and degradation of the bond-edited compound in the live cell or organism. The candidate agent can be an anti-cancer drug, or a skin regenerating agent.

A still further exemplary embodiment of the present disclosure can include a device for imaging bond-edited compounds by stimulated Raman scattering, which can include a first laser generator that can produce a pulse laser beam of a first fixed wavelength, a second laser generator that can produce a pulse laser beam of a second fixed wavelength, a modulator that can modulate the pulse laser beam of the first or second laser generator, a photodetector that can be adapted to detecting the stimulated Raman scattering from a biosample and a computer which generates an image(s) of the bond-edited compounds based on the detected stimulated Raman scattering. The first and second laser generators can be configured to provide a pump radiation and a stokes radiation, each at a fixed wavelength whose energy difference can be between about 2000 and 2500 wavenumbers.

An even further exemplary embodiment of the present disclosure can include a system, method and computer-accessible medium for receiving first information related to a bond(s) between at least two atoms attached to a metabolite and determining the data based on the bond(s). The bond can be a carbon deuterium bond, a triple carbon bond, a triple carbon nitrogen bond, or an azide triple nitrogen bond. A deuterium to hydrogen ratio of the tissue can be at least 1 to 5,000. A deuterium to hydrogen ratio of the tissue can be at least 1 to 1,000. A deuterium to hydrogen ratio of the tissue can be at least 1 to at most 100. The data can include a location of the bond(s). The data can be determined based on an amplitude of a signal of the bond(s). The data can be determined using a stimulated Raman microscopy arrangement, a coherent anti-Stokes Raman scattering arrangement, an infrared absorption arrangement, a stimulated Raman excited photothermal arrangement, or a stimulated Raman excited photoacoustic arrangement.

In certain exemplary embodiments of the present disclosure, a laser of the stimulated Raman microscopy arrangement can be tuned to a particular frequency based on the bond(s). The tissue(s) can include a live animal cell(s). The metabolite can include (i) a deoxyribonucleoside(s), (ii) a ribonucleoside(s), (iii) an amino acid(s), (iv) choline, (v) a fatty acid(s), (vi) an Adenosine triphosphate(s), (vii) cholesterol, or (viii) a chemical drug(s).

A pre-mixed essential amino acid combination can include a non-deuterated essential amino acid(s) and at least 3 or at least 4 deuterated essential amino acids.

An exemplary method for exciting a light absorbing molecule(s) can include, for example, labeling a target molecule(s) to create the light absorbing molecule(s) using a label(s) having a resonance energy level, and forwarding a radiation(s) to the light absorbing molecule(s) at an energy output level so as to excite the light absorbing molecule(s), where a difference between the resonance energy level and the energy output level can be within a predetermined range. The range can be between about 500 cm-1 to about 2000 cm-1. The radiation(s) can include a laser light, and can also include two radiations. The radiation(s) can be generated using a stimulated Raman scattering arrangement. The label(s) can include a chromophore(s).

In certain exemplary embodiments of the present disclosure, the chromophore(s) can include a dye, which can include an alkyne(s). The alkyne(s) can include an isotopically modified alkyne(s). An image(s) can be generated using a resultant radiation received from the excited light absorbing molecule(s) that can be based on the forwarded radiation(s). The light absorbing molecule(s) can include a chromophore or a fluorophore.

In some exemplary embodiments of the present disclosure, a further target molecule(s) can be labeled to create a further light absorbing molecule(s) using a further label(s) having a further resonance energy level, and the radiation(s) can be forwarded to the further light absorbing molecule(s) at the energy output level so as to excite that further light absorbing molecule(s), where the difference between the further resonance energy level and the energy output level can be within the predetermined range. The further resonance energy level can be different than the resonance energy level. A vibrational spectrum of the light absorbing molecule(s) can be different than the vibrational spectrum of the further light absorbing molecule(s).

Another exemplary embodiment of the present disclosure can be a system, which can include, for example, a label(s) of a target molecule(s) having a resonance energy level, and a radiation generating arrangement(s) providing a radiation(s) to the target molecule(s) that can have an energy output level, where a difference between the resonance energy level and the energy output level can be within a predetermined range. The predetermined range can be between about 500 cm-1 to about 2000 cm-1. The radiation generating arrangement(s) can include a stimulated Raman scattering arrangement. The label can include a chromophore(s), which can include a dye.

Still a further exemplary embodiment of the present disclosure can be a label, which can include, for example, a chromophore(s), and an isotopically modified alkyne(s). The label can also include a chemical(s) or a light absorbing protein(s).

Still an even further exemplary embodiment of the present disclosure can be a label, which can include a chromophore(s) and an isotopically modified nitrile(s).

These and other objects, features and advantages of the exemplary embodiments of the present disclosure will become apparent upon reading the following detailed description of the exemplary embodiments of the present disclosure, as also exemplified by the appended claims.

BRIEF DESCRIPTION OF THE DRAWINGS

Further objects, features and advantages of the present disclosure will become apparent from the following detailed description taken in conjunction with the accompanying FIGS. showing illustrative exemplary embodiments of the present disclosure, in which:

FIG. 1 shows imaging complex protein metabolism by stimulated Raman scattering (SRS) microscopy in live cells, tissues and animals. For example, FIG. 1a illustrates a cartoon for SRS imaging following metabolic labeling of deuterated amino acids (D-AAs) in live organisms (e.g. mice), which are first administered with D-AAs for certain period of time and then imaged by SRS to probe protein metabolism. FIG. 1b illustrates spontaneous Raman spectra from HeLa cells incubated with medium containing either regular amino acids (gray, dashed) or D-AAs illustrate three distinct ways to probe complex protein metabolism: imaging newly synthesized proteins by targeting 2133 cm-1 from carbon-deuterium bonds (C-D), imaging degradation of pre-existing proteins by targeting the pure methyl group ($CH_3$) distribution, and two-color pulse-chase protein imaging by labeling with two sub-groups of D-AAs (i.e., group I and group II).

FIG. 2 depicts sensitivity optimization and time-lapse imaging of the de novo proteome synthesis dynamics. For example, FIG. 2a illustrates spontaneous Raman spectra of C-D peaks in HeLa cells incubated in optimized deuteration medium display a 50% increase when compared to the previously reported partial deuteration medium, and about 8 times higher than using leucine-$d_{10}$ only. FIG. 2b illustrates SRS images of newly synthesized proteins in live HeLa cells confirm a 50% average signal increase. FIG. 2c illustrates SRS images of newly synthesized proteins in live neurons in optimized deuteration medium for 20 h. The zoom-in image highlights the fine dendritic structures (likely dendritic spines, arrow-headed). FIG. 2d illustrates SRS image of newly synthesized proteins in live HeLa cells with 1 h incubation of optimized deuteration medium. Control image with protein synthesis inhibition deprives most of the signal. FIG. 2e illustrates time-lapse SRS images of protein synthesis dynamics in a same set of live HeLa cells with continuous incubation in optimized deuteration medium. Scale bar, 10 µm.

FIG. 3 shows time-dependent SRS images of protein degradation. For example, FIG. 3a illustrates adopting a linear combination algorithm between 2940 $cm^{-1}$ and 2845 $cm^{-1}$ channels, the obtained SRS image exclusively from $CH_3$ vibration display gradual degradation of pre-existing proteins in live HeLa cells cultured in optimized deuteration medium for 0 h, 24 h, 48 h and 96 h. FIG. 3b illustrates SRS images exclusively from $CH_2$ vibration display the total lipid distribution at the corresponding time point. FIG. 3c illustrates a single exponential decay fitting from averaged image intensities from pre-existing protein in FIG. 3a, yielding a protein degradation time constant of 45±4 h. Error bars, standard deviation. Scale bar, 10 µm.

FIG. 4 depicts pulse-chase SRS imaging of temporally defined proteins. For example, FIG. 4a illustrates structures and spontaneous Raman spectra of group I D-AAs (i.e. the branched chain amino acids). FIG. 4b illustrates structures and spontaneous Raman spectra of three examples of group II non-branched D-AAs. FIG. 4c illustrates spontaneous Raman spectra of HeLa cells cultured with group I D-AAs (element 405), showing multiple peaks with the first around 2067 $cm^{-1}$, and with group II D-AAs (element 410), showing a common peak around 2133 $cm^{-1}$. FIG. 4d illustrates two-color pulse-chase imaging by sequential labeling of group II and group I D-AAs in time with simultaneous expression of mutant huntingtin (mHtt94Q-mEos2) proteins. Cartoon displays experimental timeline of plasmid transfection and D-AA medium exchanges. The fluorescence image (overlaid with bright field) indicates the formation of a large aggregate (arrow-headed) of mHtt94Q-mEos2. The retrieved signals from linear combination of the original images at 2067 and 2133 channels display a large aggregation of mHtt proteins solely labeled by group II D-AAs during the first 22 h (pulse 415) and mHtt only labeled by group I D-AAs during the following 20 h (chase 420). The merged image, as well as the intensity profile, from the pulsed (element 415) and chased (element 420) images confirms with a yellow core and a green shell. Scale bar, 10 µm.

FIG. 5a illustrates SRS images at dentate gyrus of a live organotypic brain slice (400 µm thick, from a P10 mouse) after culturing in D-AA medium for 30 hr. 2133 $cm^{-1}$ (C-D) image presents the distribution of newly synthesized proteins. The $CH_3$ and $CH_2$ images show the old protein pools and total lipids, respectively. FIG. 5b illustrates a 4-by-3 mm large field view overlay image of new proteins (C-D, element 505), old proteins ($CH_3$, element 510) and total lipids ($CH_2$, element 515) for a brain slice (400 µm thick, from a P12 mouse) cultured in D-AA medium for 30 h. Scale bar, 100 µm.

FIG. 6a illustrates SRS images of a 24-hpf (hpf: hours post fertilization) zebrafish. Wild-type zebrafish embryos were injected at 1-cell stage with 1 nL D-AA solution and allowed to develop normally for another 24 h before imaging. Bright field image shows the gross morphology of embryonic zebrafish at 24 hpf (dashed boxes). 2133 $cm^{-1}$ (C-D) image presents the distribution of newly synthesized proteins (Supplemental FIG. 2a) in the somites of an embryonic zebrafish tail. The $CH_3$ image shows the old protein pool while the $CH_2$ image depicts total lipid in the same fish. FIGS. 6b and 6c SRS images of live mouse liver are shown in FIG. 6b and intestine tissues FIG. 6c harvested from mice after administered with D-AA containing drinking water for 12 days. 2133 $cm^{-1}$ (C-D) channel shows newly synthesized proteins (Supplemental FIG. 2b-2c that resemble the distribution of total protein as shown in the 1655 $cm^{-1}$ image (Amide I). Scale bar, 10 µm.

FIG. 7 depicts SRS images at 2067 $cm^{-1}$ and 2133 $cm^{-1}$ channels of proteins labeled with group I D-AA only shown in FIG. 7a and group II D-AA only shown in FIG. 7b.

FIG. 8 shows raw C-D on-resonance (2133 $cm^{-1}$) and off-resonance (2000 $cm^{-1}$) SRS images of newly synthesized proteins in vivo in FIG. 6a, which illustrates SRS C-D on-resonance and off-resonance images of a 24 hpf embryonic zebrafish. The difference image between C-D on-resonance and off-resonance (pixel-by-pixel subtraction) shows pure C-D labeled protein distribution in the somites of an embryonic zebrafish tail, as in FIG. 6. FIGS. 8b and 8c illustrate SRS C-D on-resonance and off-resonance images of live mouse liver FIG. 6b and intestine FIG. 6c tissues harvested from the mice after administering with D-AA containing drinking water for 12 days. The difference image between C-D on-resonance and off-resonance (pixel-by-pixel subtraction) shows pure C-D labeled protein distribution in the liver and intestine tissues, shown in FIG. 6b and FIG. 6c, respectively. The residual signal presented in the off-resonance images mainly comes from cross-phase modulation induced by highly scattering tissue structures.

FIG. 9 shows SRS imaging for newly synthesized proteins in vivo with intraperitoneal injection of mice with D-AA solutions. For example, FIGS. 9a and 9b illustrate SRS images of live mouse liver FIG. 9a and intestine FIG.

9b tissues harvested from mice after intraperitoneal injection injected with D-AAs solutions for 36 h. 2133 cm$^{-1}$ channel shows newly synthesized proteins (off-resonance image subtracted) that resemble the distribution of total proteins as shown in the 1655 cm$^{-1}$ image (Amide I). FIGS. 9c and 9d illustrate corresponding raw C-D on-resonance (2133 cm$^{-1}$) and off-resonance (2000 cm$^{-1}$) images are shown as references for liver FIG. 9c and intestine FIG. 9d tissues. Scale bar, 10 μm.

FIG. 10 depicts bond-selective SRS imaging of alkynes as nonlinear vibrational tags. For example, FIG. 10a illustrates Spontaneous Raman spectra of HeLa cells and 10 mM EdU solution. Inset: the calculated SRS excitation profile (FWHM 6 cm$^{-1}$) is well fitted within the 2125 cm$^1$ alkyne peak (FWHM 14 cm$^{-1}$, magenta). FIG. 10b illustrates linear dependence of stimulated Raman loss signals (2125 cm$^{-1}$) with EdU concentrations under a 100 s acquisition time. FIG. 10c illustrates the metabolic incorporation scheme for a broad spectrum of alkyne-tagged small precursors. a.u. arbitrary units.

FIG. 12 shows live SRS imaging of de novo synthesis of DNA, RNA, proteomes, phospholipids and triglycerides by metabolic incorporation of alkyne-tagged small precursors. For example, FIG. 12a illustrates Raman spectra of cells incubated with EdU, EU, Hpg, propargylcholine and 17-octadecynoic acid (17-ODYA). FIG. 12b illustrates live HeLa cells incubated with 100 μM EdU alone (alkyne-on) and with 10 mM hydroxyurea (Control). FIG. 12c illustrates time-lapse images of a dividing cell incubated with 100 μM EdU. FIG. 12d illustrates live HeLa cells incubated with 2 mM EU alone (alkyne-on) and with 200 nM actinomycin D (Control). FIG. 12e illustrates pulse-chase imaging of RNA turnover in HeLa cells incubated with 2 mM EU for 12 h followed by EU-free medium. FIG. 12f illustrates live HeLa cells incubated with 2 mM Hpg alone (alkyne-on) and with 2 mM methionine (Control). FIG. 12g illustrates live neurons incubated with 1 mM propargylcholine (alkyne-on). FIG. 12h illustrates live macrophages incubated with 400 μM 17-ODYA (alkyne-on). FIG. 12i, illustrates C. elegans fed with 17-ODYA (alkyne-on). FIG. 12j, illustrates dual-color images of simultaneous EdU (2125 cm$^{-1}$) and propargylcholine (2142 cm$^{-1}$) incorporation. For FIG. 12b, FIG. d, and FIG. 12f, alkyne-off and amide images display the same set of cells as the alkyne-on images; lipid images capture the same cells as control images. Scale bars, 10 μm. Representative images of 10-15 trials. a.u.=arbitrary units.

FIG. 15b EU (for RNA); FIG. 15c Hpg (for protein). Scale bars, 10 μm.

FIG. 16a illustrates fixed NIH3T3 cells after culturing with 0.5 mM propargylcholine for 48 hours. The alkyne-on image shows alkyne-tagged choline distribution. FIG. 16b illustrates treatment of fixed NIH3T3 cells with phospholipase C, which removes Choline head groups of phospholipids only in the presence of calcium. The alkyne-on image shows the strong decrease of incorporated propargylcholine signal, supporting its main incorporation into membrane phospholipids. FIG. 16c illustrates treatment of fixed NIH3T3 cells with phospholipase C in the presence of EDTA (chelating calcium). Propargylcholine signal is retained in the alkyne-on image. FIGS. 16a-16c illustrate images in the same set of cells as in alkyne-on images, the alkyne-off images show a clear background. The amide images display total protein distribution. Scale bars, 10 μm.

FIG. 17a illustrates Raman spectra of a drug cream, Lamisil, containing 1% TH and mouse ear skin tissue. FIGS. 17b-17e illustrate SRS imaging of tissue layers from stratum corneum (z=4 μm) to viable epidermis (z=24 μm), sebaceous gland (z=48 μm) and subcutaneous fat (z=88 μm). To facilitate tissue penetration, DMSO solution containing 1% TH was applied onto the ears of an anesthetized live mouse for 30 min and the dissected ears are imaged afterwards. For all 4 layers: alkyne-on images display TH penetration; alkyne-off images show off-resonant background (The bright spots in FIG. 17d are due to two-photon absorption of red blood cells). The composite images show protein (1655 cm$^{-1}$) and lipid (2845 cm$^{-1}$) distributions. Scale bars, 20 m. a.u. arbitrary units.

FIG. 18 shows in vivo delivery of an alkyne-bearing drug (TH in Lamisil cream, a FDA approved drug cream) into mouse ear. For example, FIGS. 18(a-b) illustrates SRS imaging of the viable epidermis layer (z=20 μm) and the sebaceous gland layer (z=40 μm). For both FIG. 18a and FIG. 18b: illustrates the alkyne-on images display the TH penetration into mouse ear tissues through lipid phase. The composite images show both protein (1655 cm$^{-1}$) and lipid (2845 cm$^{-1}$) distributions. Scale bars, 20 μm.

FIG. 20 shows in FIG. 20a another exemplary synthesis route for a bond-edited compound (alkyne-D-glucose) and in FIG. 20b the spectroscopic characterization of the bond-edited compound in PBS buffer and in mammalian cells.

FIG. 22 shows the results of a competition experiment to confirm the uptake of alkyne-D-glucose. Regular D-glucose is added into cell medium for HeLa cells to compete with the uptake of alkyne-D-glucose. With the increasing concentration of regular D-glucose (10 mM, 50 mM and 100 mM), the alkyne-D-glucose signal decreases (as shown both in images and bar diagrams). When using L-glucose (which cells do not uptake) as competition for alkyne-glucose, the alkyne-D-glucose signal is retained.

FIG. 23 shows alkyne-glucose uptake in both neuronal culture FIG. 23a and brain slices FIG. 23b.

FIG. 25 shows pulse-chase imaging of DNA synthesis (EdU (1) for pulse and EdU-$^{13}$C2 (3) for chase). The merged images show that the two compounds can label two temporally different cells populations for DNA synthesis.

FIG. 28 shows active glucose metabolism in HeLa cells cultured in deuterated glucose medium. For example, FIG. 28a illustrates images after culturing in 0.10% D7-Glucose in EMEM for 48 hrs. FIG. 28b illustrates HeLa cell images after culturing 0.2% D7-Glucose in EMEM for 48 hrs.

FIG. 31 shows SRS imaging of C-D formation using D2O as a metabolic reagent for various of live organisms.

FIG. 32 shows imaging of 13C-phenylalanine labeled proteins for protein turnover. For example, FIG. 32a shows an illustration of a spectroscopic characterization of Raman shift from 1004 cm-1 to 968 cm$^{-1}$ with the labeling of $^{13}$C-phenylalanine, and FIGS. 32(b) and 32c illustrate a time dependent $^{13}$C-phenylalanine labeling, whereas FIG. 32b shows a spectrum and FIG. 32c illustrates SRS images, where the 968 cm-1 signal for $^{13}$C labeled proteins are increasing while the 1004 cm$^{-1}$ signal of old $^{12}$C-proteins are decreasing.

FIG. 33 is a set of exemplary images based on SRS imaging of newly synthesized proteins by metabolic incorporation of deuterium-labeled all amino acids in live HeLa cells. For example, FIG. 33a illustrates Spontaneous Raman spectrum of HeLa cells incubated with a medium containing deuterium-labeled all amino acids for 20 hrs, showing a ~5 times stronger peak at 2133 cm$_{-1}$ than the spectrum in FIG. 2. FIG. 33b illustrates SRS image targeting the central 2133 cm$_{-1}$ vibrational peak of C-D shows a high-contrast image representing newly synthesized proteins. The same intensity scale bar is used here as in FIG. 2. Consistent with previous reports, nascent proteins are distributed with a higher percentage in nucleoli (indicated by arrows) which are the active sites for ribosome biogenesis involving rapid import and degradation of proteins. FIG. 33c illustrates SRS image of the same cells as in FIG. 33b at off-resonance frequency 2000 cm$_{-1}$ is background-free. FIGS. 33d-33f illustrate SRS images of same cells as in FIG. 33b at frequency 1655 cm$_{-1}$ (amide I stretching attributed primarily to proteins); 2845 cm$_{-1}$ ($CH_2$ stretching attributed mainly to lipids) and 2940 cm$_{-1}$ ($CH_3$ stretching attributed mainly to proteins) show the intrinsic distributions of total cellular lipids and proteins.

FIGS. 34g-34i illustrate ratio images between the SRS image at 2133 cm-1 (newly synthesized proteins) and the SRS image at 1655 cm$_{-1}$ (the amide I band from total proteins), representing the relative new protein fraction with subcellular resolution at each time point (5 hrs—FIG. 34g, 12 hrs—FIG. 34h, 20 hrs—FIG. 34i). The bar represents the ratio ranging from low to high. FIG. 34j shows time-lapse SRS images of a live dividing HeLa cell during a 25 min time-course after 20-hour incubation with deuterated all amino acids medium. FIG. 34k illustrates a spontaneous Raman spectrum of HeLa cells incubated with both deuterium-labeled all amino acids and a protein synthesis inhibitor anisomycin (5 μM) for 12 hrs shows the drastic attenuation of the C-D Raman peak at 2133 cm$_{-1}$. FIG. 34l shows an exemplary SRS image of the same sample displays near vanishing signal throughout the whole field of view. FIG. 34m shows, as a control, the image of the same cells at 2940 cm$_{-1}$ confirms that anisomycin does not influence the total protein level.

FIG. 35 is a set of exemplary images based on SRS imaging of newly synthesized proteins by metabolic incorporation of deuterium-labeled all amino acids in live human embryonic kidney (HEK293T) cells. For example, FIG. 35a illustrates the spontaneous Raman spectrum of HEK293T cells incubated with deuterium-labeled all amino acids for 12 hrs shows a 2133 cm$_{-1}$ C-D peak nearly as high as the Amide I (1655 cm$_{-1}$) peak. FIG. 35b shows an exemplary SRS image targeting the central 2133 cm-1 vibrational peak of C-D shows newly synthesized proteins in live HEK293T cells displaying a similar signal level as HeLa cells at 12 hrs (FIG. 4b). FIG. 35c shows, as a comparison, the off-resonant image is still background-free. FIGS. 35d and 35 (e) illustrate multicolor SRS images of intrinsic cell molecules: total proteins (1655 cm$_{-1}$ (FIG. 35d) and lipids (2845 cm$_{-1}$ (FIG. 35e). FIG. 35f illustrates the ratio image between new proteins (2133 cm$_{-1}$) and total proteins (1655 cm$_{-1}$) illustrates a spatial map for nascent protein distribution.

FIG. 36 is a set of exemplary images based on SRS imaging of newly synthesized proteins in both cell bodies and newly grown neurites of neuron-like differentiable mouse neuroblastoma (N2A) cells. During the cell differentiation process by serum-deprivation and 1 μM retinoic acid, deuterium-labeled all amino acids medium is also supplied for 24 hrs. For example, FIG. 36a illustrates SRS images targeting the 2133 cm$_{-1}$ peak of C-D show newly synthesized proteins. FIG. 36 b illustrates SRS images targeting the 2940 cm$_{-1}$ $CH_3$ show total proteins. FIGS. 36c and 36d illustrate zoomed-in images as indicated in the white dashed squares in FIG. 36a and FIG. 36b. FIG. 36e illustrates a ratio image between new protein FIG. 36c and total proteins FIG. 36d. While the starred neurites show high percentage of new proteins, the arrows indicate neurites displaying very low new protein percentage. FIG. 36f Merged image between new protein c (channel 3605) and total proteins in FIG. 36d (channel 3610). Similarly, starred regions show obvious new proteins; while arrows indicate regions that have undetectable new protein signal.

FIG. 37a is a prior art recipe for a mammalian cell culture.

FIG. 37b is an exemplary deuterium-labeled recipe based on the cell culture of FIG. 36;

FIG. 39a is diagram of an exemplary SRS system according to an exemplary embodiment of the present disclosure;

FIGS. 39b-39e are exemplary illustrations of energy outputs according to an exemplary embodiment of the present disclosure;

FIGS. 41a-41j are images taken with the exemplary SRS system according to an exemplary embodiment of the present disclosure;

FIGS. 43a-43c are diagrams of exemplary dye molecules according to an exemplary embodiment of the present disclosure;

FIG. 43d is an exemplary graph of the wavenumbers versus normalized intensity of the exemplary dye molecules from FIGS. 43a-43c according to an exemplary embodiment of the present disclosure.

Figure 5:
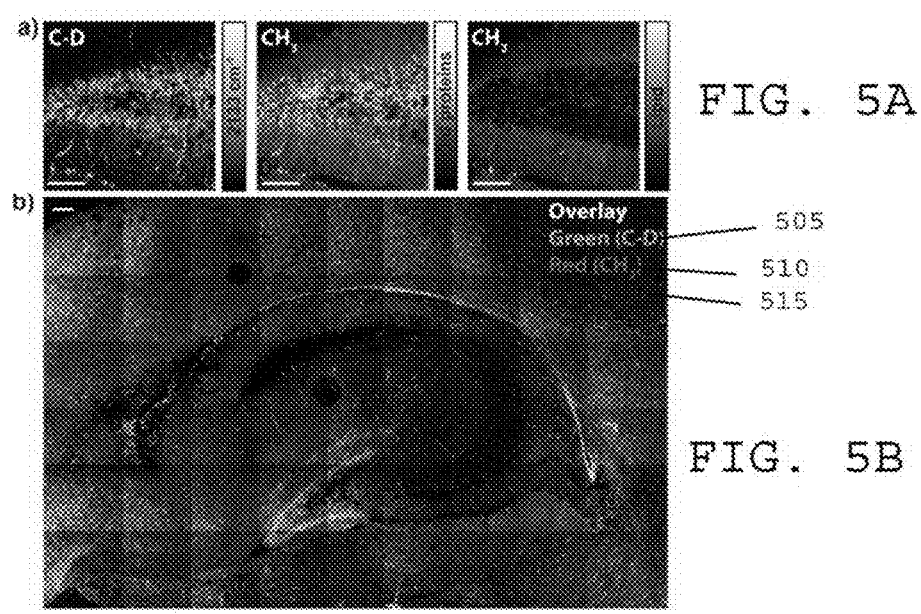
FIG. 5 shows SRS imaging of newly synthesized proteins in live mouse brain tissues. For example.

Throughout the drawings, the same reference numerals and characters, unless otherwise stated, are used to denote like features, elements, components or portions of the illustrated exemplary embodiments. Moreover, while the present disclosure will now be described in detail with reference to the figures it is done so in connection with the illustrative exemplary embodiments and is not limited by the particular exemplary embodiments illustrated in the figures, and provided in the appended claims.

DETAILED DESCRIPTION OF EXEMPLARY EMBODIMENTS

The following detailed description is presented to enable any person skilled in the art to make and use the present disclosure. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present disclosure is not intended to be limited to the exemplary embodiments shown, but is to be accorded the widest possible scope consistent with the principles and features disclosed herein.

As used herein, the term "Raman scattering" refers to a spectroscopic technique used to observe vibrational, rotational, and other low-frequency modes in a system. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system. A variety of optical processes, both linear and nonlinear in light intensity dependence, are fundamentally related to Raman scattering. As used herein, the term "Raman scattering" includes, but is not limited to, "stimulated Raman scattering" (SRS), "spontaneous Raman scattering", "coherent anti-Stokes Raman scattering" (CARS), "surface-enhanced Raman scattering" (SERS), "Tip-enhanced Raman scattering" (TERS) or "vibrational photoacoustic tomography".

The exemplary system, method and computer accessible medium, according to an exemplary embodiment of the present disclosure, can use alkyne as a vibrational tag coupled with narrow-band stimulated Raman scattering microscopy ("SRS") for the detection of small molecules inside biological systems. The use of alkyne as a vibrational tag (e.g. a Raman tag) offers a large Raman cross-section enabling sensitive detection (See, e.g., References 13; 14). Additionally, the alkyne Raman peak can exhibit a narrow spectral width for the specific detection, which can reduce the probability of overlapping with other tags. Furthermore, the Raman peak of alkyne can lay exactly in the cell-silent region in the cell spontaneous Raman spectrum, bypassing the complex interference from vast pool of biomolecules in the fingerprint region. (See, e.g., FIG. 1b).

The exemplary SRS can be a sensitive vibrational imaging microscopy. By harnessing Einstein's stimulated emission process, the exemplary SRS can employ two-laser excitation (e.g., temporally and spatially overlapped Pump and Stokes lasers), boosting up the transition rate about 7 orders of magnitude as compared to the traditional spontaneous Raman microscopy, the transition process of which can be intrinsically weak (e.g., 10 to 12 orders of magnitude slower than fluorescence). (See, e.g., References 6; 8; 15). The exemplary SRS can be a bond-selective procedure with high specificity, in contrast with the spontaneous Raman imaging which can be a spectrum-based method. Instead of spreading the energy to the whole spectrum as in the spontaneous Raman imaging, the exemplary narrow-band SRS can focus its energy to the vibrational transition of a specific bond. A 6-ps pulse width can be chosen for both SRS pump and stokes lasers to achieve a spectral resolution of 5 $cm^{-1}$ for the detection of alkyne. The spectral width of the excitation profile from two combined lasers can be calculated to be 8 $cm^{-1}$, which can fit well within the spectral width of alkyne Raman peak that can be 14 $cm^{-1}$. (See, e.g., FIG. 1b). Hence, the exemplary laser pulse width can be long enough that all the laser energy can be used to specifically detect alkyne without energy waste, but short enough that the two-photon efficiency can be maintained since the exemplary SRS can depend on a nonlinear process.

The exemplary SRS signal can offer linear concentration dependence to the analyte without non-specific background. Compared to a previously known nonlinear vibrational imaging procedure such coherent anti-Stokes Raman scattering ("CARS") microscopy, which suffers from spectral distortion, unwanted non-resonant background, non-straightforward concentration dependence and coherent image artifact, the exemplary SRS can exhibit straightforward image interpretation and quantification without complications from non-resonant background and phase-matching conditions (See, e.g., References 7; 8; 16). Besides the above-mentioned advantages, SRS can also have its own distinctive characters as an imaging procedure. For example, SRS can be immune to fluorescence background as compared to spontaneous Raman microscopy that can suffer from large fluorescence background. In addition, SRS, as a nonlinear process, can offer intrinsic 3D sectioning capability. Moreover, by adopting near-infrared excitation, SRS can offer deeper penetration depth and less photo-toxicity, which can be well suited for imaging live cells, tissues and animals. Recently, narrow-band SRS has achieved unprecedented sensitivity down to approximately 1000 retinoic acid molecules and up to video rate imaging speed in vivo. (See, e.g., Reference 17).

Alkyne can be a metabolic labeling tag in fluorescence microscopy utilizing click-chemistry with azide-linked fluorescent tags (See, e.g., References 18-23). Unfortunately, this type of click-chemistry based fluorescence detection usually requires non-physiological fixation and subsequent dye staining and washing. The exemplary Raman detection, in contrast, does not have such requirements, since it can directly image vibrational modes of alkyne, bypassing the subsequent additional processes.

All of the above applications can show the universal and distinct advantage of the exemplary SRS coupled with alkyne tags to image the small molecule metabolites dynamics and drug distributions in the live cells, organisms and animals with minimum perturbation and high specificity and sensitivity, extending the repertoire of reporters for biological imaging beyond fluorophores.

Method for Obtaining Biological Information in a Living Cell or a Living Organism with Bond-Edited Compounds One aspect of the present disclosure relates to a method for obtaining biological information in a living cell or a living organism with bond-edited compounds using Raman scattering. The method comprises the steps of introducing an effective amount of one or more bond-edited compounds into a live cell or a living organism, and detecting a vibrational tag in the cell or organism with Raman scattering. In some exemplary embodiments, the Raman scattering is SRS.

The term "biological information" as used herein, refers to spatial distribution of the targeted molecules, such as one-dimensional line, or two-dimensional or three-dimensional images, and non-imaging information, such as a simple signal intensity or local spectrum on a single location or its time dependence.

As used herein, the term "bond-edited compounds" refers to compounds having one or more chemical bond that may serve as a vibrational tag for detection by Raman scattering. Examples of chemical bond that may serve as a vibrational tag include, but are not limited to, carbon-carbon triple bond, carbon-nitrogen triple bond, azide bond, carbon-deuterium bond, phenol ring, $^{13}$C modified carbon-carbon triple bond, $^{13}$C modified carbon-nitrogen triple bond, $^{13}$C modified azide bond, $^{13}$C modified carbon-deuterium bond, $^{13}$C modified phenol ring and combinations thereof.

As used herein, the term "effective amount" refers to an amount that, when introduced into a live cell or organism, is sufficient to reach a working concentration needed for SRS imaging. The "effective amount" would vary based on the type of bond-edited compound, as well as the cells or organisms that the bond-edited compound is introduced into. In some embodiments, an "effective amount" of a bond-edited compound is the amount that is sufficient to reach an in vivo concentration of 1 µM to 100 mM, 3 µM to 30 mM, 10 µM to 10 mM, 100 µM to 1 mM, 10 µM to 1 mM or 10 µM to 100 µM in a target cell or organ. In some embodiments, an "effective amount" of a bond-edited compound comprising a triple bond is the amount that is sufficient to reach an in vivo concentration of 1 µM to 10 mM, 3 µM to 3 mM, 1 µM to 1 mM or 30 µM to 300 µM. In some embodiments, an "effective amount" of a bond-edited compound comprising a triple bond is the amount that is sufficient to reach an in vivo concentration of about 100 µM. In other embodiments, an "effective amount" of a bond-edited compound comprising a C-D bond is the amount that is sufficient to reach an in vivo concentration of 10 µM to 100 mM, 30 µM to 30 mM, 100 µM to 10 mM or 300 µM to 3 mM. In some embodiments, an "effective amount" of a bond-edited compound comprising a C-D bond is the amount that is sufficient to reach an in vivo concentration of about 1 mM.

In some exemplary embodiments, the bond-edited compounds are small molecules. As used herein, the term "small molecules" refers to low molecular weight organic compound having a molecular weight of 1000 daltons or less. In some exemplary embodiments, the small molecules have a size on the order of $10^{-9}$ m. Examples of small molecules include, but are not limited to, water, ribonucleosides, ribonucleotides, deoxyribonucleoside, deoxyribonucleotide, amino acids, peptides, choline, monosaccharides, disaccharides, fatty acids, glucose, adenosine triphosphate, adenosine diphosphate, cholesterol, neurotransmitters, secondary messengers, and chemical drugs.

In some exemplary embodiments, said bond-edited compound contains one, two, three, four, five, six, seven, eight, nine, ten or more vibrational tags. The vibrational tags may be the same type of tags or a mixture of one or more different tags.

In some exemplary embodiments, said vibrational tag is an alkyne tag. In other exemplary embodiments, said vibrational tag is an azide tag. In still other exemplary embodiments, said vibrational tag is an isotope label. In a further exemplary embodiment, said isotope label is a carbon-deuterium tag. In yet still other exemplary embodiments, said vibrational tag is a combination of an alkyne tag and a carbon-deuterium tag.

In particular exemplary embodiments, said at least one vibrational tag comprises at least one vibrational tag selected from the group consisting of —C≡C—, —C≡N, —N≡N≡N, —C≡C≡C≡C—, —C≡C≡C≡N, —C-D, and —C≡C-D.

In a further exemplary embodiment, the vibrational comprises at least one $^{13}$C atom or one deuterium atom.

In some exemplary embodiments, the bond-edited compound is an amino acid.

In further exemplary embodiments, the amino acid is an essential amino acid.

In a still further exemplary embodiment, the essential amino acid is selected from the group consisting of histidine, isoleucine, leucine, lysing, methionine, phenylalanine, threonine, tryptophan and valine.

In other exemplary embodiments, the bond-edited compound is a nucleoside or a nucleotide.

In still other exemplary embodiments, the bond-edited compound is a fatty acid.

In still other exemplary embodiments, the bond-edited compound is a monosaccharide or a disaccharide. In a further exemplary embodiment, the bond-edited compound is glucose, a glucose derivative or propargyl glucose.

In still other exemplary embodiments, the bond-edited compound is a pharmaceutical agent, such as an anti-cancer agent, anti-inflammatory agent, anti-bacterial agent, anti-fungal agent and anti-viral agent.

In still other exemplary embodiments, the bond-edited compound is a cytokine or chemokine.

In some exemplary embodiments, the bond-edited compound is EU-$^{13}C_2$ having a molecular structure of formula 13:

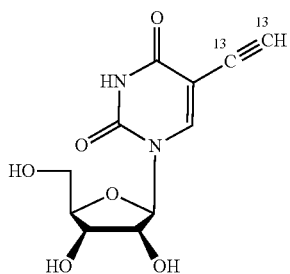

(13)

In some exemplary embodiments, the bond-edited compound is EdU-$^{13}C_2$ having a molecular structure of formula 3:

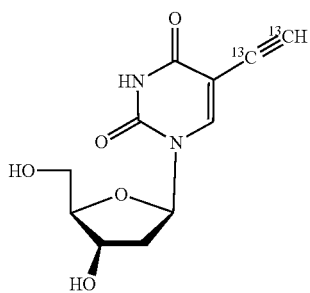

3

In some exemplary embodiments, the bond-edited compound is EdU-$^{13}C$ having a molecular structure of formula 2:

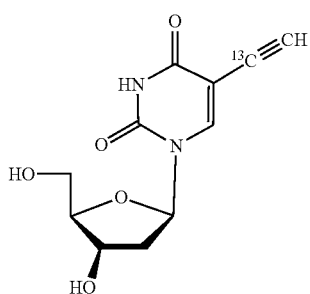

2

In some exemplary embodiments, the bond-edited compound is EdU-$^{13}C'$ having a molecular structure of formula 14:

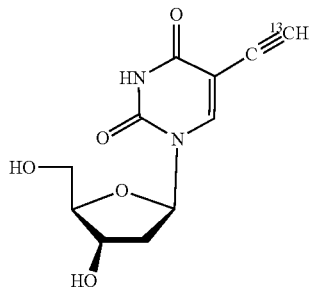

(14)

In some exemplary embodiments, the bond-edited compound is alkyne-D-glucose having a molecular structure of formula S3:

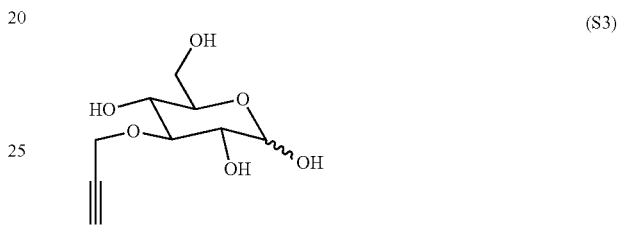

(S3)

In some exemplary embodiments, the bond-edited compound is metabolized in the living cell or organism and the vibrational tag is transferred from the bond-edited compound to a down-stream metabolite of the bond-edited compound (See, e.g., FIGS. 28-31).

In still other exemplary embodiments, the method comprises introducing into a live cell a mixture of bond-edited compounds that imaging with Raman scattering at two or more different wavelengths. In some related exemplary embodiments, the Raman scattering is SRS.

In still other exemplary embodiments, the method comprises introducing into a live cell a mixture of different bond-edited compounds that allow multiple color imaging with Raman scattering. In some related exemplary embodiments, the Raman scattering is SRS. In a particular exemplary embodiment, the mixture of different bond-edited compounds comprises EU-$^{13}C_2$, EdU-$^{13}C$ and 17-ODYA.

In some exemplary embodiments, the two or more bond-edited compounds target the same cellular component but at different time period (See, e.g., FIG. 25).

In still other exemplary embodiments, the method comprises introducing into a living cell a mixture of different bond-edited compounds that target different cellular components.

In still other exemplary embodiments, the method comprises introducing into a living organism a mixture of different bond-edited compounds that target different types of cells in the living organism.

In still other exemplary embodiments, the method comprises introducing into a living organism a mixture of different bond-edited compounds carrying different vibrational tags, and detecting the different vibrational tags with Raman scattering using a linear combination algorithm. In some related exemplary embodiments, the Raman scattering is SRS.

Method for Making Bond-Edited Compounds

Another exemplary aspect of the present disclosure relates to a method for making a bond-edited compound.

Figure 19:
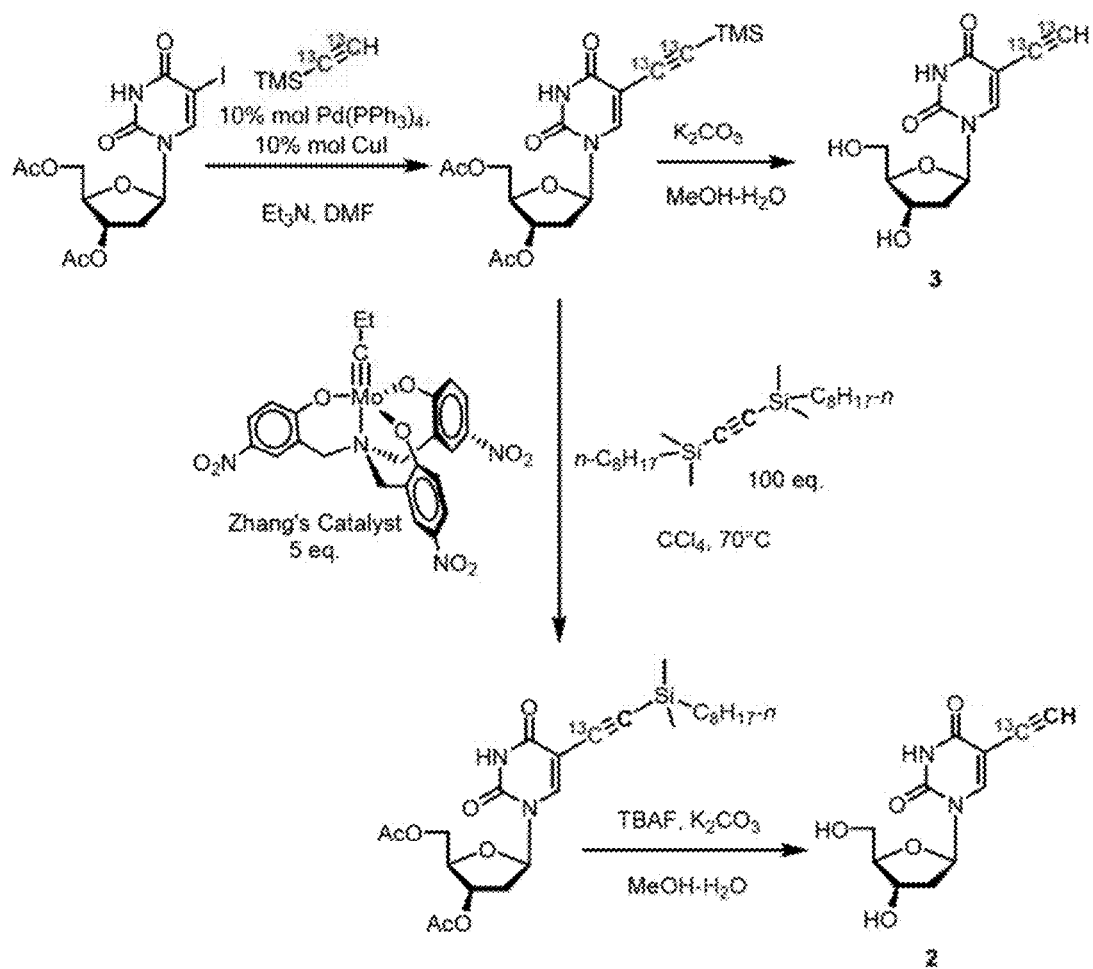
FIG. 19 shows an exemplary synthesis route for a bond-edited compound.
Figure 21:
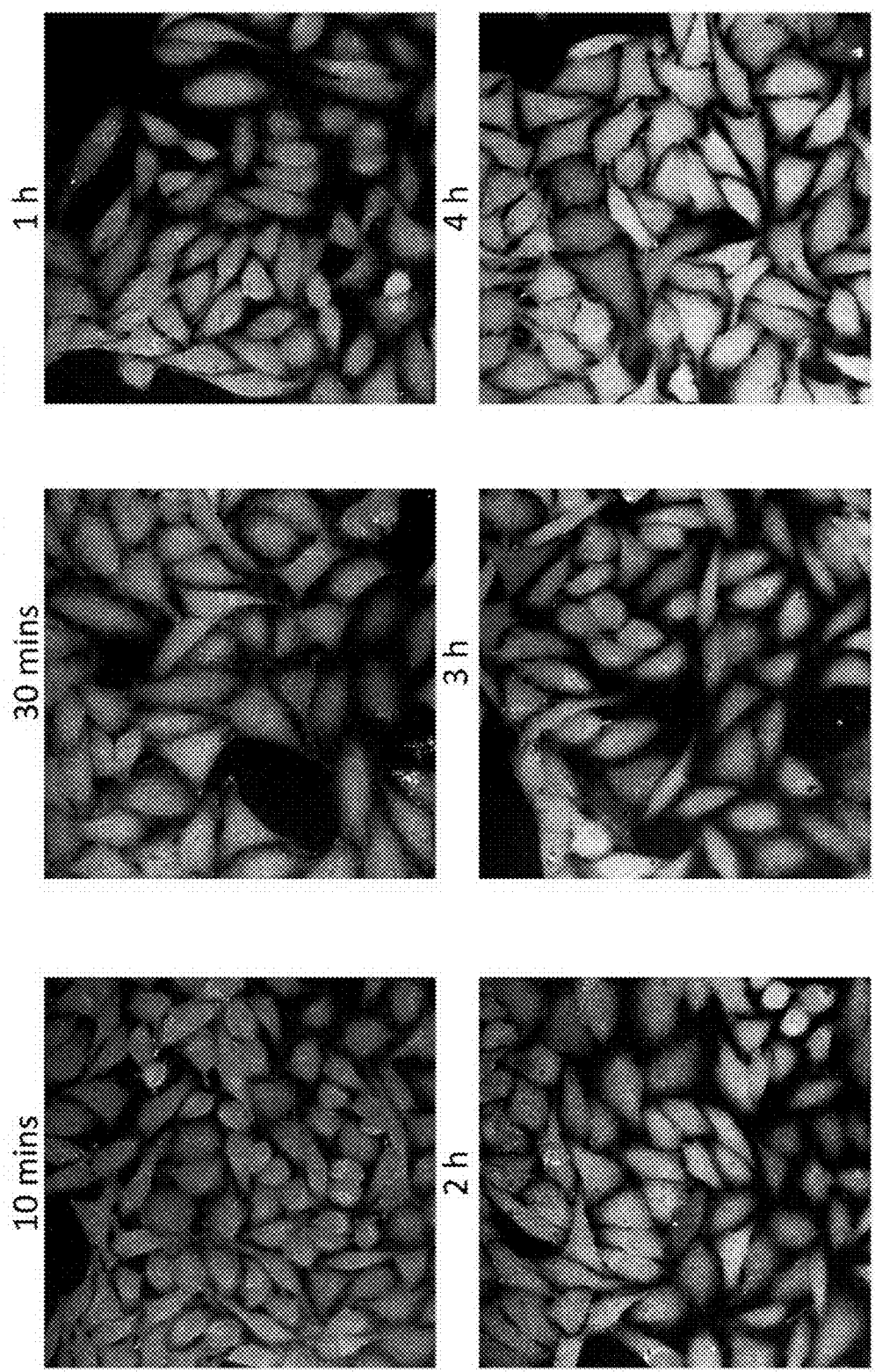
FIG. 21 shows time-dependent alkyne-D-glucose (32 mM) uptake in live HeLa cells at 10 min, 30 min, 1 h, 2 h, 3 h and 4 h time points. The glucose signal inside mammalian cells is increasing over time.
Figure 24:
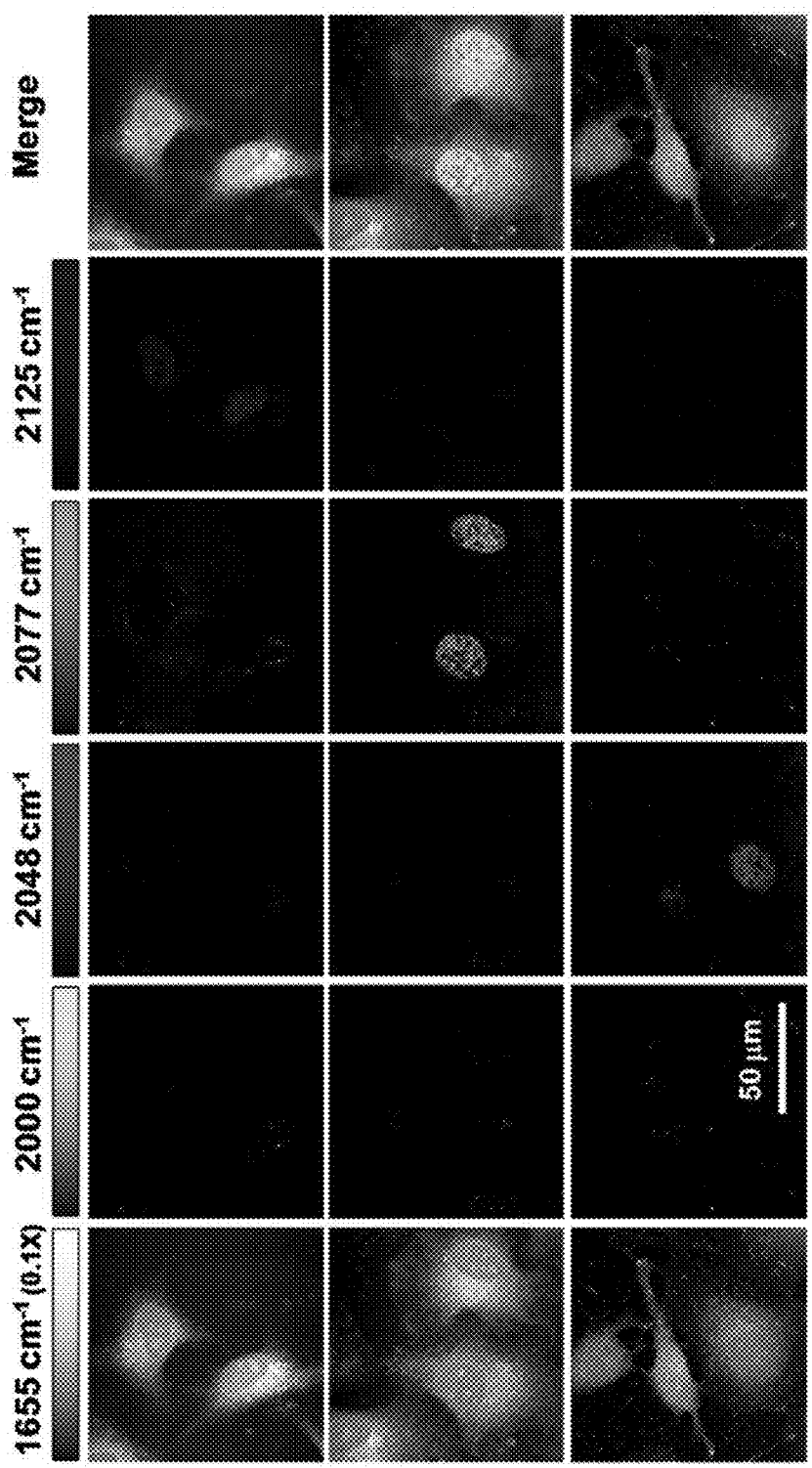
FIG. 24 shows multicolor imaging of DNA synthesis with EdU (1), EdU-$^{13}$C (2) and EdU-$^{13}$C2 (3).
Figure 26:
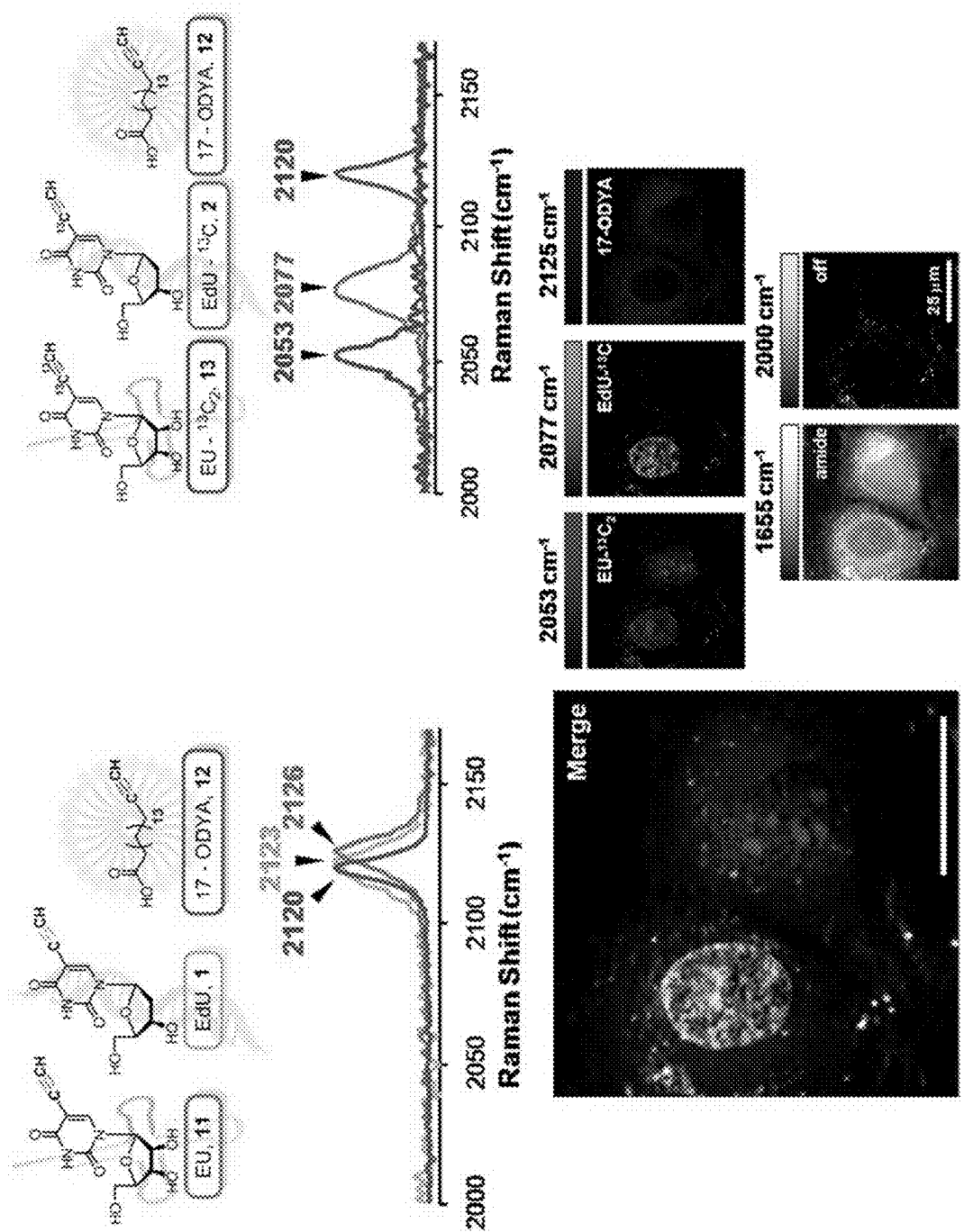
FIG. 26 shows simultaneous three-color chemical imaging using alkyne probes for DNA synthesis (EdU-$^{13}$C (2) at 2077 cm-1) and RNA synthesis (EU-$^{13}$C2 (13) at 2053 cm-1 and 17-ODYA (12) at 2125 cm-1).
Figure 27:
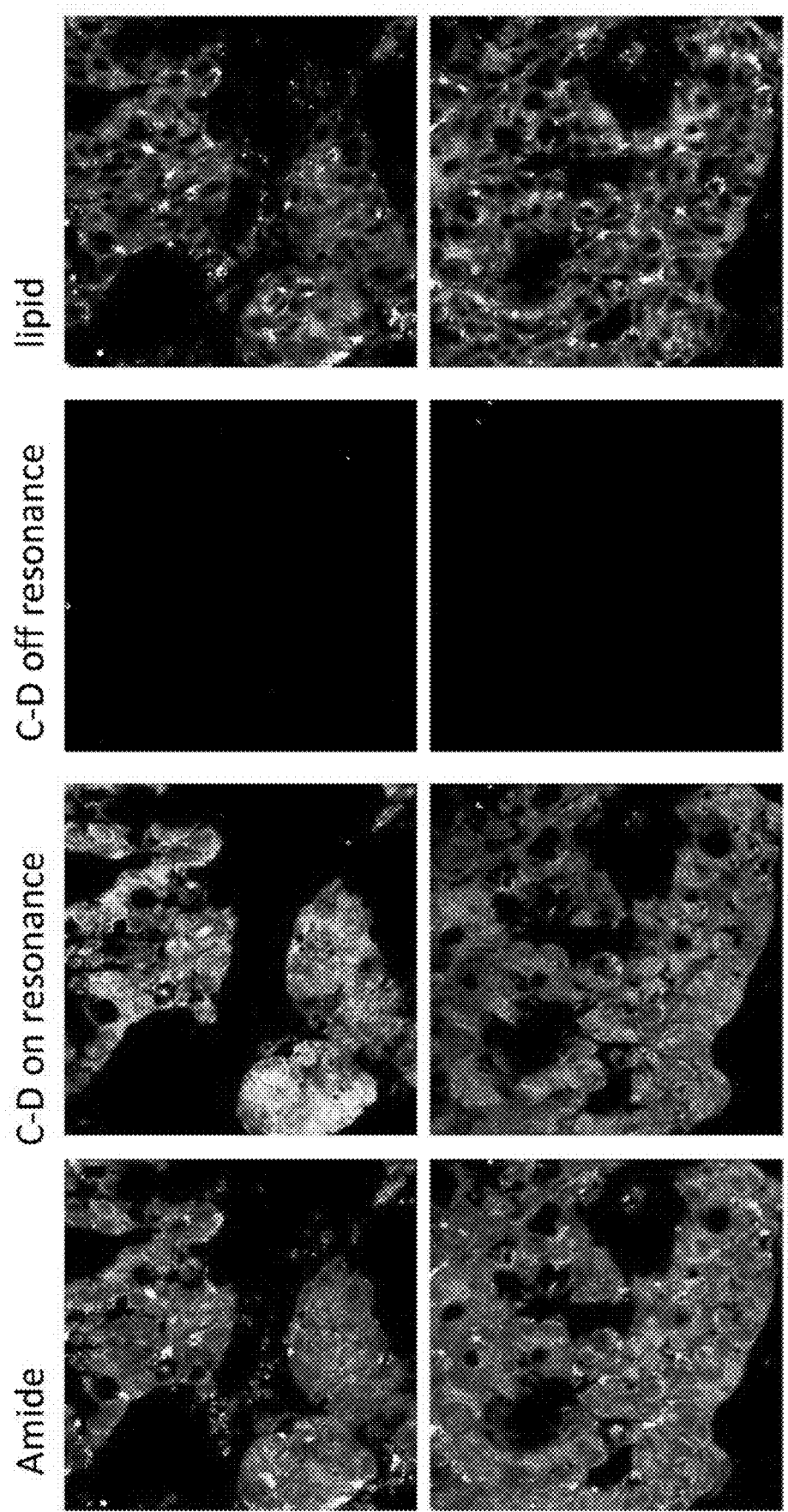
FIG. 27 shows images of subcutaneous colon cancer. Subcutaneous colon cancer was grown for 15 days in mice, dissected out and cultured ex vivo in deuterated amino acids containing medium for 47 h (400 um thick). Live image of the tumors shows intensive protein synthesis activity.
Figure 29:
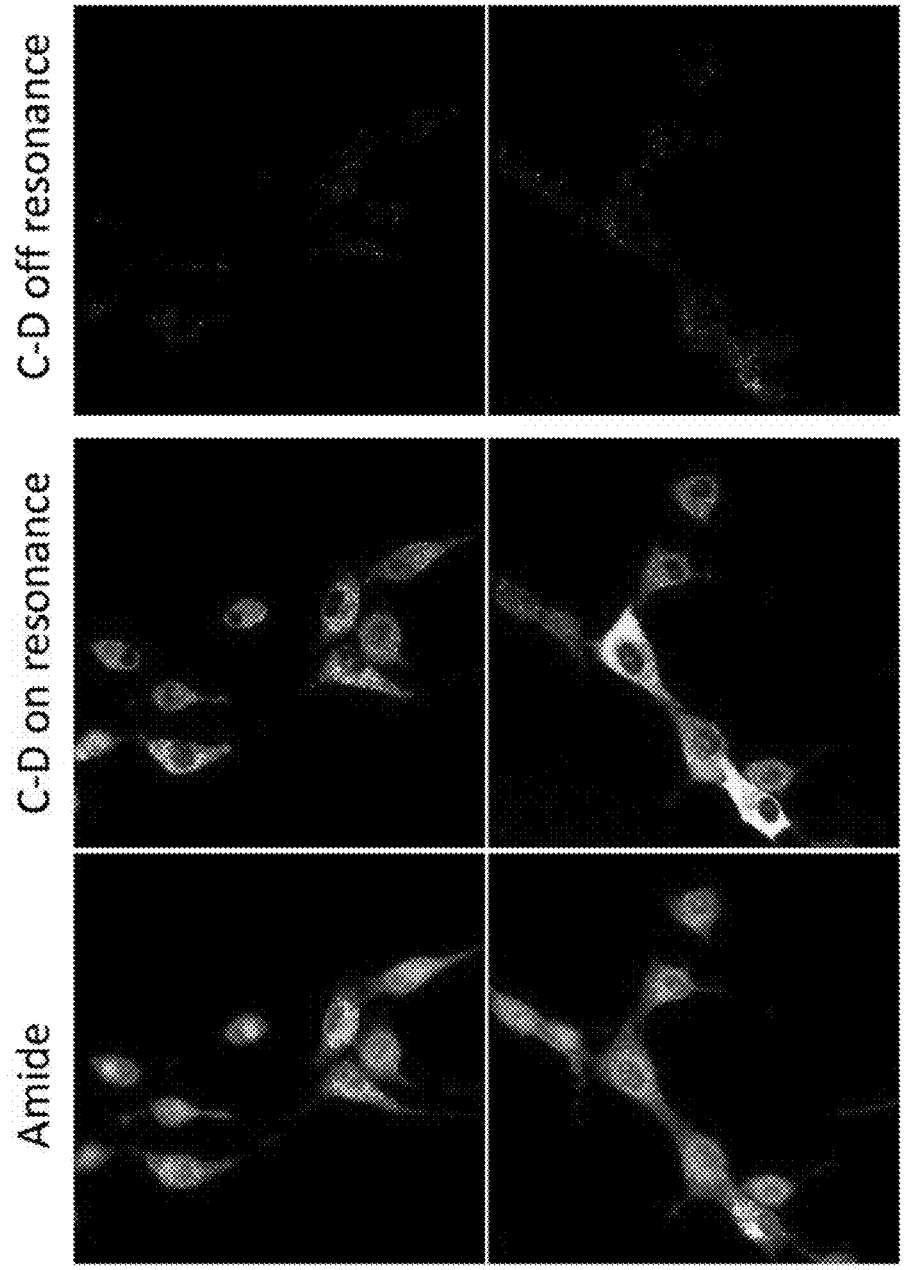
FIG. 29 shows active glucose metabolism in tumor cell line U87MG cultured in deuterated glucose medium (0.1% D7-Glucose in EMEM) for 48 hrs.
Figure 30:
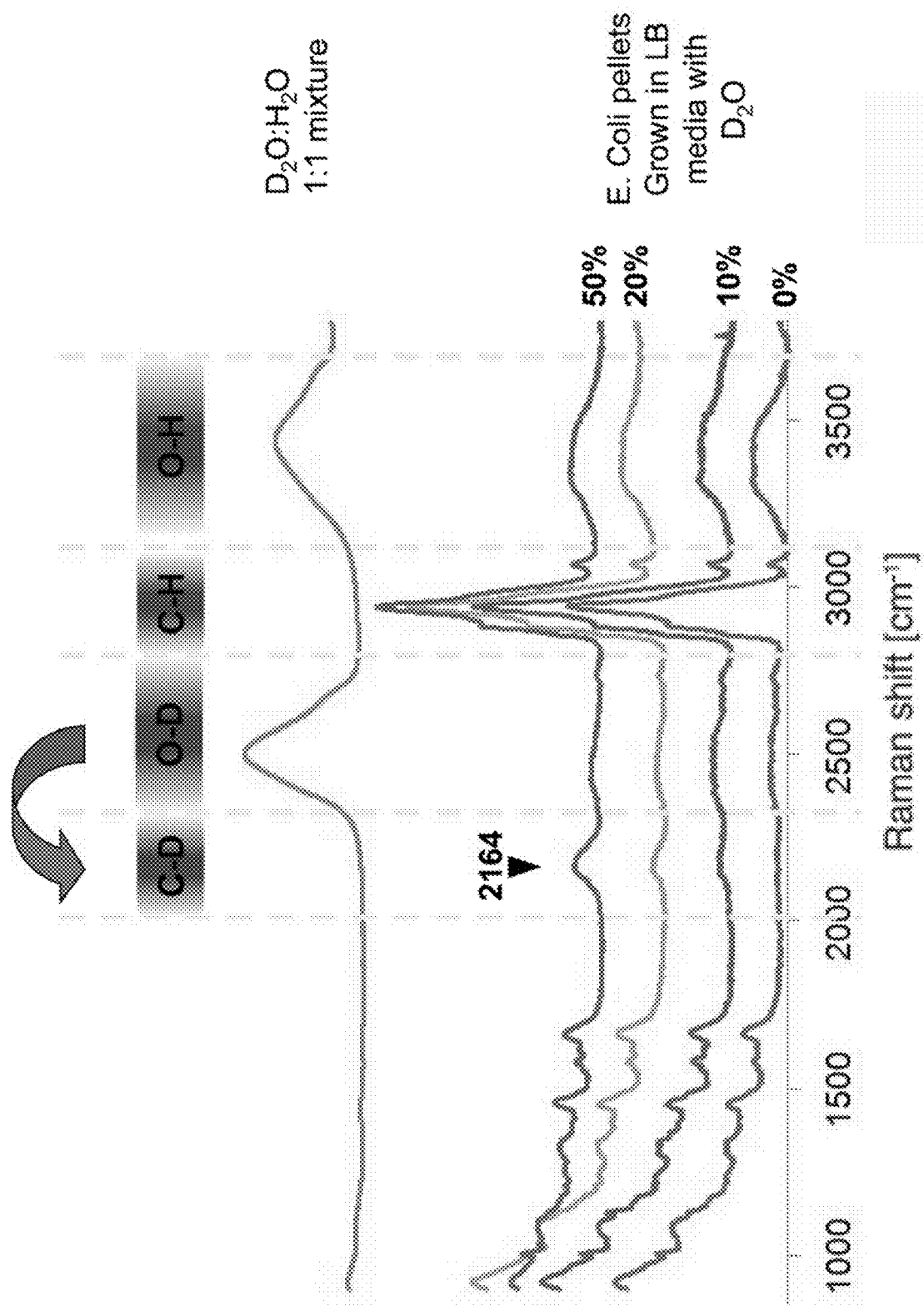
FIG. 30 shows the detection of D2O as a labeling reagent of the metabolism with stimulated Raman scattering.

In one exemplary embodiment, the bond-edited compound is synthesized by the route illustrated in FIG. 19. In another exemplary embodiment, the bond-edited compound is synthesized by the route illustrated in FIG. 20.

Method of Detecting Disease Conditions

Another exemplary aspect of the present disclosure relates to a method for detecting a disease condition in a subject, comprising: administering to said subject a composition comprising a bond-edited compound targeting a disease tissue or pathogen, and detecting said bond-edited compound by Raman scattering.

In some exemplary embodiments, the subject is a mammal. Exemplary mammal subjects for use in accordance with the methods described herein include humans, monkeys, gorillas, baboons, zoo animals and domesticated animals, such as cows, pigs, horses, rabbits, dogs, cats, goats and the like.

In some exemplary embodiments, the disease condition is cancer.

In some exemplary embodiments, the disease condition is a neurodegenerative disease. In further exemplary embodiments, the neurodegenerative disease is selected from the group consisting of amyotrophic lateral sclerosis, Parkinson's, Alzheimer's and Huntington's.

In some exemplary embodiments, the disease condition is an inflammatory disease.

In some exemplary embodiments, the disease condition is a microbial infection.

In some exemplary embodiments, the disease condition is a bacterial infection.

In some exemplary embodiments, the disease condition is a viral infection.

In some exemplary embodiments, the disease condition is a fungal infection.

In some exemplary embodiments, the pathogen comprises bacteria.

Method for Monitoring Treatment for a Disease Condition

Another exemplary aspect of the present disclosure relates to a method for monitoring treatment for a disease condition. The method comprises administering to said subject a composition comprising a bond-edited compound and detecting said bond-edited compound by SRS at a first time point, further administering to said subject said composition comprising a bond-edited compound and detecting said bond-edited compound by Raman scattering at a second time point, and comparing images obtained at the two time points.

In some exemplary embodiments, the first time point is a time point that is about or prior to the initiation of a treatment and the second time point is a time point that is after the initiation of the treatment.

In other exemplary embodiments, the first time point and the second time point are two time points during the course of a treatment.

In some exemplary embodiments, the treatment is a treatment for cancer.

In other exemplary embodiments, the treatment is a treatment for an inflammatory disease.

In other exemplary embodiments, the treatment is a treatment for a neurodegenerative disease.

Method for Screening an Agent

Another exemplary aspect of the present disclosure relates to a method for screening an agent. The method comprises administering said agent and at least one bond-edited compound to a live cell or organism, detecting the bond-edited compound in the live cell or organism using Raman scattering, and selecting a candidate agent based on one or more predetermined criteria, such as the uptake, accumulation, trafficking, or degradation of the said bond-edited compound in the said live cell or organism.

In some exemplary embodiments, the candidate agent is an anti-cancer drug.

In some exemplary embodiments, the bond-edited compound is selected from the group consisting of amino acid, nucleic acid, ribonucleic acid and glucose derivatives.

In some exemplary embodiments, the candidate agent is a skin regenerating agent.

In some exemplary embodiments, the candidate agent is a cosmetic agent.

Method for Tracing a Cellular Process in a Live Cell with Raman Scattering

Another exemplary aspect of the present disclosure relates to a method for tracing a cellular process in a live cell with Raman scattering. The method comprises introducing into a live cell a bond-edited compound, and following the physical movement or the chemical reaction or the biological interaction of the bond-edited compound within the cell by SRS.

In some exemplary embodiments, the cellular processes are selected from the group consisting of DNA replication, RNA synthesis, protein synthesis, protein degradation, glucose uptake and drug uptake.

Composition for Labeling Cells with Bond-Edited Compounds

Another exemplary aspect of the present disclosure relates to a composition for labeling a target cell with at least one bond-edited compound. In some exemplary embodiments, the composition is a culture medium comprising at least one bond-edited compound containing at least one vibrational tag. The at least one bond-edited compound may be selected based on the type of the target cell or a target component(s) within the target cell.

In some exemplary embodiments, the culture medium comprises a plurality of amino acids, wherein over 20%, 30%, 40%, 50%, 60%, 70%, 80%, 90% of the amino acids are tagged with one or more vibrational tag. In other exemplary embodiments, the culture medium comprises a plurality of amino acids, wherein all amino acids are tagged with one or more vibrational tag.

In some exemplary embodiments, the culture medium comprises two, three, four, five, six, seven, eight, nine, ten or more different bond-edited compounds.

Device for Imaging a Living Cell or a Living Organism with Bond-Edited Compounds Another exemplary aspect of the present disclosure relates to a device for imaging bond-edited compounds by Raman scattering. The device comprises a first single-wavelength laser source that produces a pulse laser beam of a first wavelength, a second single-wavelength laser source that produces a pulse laser beam of a second wavelength, a modulator that modulates either the intensity or the frequency or the phase or the polarization or the combination of the above of the pulse laser beam of one of the first or second laser source, a photodetector that is capable of detecting SRS or CARS or spontaneous Raman scattering or the combination of the above from a biosample, and a computer.

In some exemplary embodiments, the energy difference between the photons produced by the first laser radiation and the photon produced by the second laser radiation matches with the energy of the vibrational transitions of the targeted vibrational tags. Photodetector of SRS detects part or all of the first laser beam or the second laser beam. The output of the photodetector (which could be a photodiode) is further processed by a lock-in amplifier or a resonant circuit.

Another exemplary aspect of the present disclosure relates to an apparatus for providing radiation to at least one structure, comprising: a radiation providing arrangement which is configured to provide a pump radiation and a stokes radiation, each at a fixed wavelength, whose energy difference is between about 2000 and 2500 wavenumbers.

In some exemplary embodiments, the radiation providing arrangement is a laser source.

The following examples are put forth so as to provide those of ordinary skill in the art with a complete disclosure and description of how to carry out the method of the present disclosure and is not intended to limit the scope of the invention. Efforts have been made to ensure accuracy with respect to numbers used (e.g., amounts, temperature, etc.), but some experimental error and deviation should be accounted for. Unless indicated otherwise, parts are parts by weight, molecular weight is weight average molecular weight, temperature is in degrees Centigrade and pressure is at or near atmospheric.

EXAMPLES

Example 1: In Vitro and In Vivo Labeling with Deuterium Tags

In the examples described below, three major technical advances are being implemented, together with a series of biological applications on complex tissues and model animals in vivo (FIG. 1a). First, we optimized the chemical composition of the deuterated culture medium that achieved much higher deuterium labeling efficiency, and improved imaging sensitivity and speed of our SRS instrumentation. These optimizations allow us to demonstrate time-lapse imaging of protein synthesis dynamics within single live cells. Second, we successfully imaged protein degradation in live HeLa cells by targeting Raman peak of methyl group ($CH_3$) for the pre-existing protein pools and then employing a recently developed linear combination algorithm on measured SRS images at 2940 $cm^{-1}$ and 2845 $cm^{-1}$ channels. Third, inspired by the classic pulse-chase analysis of complex protein dynamics, two-color pulse-chase imaging was accomplished by rationally dividing D-AAs into two structurally different sub-sets that exhibit resolvable vibrational modes, as demonstrated by tracking aggregate formation of mutant huntingtin (mHtt) proteins. Finally, going beyond the cellular level to visualizing more complex tissues and animals in vivo, we imaged the spatial distribution of newly synthesized proteins inside live brain tissue slices and in both developmental embryonic zebrafish and mice (FIG. 1b). Taken together, these technical advances and biological applications demonstrate SRS microscopy coupled with metabolic labeling of D-AAs as a comprehensive and generally applicable imaging platform to evaluate complex protein metabolism with high sensitivity, resolution and biocompatibility in a broad spectrum of live cells, tissues and animals.

Exemplary Materials and Methods

Stimulated Raman scattering microscopy. An integrated laser (picoEMERALD with custom modification, Applied Physics & Electronics, Inc.) was used as the light source for both Pump and Stokes beams. Briefly, picoEMERALD provides an output pulse train at 1064 nm with 6 ps pulse width and 80 MHz repetition rate, which serves as the Stokes beam. The frequency-doubled beam at 532 nm is used to synchronously Seed a picosecond optical parametric oscillator (OPO) to produce a mode-locked pulse train (the idler beam of the OPO is blocked with an interferometric filter) with 5~6 ps pulse width. The wavelength of the OPO is tunable from 720 to 990 nm, which serves as the Pump beam. The intensity of the 1064 nm Stokes beam is modulated sinusoidally by a built-in electro-optic modulator (EOM) at 8 MHz with a modulation depth of more than 95%. The Pump beam is spatially overlapped with the Stokes beam with a dichroic mirror inside picoEMERALD. The temporal overlap between Pump and Stokes pulse trains is ensured with a built-in delay stage and optimized by the SRS signal of pure dodecane liquid.

Pump and Stokes beams are coupled into an inverted laser-scanning microscope (FV1200MPE, Olympus) optimized for near IR throughput. A 60× water objective (UPlanAPO/IR, 1.2 N.A., Olympus) with high near IR transmission is used for all cellular level imaging, and a 25× water objective (XLPlan N, 1.05 N.A., MP, Olympus) with both high near IR transmission and large field of view is used for brain tissue and in vivo imaging. The Pump/Stokes beam size is matched to fill the back-aperture of the objective. The forward going Pump and Stokes beams after passing through the sample are collected in transmission with a high N.A. condenser lens (oil immersion, 1.4 N.A., Olympus), which is aligned following Kohler illumination. A telescope is then used to image the scanning mirrors onto a large area (10 mm by 10 mm) Si photodiode (FDS1010, Thorlabs) to descan beam motion during laser scanning. The photodiode is reverse-biased by 64 V from a DC power supply to increase both the saturation threshold and response bandwidth. A high O.D. bandpass filter (890/220 CARS, Chroma Technology) is used to block the Stokes beam completely and transmit the Pump beam only. The output current of the photodiode is electronically pre-filtered by an 8-MHz band-pass filter (KR 2724, KR electronics) to suppress both the 80 MHz laser pulsing and the low-frequency contribution due to laser scanning across the scattering sample. It is then fed into a radio frequency lock-in amplifier (HF2LI, Zurich instrument) terminated with 50Ω to demodulate the stimulated Raman loss signal experienced by the Pump beam. The R-output of the lock-in amplifier is fed back into the analog interface box (FV10-ANALOG) of the microscope.

For HeLa cell imaging and brain tissue imaging, the time constant of the lock-in amplifier is set for 8 µs, and the images are acquired by a 12.5 µs pixel dwell time, corresponding to 3.3 s for a 512-by-512 pixel frame. For neurons and in vivo imaging of embryonic zebrafish and mice livers and intestines, the time constant is set to be 20 µs, and the images are acquired by a 40 µs of pixel dwell time, corresponding to 10.5 s for a 512-by-512 pixel frame. Laser powers after 60× IR objective used for cell imaging are: 100 mW for modulated Stokes beam and 112 mW for the Pump beam at 2133 $cm^{-1}$, 2000 $cm^{-1}$ and 1655 $cm^{-1}$ channels; 50 mW for modulated Stokes beam and 56 mW for Pump beam at 2940 $cm^{-1}$ and 2845 $cm^{-1}$ channels. Laser powers after 25× objective used for tissue and in vivo imaging are: 134 mW for modulated Stokes beam; 120 mW for the Pump beam of 2133 $cm^{-1}$, 2000 $cm^{-1}$ and 1655 $cm^{-1}$ channels; 67 mW for modulated Stokes beam and 60 mW for Pump beam at 2940 $cm^{-1}$ and 2845 $cm^{-1}$ channels.

Metabolic incorporation of deuterated amino acids. For HeLa cells: cells are Seeded on a coverslip in a petri-dish with 2 mL of regular medium for 20 h, and then replaced with D-AA medium (or group I and group II D-AA media) for designated amount of time. The coverslip is taken out to make an imaging chamber filled with PBS for SRS imaging.

For hippocampal neurons, the dissociated neurons from newborn mice are Seeded for 10 days in regular Neurobasal A medium, and then replaced with the corresponding D-AA medium for designated amount of time before imaging. For organotypic brain slice, 400 μm thick, P10 mouse brain slices are cultured on Millicell-CM inserts (PICM03050, millipore) in 1 mL CD-MEM culture medium for 2 h, and then change to in 1 mL CD-neurobasal a culture medium for another 28 h before imaging. For detailed recipe of D-AA media and in vivo labeling procedure in zebrafish and mice. (See Supporting Information). The experimental protocol for in vivo mice experiments (AC-AAAG2702) and zebrafish experiments (AC-AAAD6300) were approved by Institutional Animal Care and Use Committee at Columbia University.

Spontaneous Raman spectroscopy. The spontaneous Raman spectra were acquired using a laser Raman spectrometer (inVia Raman microscope, Ranishaw) at room temperature. A 27 mW (after objective) 532 nm diode laser was used to excite the sample through a 50×, N.A. 0.75 objective (NPL AN EPI, Leica). The total data acquisition was performed during 60 seconds using the WiRE software. All the spontaneous Raman spectra have subtracted the PBS solution as background.

Image progressing. Images are acquired with FluoView scanning software and assigned color or overlaid by ImageJ. Linear combination was processed with Matlab. Graphs were assembled with Adobe Illustrator.

Culture medium. Regular HeLa cells medium was made of 90% DMEM medium (11965, invitrogen), 10% FBS (10082, invitrogen) and 1× penicillin/streptomycin (15140, invitrogen); regular hippocampal neuron medium was made of Neurobasal A Medium (10888, Invitrogen), 1× B27 serum free supplement (17504, Invitrogen) and 0.5 mM glutamine (25030, Invitrogen).

Htt-mEos2 plasmid construct and transfection. mHtt94Q-mEos2 plasmid was constructed by replacing CFP gene sequence in pTreTight-Hit94Q-CFP plasmid (Addgene, 23966) with mEos2 gene sequence from pRSETa-mEos2 plasmid (Addgene, 20341). For transfection of mHtt-mEos2 plasmid in HeLa cells, 4 μg mHtt94Q-mEos2 plasmid was transfected using Transfection Reagent (FuGene, Promega).

Optimized Deuterium-Labeling Media 1) D-AA medium (CD-DMEM) for HeLa cells: adapted from regular recipe of DMEM medium (11965, Invitrogen). The D-AA culture medium for HeLa cells was made with 90% CD-DMEM, 10% FBS (10082, invitrogen) and 1× penicillin/streptomycin (15140, invitrogen).

| Amino acids components | Concentration (mM) | Product company and catalog number |
|---|---|---|
| Glycine-$d_5$ | 0.4 | DLM-280, Cambridge isotope |
| L-Arginine•HCl-$d_7$ | 0.398 | DLM-541, Cambridge isotope |
| L-Cysteine•2HCl | 0.2 | C6727, SIGMA (regular)* |
| L-Glutamine-$d_5$ | 4.0 | DLM-1826, Cambridge isotope |
| L-Histidine•HCl•$H_2O$ | 0.2 | H5659, SIGMA (regular)* |
| L-Isoleucine-$d_{10}$ | 0.802 | DLM-141, Cambridge isotope |
| L-Leucine-$d_{10}$ | 0.802 | DLM-567, Cambridge isotope |
| L-Lysine•HCl-$d_8$ | 0.798 | 616214, ALDRICH (Isotech) |
| L-Methionine-$d_3$ | 0.201 | DLM-431, Cambridge isotope |
| L-Phenylalanine-$d_8$ | 0.4 | DLM-372, Cambridge isotope |
| L-Serine-$d_3$ | 0.4 | DLM-582, Cambridge isotope |
| L-Threonine | 0.798 | T8441, SIGMA (regular)* |
| L-Tryptophan | 0.078 | T8941, SIGMA (regular)* |
| L-Tyrosine-$d_2$ | 0.398 | DLM-2317, Cambridge isotope |
| L-Valine-$d_8$ | 0.803 | DLM-488, Cambridge isotope |

Other components (vitamins, Inorganic Salts and glucose) are exactly the same as in the regular DMEM medium (11965, invitrogen).
*The reasons these 4 amino acids are remain in their regular forms are because: first, their deuterated forms have limited number of side chain deuterium and are also relatively expensive; second, their occurrence (percentage) in mammalian cell proteins are small. Thus the lack of the deuterated version for these 4 amino acids would not influence the general deuterium labeling efficiency for CD-DMEM. Same reason applies to below media.

2) D-AA medium (CD-Neurobasal A) for hippocampal neuron culture and organotypic brain slices: adapted from regular recipe of Neurobasal A medium (10888, Invitrogen). The D-AAs culture medium for hippocampal neurons was made of CD-Neurobasal A Medium, 1× B27 serum free supplement (17504, Invitrogen) and 0.5 mM glutamine-$d_5$ (DLM-1826, Cambridge isotope). The CD-Neurobasal A culture medium for organotypic brain slices was made of CD-Neurobasal A Medium, 1× B27 serum free supplement (17504, Invitrogen), 0.5% glucose (15023, invitrogen), 2 mM glutamine-$d_5$ (DLM-1826, Cambridge isotope) and 1× penicillin/streptomycin (15140, invitrogen).

| Amino acids components | Concentration (mM) | Product company and catalog number |
|---|---|---|
| Glycine-$d_5$ | 0.4 | DLM-280, Cambridge isotope |
| L-Alanine-$d_4$ | 0.022 | DLM-250, Cambridge isotope |
| L-Arginine•HCl-$d_7$ | 0.398 | DLM-541, Cambridge isotope |
| L-Asparagine-$d_8$ | 0.006 | 672947 ALDRICH (Isotech) |
| L-Cysteine•2HCl | 0.26 | C6727, SIGMA (regular)* |
| L-Histidine•HCl•$H_2O$ | 0.2 | H5659, SIGMA (regular)* |
| L-Isoleucine-$d_{10}$ | 0.802 | DLM-141, Cambridge isotope |
| L-Leucine-$d_{10}$ | 0.802 | DLM-567, Cambridge isotope |
| L-Lysine•HCl-$d_8$ | 0.798 | 616214, ALDRICH (Isotech) |
| L-Methionine-$d_3$ | 0.201 | DLM-431, Cambridge isotope |
| L-Phenylalanine-$d_8$ | 0.4 | DLM-372, Cambridge isotope |
| L-Proline-$d_7$ | 0.067 | DLM-487, Cambridge isotope |
| L-Serine-$d_3$ | 0.4 | DLM-582, Cambridge isotope |
| L-Threonine | 0.798 | T8441, SIGMA (regular)* |
| L-Tryptophan | 0.078 | T8941, SIGMA (regular)* |
| L-Tyrosine-$d_2$ | 0.398 | DLM-2317, Cambridge isotope |
| L-Valine-$d_8$ | 0.803 | DLM-488, Cambridge isotope |

Other components (vitamins, Inorganic Salts and glucose) are exactly the same as in the regular Neurobasal A medium (10888, Invitrogen).

3) Group I D-AA medium for HeLa cells. The group I D-AA culture medium for HeLa cells was made with 90% group I D-AA medium, 10% FBS (10082, invitrogen) and 1× penicillin/streptomycin (15140, invitrogen).

| Amino acids components | Concentration (mM) | Product company and catalog number |
|---|---|---|
| Glycine | 0.4 | 50046, SIGMA (regular) |
| L-Arginine•HCl | 0.398 | A6969, SIGMA (regular) |
| L-Cysteine•2HCl | 0.2 | C6727, SIGMA (regular) |
| L-Glutamine | 4.0 | G8540, SIGMA (regular) |
| L-Histidine•HCl•$H_2O$ | 0.2 | H5659, SIGMA (regular) |
| L-Isoleucine-$d_{10}$ | 0.802 | DLM-141, Cambridge isotope |
| L-Leucine-$d_{10}$ | 0.802 | DLM-567, Cambridge isotope |
| L-Lysine•HCl | 0.798 | L8662 SIGMA (regular) |
| L-Methionine | 0.201 | M5308 SIGMA (regular) |
| L-Phenylalanine | 0.4 | P5482 SIGMA (regular) |
| L-Serine | 0.4 | S4311 SIGMA (regular) |
| L-Threonine | 0.798 | T8441, SIGMA (regular) |

-continued

| Amino acids components | Concentration (mM) | Product company and catalog number |
|---|---|---|
| L-Tryptophan | 0.078 | T8941, SIGMA (regular) |
| L-Tyrosine | 0.398 | T8566 SIGMA (regular) |
| L-Valine-$d_8$ | 0.803 | DLM-488, Cambridge isotope |

Other components (vitamins, Inorganic Salts and glucose) are exactly the same as in the regular DMEM medium (11965, invitrogen).

4) Group II D-AA medium for HeLa cells. The group II D-AA culture medium for HeLa cells was made with 90% group II D-AA medium, 10% FBS (10082, invitrogen) and 1× penicillin/streptomycin (15140, invitrogen).

| Amino acids components | Concentration (mM) | Product company and catalog number |
|---|---|---|
| Glycine-$d_5$ | 0.4 | DLM-280, Cambridge isotope |
| L-Arginine•HCl-$d_7$ | 0.398 | DLM-541, Cambridge isotope |
| L-Cysteine•2HCl | 0.2 | C6727, SIGMA (regular) |
| L-Glutamine-$d_5$ | 4.0 | DLM-1826, Cambridge isotope |
| L-Histidine•HCl•$H_2O$ | 0.2 | H5659, SIGMA (regular) |
| L-Isoleucine | 0.802 | I7403 SIGMA (regular) |
| L-Leucine | 0.802 | L8912 SIGMA (regular) |
| L-Lysine•HCl-$d_8$ | 0.798 | 616214, ALDRICH (Isotech) |
| L-Methionine-$d_3$ | 0.201 | DLM-431, Cambridge isotope |
| L-Phenylalanine-$d_8$ | 0.4 | DLM-372, Cambridge isotope |
| L-Serine-$d_3$ | 0.4 | DLM-582, Cambridge isotope |
| L-Threonine | 0.798 | T8441, SIGMA (regular) |
| L-Tryptophan | 0.078 | T8941, SIGMA (regular) |
| L-Tyrosine-$d_2$ | 0.398 | DLM-2317, Cambridge isotope |
| L-Valine | 0.803 | V0513 SIGMA (regular) |

Other components (vitamins, Inorganic Salts and glucose) are exactly the same as in the regular DMEM medium (11965, invitrogen).

5) D-AA medium (CD-MEM) for organotypic brain slice: adapted from regular recipe of MEM medium (11095, Invitrogen). The CD-MEM culture medium for organotypic brain slice was made with 90% CD-MEM, 10% FBS (10082, invitrogen), 0.5% glucose (15023, invitrogen) and 1× penicillin/streptomycin (15140, invitrogen).

| Amino acids components | Concentration (mM) | Product company and catalog number |
|---|---|---|
| L-Arginine•HCl-$d_7$ | 0.597 | DLM-541, Cambridge isotope |
| L-Cysteine•2HCl | 0.1 | C6727, SIGMA (regular)* |
| L-Glutamine-$d_5$ | 2.0 | DLM-1826, Cambridge isotope |
| L-Histidine•HCl•$H_2O$ | 0.2 | H5659, SIGMA (regular)* |
| L-Isoleucine-$d_{10}$ | 0.397 | DLM-141, Cambridge isotope |
| L-Leucine-$d_{10}$ | 0.397 | DLM-567, Cambridge isotope |
| L-Lysine•HCl-$d_8$ | 0.399 | 616214, ALDRICH (Isotech) |
| L-Methionine-$d_3$ | 0.1 | DLM-431, Cambridge isotope |
| L-Phenylalanine-$d_8$ | 0.19 | DLM-372, Cambridge isotope |
| L-Threonine | 0.403 | T8441, SIGMA (regular)* |
| L-Tryptophan | 0.049 | T8941, SIGMA (regular)* |
| L-Tyrosine-$d_2$ | 0.199 | DLM-2317, Cambridge isotope |
| L-Valine-$d_8$ | 0.393 | DLM-488, Cambridge isotope |

Other components (vitamins, Inorganic Salts and glucose) are exactly the same as in the regular MEM medium (11095, invitrogen).

6) For zebrafish: Wild-type zebrafish embryos at the 1-cell stage were injected with 1 nL D-AA solution and allowed to develop normally for another 24 h. The zebrafish embryos at 24 hpf were manually dechorionated before imaging. D-AA solution was made of 150 mg uniformly deuterium-labeled amino acid mix (20 aa) (DLM-6819, Cambridge Isotope) dissolved in 1 mL PBS, with subsequent filtration using Millipore sterile syringe Filters (0.22 μm, SLGV033RS).

7) For mice: 1. Oral administration: 3-week-old mice were fed with D-AA containing drinking water for 12 days before harvesting the liver and intestine tissues. The drinking water was made of 500 mg uniformly deuterium-labeled amino acid mix (20 aa) (DLM-6819, Cambridge Isotope) dissolved in 200 ml PBS, with subsequent filtration using Millipore sterile syringe Filters (0.22 μm, SLGV033RS). 2. Intraperitoneal injection: 3-week-old mice were injected with 500 μl D-AAs solution at the $0^{th}$ h, $12^{th}$ h and $24^{th}$ h. The tissues were then harvested at the $36^{th}$ h after the first injection. D-AA solution was made of 500 mg uniformly deuterium-labeled amino acid mix (20 aa) (DLM-6819, Cambridge Isotope) dissolved in 2 ml PBS solutions, with subsequent filtration using Millipore sterile syringe Filters (0.22 μm, SLGV033RS).

Example 1a: Sensitivity Optimization and Time-Lapse Imaging of the De Novo Proteome Synthesis Dynamics The cell culture medium reported previously was prepared by supplying uniformly deuterium-labeled whole set of amino acids to a commercially available medium that is deficient of leucine, lysine and arginine (Wei L, Yu Y, Shen Y, Wang M C, Min W (2013) Vibrational imaging of newly synthesized proteins in live cells by stimulated Raman scattering microscopy. *Proc. Natl. Acad. Sci. USA.* 110: 11226-11231). Due to the presence of other regular amino acids already in the commercial medium, the resulting partially deuterated medium has only about 60% deuteration efficiency. In the present paper, we custom prepared new media that replace nearly all the regular amino acids by the D-AA counterparts (details in Supporting Information). As shown in the spontaneous Raman spectra (FIG. 2a), the optimized medium (spectrum 205) displays a 50% signal increase compared with the partially deuterated medium (spectrum 210). Indeed, SRS images targeting C-D vibrational peak at 2133 $cm^{-1}$ confirms a 50% average intensity boost in live HeLa cells (FIG. 2b). The use of optimized D-AA medium now leads to an about 8 times higher signal than when using a single leucine-$d_{10}$ (FIG. 2a, spectrum 205 vs. spectrum 210). In addition to improving labeling strategy, non-trivial instrumentation optimizations are also carried out to further improve SRS detection sensitivity and acquisition speed, including increasing the laser output and microscope system throughput for near-IR wavelengths, replacing the acousto-optic modulator (AOM) with an electro-optic modulator (EOM) for a 30% higher modulation depth, and employing a high-speed lock-in amplifier for faster image acquisition.

With much-improved sensitivity, protein synthesis can now be imaged with superb spatial and temporal resolutions. Spatially, we visualized newly synthesized proteins from fine structures (likely dendritic spines, indicated by arrow heads) of live neurons (FIG. 2c). Temporally, we could readily image newly synthesized proteins in live HeLa cells in less than one-hour incubation with the optimized deuteration medium (FIG. 2d). Control image with protein synthesis inhibitors only displays vague cell outlines which presumably come from the free D-AA pool (sub-mM concentration). Moreover, using a fast lock-in amplifier (details in Methods), our current imaging speed can be as fast as 3 s per frame (512×512 pixels), nearly 10 times faster than before, which enables time-lapse imaging in live cells with minimum photo-toxicity to cell viabilities. FIG. 2€ presents time-lapse SRS imaging of a same set of live HeLa cells gradually synthesizing new proteins over time from 10 min to 5 h incubation in optimized D-AA medium. The obvious cell migration and division prove their viability, supporting high bio-compatibility of our technique. To our best knowledge, this is the first time that long-term time-lapse imaging of proteome synthesis dynamics is demonstrated on single live mamamian cells.

Example 1b: SRS Imaging of Protein Degradation in Live HeLa Cells

Besides imaging protein synthesis, our imaging platform offers the ability to probe protein degradation simultaneously. Experimentally, we intend to probe the pre-existing protein pool by targeting the CH3 showing a strong peak at 2940 cm-1, as newly synthesized proteins will be mostly carrying C-D peaked around 2133 cm-1. However, the 2940 cm-1 CH3 protein channel is known to suffer from undesired crosstalk from the CH2 lipid signal peaked at 2845 cm-1. To obtain a clean protein component, we adopt two-color SRS imaging at both 2940 cm-1 and 2845 cm-1 channels followed by a linear combination algorithm which has been effectively applied in cells, tissues and animals. The subsequently obtained images show the pure distribution of old protein pools (exclusively from CH3) and the distribution of lipids (exclusively from CH2), respectively. Hence protein degradation could be tracked by imaging the old protein distributions over time when cells are growing in the D-AA medium.

FIG. 3a shows time-dependent SRS images of old protein distributions (CH3) in live HeLa cells when incubated with D-AAs from 0 h to 96 h. Clearly, the old protein pool is degrading, as shown by the decay of its average intensity. As a contrast, the total lipid images display no obvious intensity change (FIG. 3b). In addition, the spatial patterns of old proteins (FIG. 3a) reveal a faster decay in the nucleoli than the cytoplasm. This observation is consistent with the fact that neucleoli have active protein turnover and also with our previous report that C-D labeled newly synthesized proteins are more prominent in nucleoli (Wei L, Yu Y, Shen Y, Wang M C, Min W (2013) Vibrational imaging of newly synthesized proteins in live cells by stimulated Raman scattering microscopy. *Proc. Natl. Acad. Sci. USA*. 110:11226-11231). Single exponential decay fitting of the average intensities in FIG. 3a yields a decay time constant of 45±4 h (FIG. 3c), corresponding to a proteome half-live of 31±3 h which is very close to the data reported by mass spectrometry (35 h) (Cambridge S B et al. (2011) Systems-wide proteomic analysis in mammalian cells reveals conserved, functional protein turnover. *J. Proteome Res*. 10:5275-5284). Therefore, our imaging platform is capable of observing both protein synthesis and degradation by imaging at C-D channel and $CH_3$ channel, respectively, thus capturing proteomic metabolism dynamics in full-scope.

Retrieval of pure $CH_3$ and $CH_2$ signals by linear combination between 2940 $cm^{-1}$ and 2845 $cm^{-1}$ channels was conducted employing equations follow Lu F-K et al. (2012) Multicolor stimulated Raman scattering microscopy. *Mol. Phys*. 110:1927-1932; and Yu Z et al. (2012) Label-free chemical imaging in vivo: three-dimensional non-invasive microscopic observation of amphioxus notochord through stimulated Raman scattering (SRS). *Chem. Sci*. 3:2646-2654. Pure $CH_3$ signal can be retrieved as $[c]_{protein}$ □5.2*(2940 $cm^{-1}$ signal)—4.16*(2845 $cm^{-1}$ signal); Pure $CH_2$ signal can be retrieved as $[C]_{lipid}$ □1.2*(2845 $cm^{-1}$ signal)—0.3*(2940 $cm^{-1}$ signal). This algorithm was tested with skin tissue samples, yielding similar results as reported in Lu F-K et al. (2012) Multicolor stimulated Raman scattering microscopy. *Mol. Phys*. 110:1927-1932; and Yu Z et al. (2012) Label-free chemical imaging in vivo: three-dimensional non-invasive microscopic observation of amphioxus notochord through stimulated Raman scattering (SRS). *Chem. Sci*. 3:2646-2654.

Example 1c: Two-Color Pulse-Chase SRS Imaging of Two Sets of Temporally Defined Proteins Inspired by the popular pulse-chase analysis in classic autoradiography techniques and recent two-color BONCAT imaging (Beatty K E, Tirrell D A (2008) Two-color labeling of temporally defined protein populations in mammalian cells. Bioorg. Med. Chem. Lett. 18:5995-5999), we aim to exploit another dimension of probing dynamic protein metabolism with two-color pulse-chase imaging of proteins labeled at different times. To do so, we need to rationally divide total D-AAs into two sub-sets with distinct Raman spectra. We reasoned that Raman peaks of C-D stretching are closely related to their chemical environments, thus the structural difference between D-AAs should lead to diverse Raman peak positions and shapes. We then examined the spontanesous Raman spectra of each D-AA sequentially, and subsequently identified two subgroups. Group I contains three amino acids, leuine-d10, isoleucine-d10 and valine-d8, structurally known as branched-chain amino acids (FIG. 4a). All members of group I exhibits multiple distinct Raman peaks with the first one around 2067 cm-1.

The rest of D-AAs without branched chains are then categorized into group II, all of which show a prominent Raman peak around 2133 cm-1 (three examples shown in FIG. 4b). To test inside cells, Raman spectra of HeLa cells cultured in either group I D-AA medium only (element 405) or group II D-AA medium only (element 410) are shown in FIG. 4c. Based on the spectra, we choose to acquire two-color narrow-band SRS images at 2067 cm-1 and at 2133 cm-1. By constructing and utilizing a linear combination algorithm, similar to the one used for CH3 and CH2 above, pure signals of proteins labeled by group I D-AAs and by group II D-AAs can be successfully separated and quantitatively visualized (e.g. FIG. 7). In other exemplary embodiments, the images are obtained with a hyper-spectral imaging approach using broadband femtosecond lasers.

We now chose the mutant huntingtin (mHtt) protein in Huntington's disease as our model system for pulse-chase imaging demonstration. It is believed that Huntington's disease is caused by a mutation from normal huntingtin gene to mHtt gene expressing aggregation-prone mHtt proteins with poly-glutamine (polyQ) expansion (Walker F O (2007) Huntington's Disease. The Lancet. 369: 218-228). For easy visualization by fluorescence, we tagged mHtt (with 94Q) with a fluorescent protein marker, mEos2. As illustrated by the cartoon in FIG. 9d, HeLa cells were first transfected with mHtt94Q-mEos2 plasmid in regular medium for 4 h, and then replaced with group II D-AA medium for 22 h before changing to group I D-AA medium for another 20 h. SRS images are acquired at 2067 cm-1 and 2133 cm-1 channels, respectively, and subsequently processed with linear combination.

Fluorescence overlaid with bright field image informs us the formation of a large aggregate triggered by aggregation-prone polyQ expansion in mHtt94Q-mEos2 (FIG. 4d, fluorescence). Interestingly, proteins labeled with group II D-AAs during the initial pulse period mainly concentrate within the core of the aggregate (FIG. 4d, element 415), whereas proteins labeled with group I D-AAs during the subsequent chase period occupy the entire volume of the aggregate (FIG. 4d, element 420). The merged image between group I and group II images, as well as the intensity profiles across the aggregate, further confirm the observation of a yellow core inside and a green shell outside (FIG. 4d, merged). This two-color pulse-chase result suggests that the core is aggregated earlier in time and the later produced mHtt proteins are then recruited to and percolate through the aggregate to increases its overall size, in agreement with recently reported results by fluorescence (Schipper-Krom S et al. (2014)) Dynamic recruitment of active proteasomes into polyglutamine initiated inclusion bodies. FEBS Lett. 588:151-159). The demonstration here thus illustrates that our imaging platform using the two subgroups of D-AAs is readily applicable for performing pulse-chase imaging to probe the complex and dynamic aspects of proteome metabolism.

In order to achieve SRS imaging of pure group I D-AA labeled protein distribution and pure group II D-AA labeled protein distribution simultaneously, we construct a robust linear combination algorithm to retrieve the underlying pure concentration information for two-color pulse-chasing imaging similar to the one presented above from Lu F-K et al. (2012) Multicolor stimulated Raman scattering microscopy. Mol.Phys.110:1927-1932; and Yu Z et al. (2012) Label-free chemical imaging in vivo: three-dimensional non-invasive microscopic observation of amphioxus notochord through stimulated Raman scattering (SRS). Chem. Sci. 3:2646-2654. Since SRS signals exhibit linear concentration dependence with analyte concentrations, two chemical species with different Raman spectra can be retrieved quantitatively with two-color SRS imaging. Hence, based on the spectra shown in FIG. 4c, we choose to acquire narrow-band SRS images at 2067 cm-1 and 2133 cm-1 channels, respectively, and perform subsequent linear combination algorithm to remove the spectral cross-talk.

The proper algorithm with the corresponding cross-talk coefficients is constructed with SRS images of standard reference samples, i.e., pure group I D-AA labeled protein and pure group II D-AA labeled protein. To do so, we labeled HeLa cells with only group I D-AA medium FIG. 7a and only group II D-AA medium FIG. 7b, respectively, and acquired a set of image pairs at 2067 cm-1 and 2133 cm-1 channels for each cell samples (e.g. FIG. 7).

For any sample labeled with both groups of D-AAs, the measured SRS signals at 2067 cm-1 and 2133 cm-1 channels can be written as the following, with linear relationship to group I D-AA and group II D-AA concentrations ([c]group I and [c]group II):

$$\begin{bmatrix} 2067 \text{ cm}^{-1} \text{ signal} \\ 2133 \text{ cm}^{-1} \text{ signal} \end{bmatrix} = \begin{bmatrix} i_{group\,I,2067\,cm^{-1}} & i_{group\,II,2067\,cm^{-1}} \\ i_{group\,I,2133\,cm^{-1}} & i_{group\,II,2067\,cm^{-1}} \end{bmatrix} \begin{bmatrix} [c]_{groupI} \\ [c]_{group\,II} \end{bmatrix},$$

where $i_{groupI,2067\,cm^{-1}}$, $i_{groupI,2133\,cm^{-1}}$, $i_{groupII,2067\,cm^{-1}}$, $i_{groupII,2133\,cm^{-1}}$ are the average pixel intensity recorded inside cells in FIG. 7a and FIG. 7b.

Thus group I D-AA and group II D-AA concentrations can then be easily solved as:

$$[c]_{groupI} = \frac{i_{groupII,2133\,cm^{-1}}(2067\text{ cm}^{-1}\text{ signal}) - i_{groupII,2067\,cm^{-1}}(2133\text{ cm}^{-1}\text{ signal})}{i_{groupII,2133\,cm^{-1}}i_{groupII,2067\,cm^{-1}} - i_{groupII,2067\,cm^{-1}}i_{groupII,2133\,cm^{-1}}},$$

-continued $$[c]_{groupII} = \frac{i_{groupI,2067\,cm^{-1}}(2133\text{ cm}^{-1}\text{ signal}) - i_{groupI,2133\,cm^{-1}}(2067\text{ cm}^{-1}\text{ signal})}{i_{groupII,2133\,cm^{-1}}i_{groupII,2067\,cm^{-1}} - i_{groupII,2067\,cm^{-1}}i_{groupII,2133\,cm^{-1}}}.$$

Taking the average pixel intensity recording in FIG. 7a and FIG. 7b into the above equations, the final linear combination algorithm reads as:

$$[c]\text{group } I \infty 1.06*(2067 \text{ cm-1 signal}) - 0.0047*(2133 \text{ cm-1 signal}), \quad (1)$$

$$[c]\text{group } II \infty (2133 \text{ cm-1 signal}) - 1.15*(2067 \text{ cm-1 signal}). \quad (2)$$

Example 1d: SRS Imaging of Newly Synthesized Proteins in Live Mouse Brain Tissues Going above the cellular level, we now apply our imaging platform to a more complex level, organotypical brain tissues. In our study, we focus on the hippocampus because it is the key region in brains that involves extensive protein synthesis. As expected, active protein synthesis is found in the hippocampal region, particularly in the dentate gyrus, which is known for its significant role in both long-term memory formation and adult neurogenesis. SRS image at 2133 cm-1 (FIGS. 5a, C-D) of a live mouse organotypic brain slices cultured in D-AA medium for 30 h, reveals active protein synthesis from both the soma and the neurites of individual neurons in dentate gyrus. In addition, the old protein (CH3) and total lipids (CH2) images are presented simultaneously for multichannel analysis (FIG. 5a).

In order to investigate spatial pattern of protein synthesis on a larger scale, we imaged the entire brain slice by acquiring large-area image mosaics. A 4-by-3 mm image (FIG. 5b) of another organotypic slice displays overlayed patterns from new proteins (2133 cm-1, element 505), old proteins (CH3, element 510) and lipids (CH2, element 515). Intriguing spatial variation is observed: while the distribution of old proteins are relatively homogenous across the field of view, newly synthesized proteins are either concentrated in dentate gyrus or scattered within individual neurons throughout the cortex, suggesting high activities in these two regions. Thus, we have demonstrated the ability to directly image protein synthesis dynamics on living brain tissues with subcellular resolution and multi-channel analysis, which was difficult to achieve with other existing methods. The intricate relationship between protein synthesis and neuronal plasticity is currently under investigation on this platform.

Example 1e: SRS Imaging of Newly Synthesized Proteins In Vivo

One prominent advantage of our labeling strategy is its non-toxicity and minimal invasiveness to animals. We thus move up to the physiological level to image protein metabolism in embryonic zebrafish and mice. Zebrafish are popular model organisms due to their well-understood genetics and transparent embryos, amenable to optical imaging. We injected 1 nL D-AA solution into zebrafish embryos at the 1-cell stage (150 ng D-AAs per embryo), and then allowed them to develop normally for 24 h (FIG. 6a, bright field) before imaging the whole animal. We found a high signal of newly synthesized proteins (FIG. 6a, 2133 cm-1) in the somites at the embryonic zebrafish tail, consistent with the earlier BONCAT result (Hinz F I, Dieterich D C, Tirrell D A, Schuman E M (2012) Non-canonical amino acid labeling in vivo to visualize and affinity purify newly synthesized proteins in larval zebrafish. ACS Chem. Neurosci. 3:40-49). The spatial pattern of this signal appears similar to that of the old protein distribution (FIG. 6a, CH3), but almost complementary to the lipid distribution (FIG. 6a, CH2).

Finally we demonstrate on mammals—mice. We administered the drinking water containing D-AAs to 3-week-old mice for 12 days, and then harvested liver and intestine tissues for subsequent imaging. No toxicity was observed for the fed mice. The SRS images from both live liver tissues (FIG. 6b) and live intestine tissues (FIG. 6c) illustrate the distributions of newly synthesized proteins (2133 cm-1, C-D) during the feeding period, which resemble the total protein distribution (1655 cm-1, Amide I). On a faster incorporation timescale, live liver and intestine tissues obtained after intraperitoneal injection of D-AAs into mice for 36 h reveal spatial patterns (FIGS. 6b-6c) similar to the feeding results above as well as the click-chemistry based fluorescence staining (Liu J, Xu Y, Stoleru D, Salic A (2012) Imaging protein synthesis in cells and tissues with an alkyne analog of puromycin. Proc. Natl. Acad. Sci. USA 109:413-418). All these results support our imaging platform as a highly suitable technique for in vivo interrogation.

Figure 6:
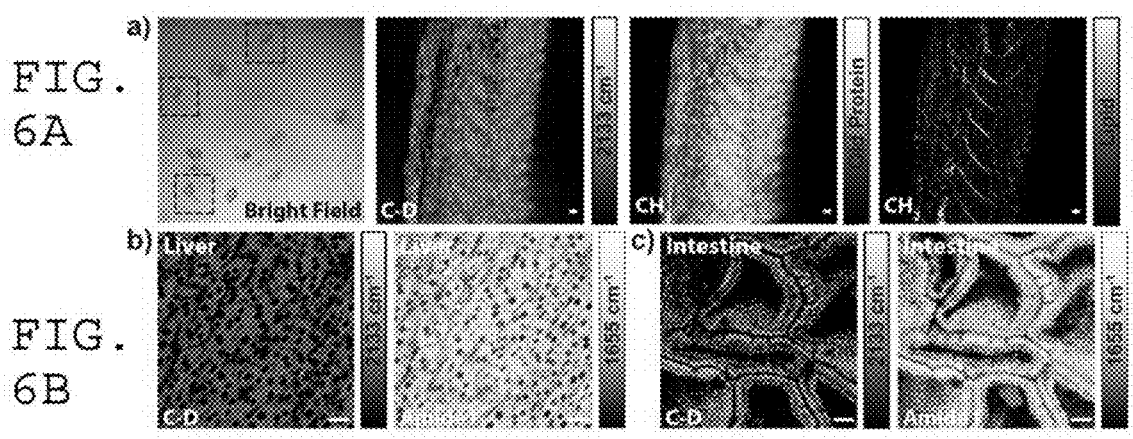
FIG. 6 shows SRS imaging of newly synthesized proteins in vivo. For example.

FIG. 8 shows raw C-D on-resonance (2133 cm-1) and off-resonance (2000 cm-1) SRS images of newly synthesized proteins in vivo in FIG. 6. FIG. 8a SRS C-D on-resonance and off-resonance images of a 24 hpf embryonic zebrafish. The difference image between C-D on-resonance and off-resonance (pixel-by-pixel subtraction) shows pure C-D labeled protein distribution in the somites of an embryonic zebrafish tail, as in FIG. 6a. FIGS. 8b-8c SRS C-D on-resonance and off-resonance images of live mouse liver FIG. 8b and intestine FIG. 8c tissues harvested from the mice after administering with D-AA containing drinking water for 12 days. The difference image between C-D on-resonance and off-resonance (pixel-by-pixel subtraction) shows pure C-D labeled protein distribution in the liver and intestine tissues, shown in FIG. 6b and FIG. 6c, respectively. The residual signal presented in the off-resonance images mainly comes from cross-phase modulation induced by highly scattering tissue structures.

FIG. 9 shows SRS imaging for newly synthesized proteins in vivo with intraperitoneal injection of mice with D-AA solutions. FIGS. 9a-9b SRS images of live mouse liver FIG. 9a and intestine 9b tissues harvested from mice after intraperitoneal injection injected with D-AAs solutions for 36 h. 2133 cm-1 channel shows newly synthesized proteins (off-resonance image subtracted) that resemble the distribution of total proteins as shown in the 1655 cm-1 image (Amide I). (c-d) Corresponding raw C-D on-resonance (2133 cm-1) and off-resonance (2000 cm-1) images are shown as references for liver c and intestine d tissues. Scale bar, 10 μm.

Exemplary Physical Principle Of Isotope-Based SRS Imaging

SRS microscopy can be a molecular-contrast, highly sensitive, imaging procedure with intrinsic 3D sectioning capability. It selectively images the distribution of molecules that carry a given type of chemical bonds through resonating with the specific vibrational frequency of the targeted bonds. (See, e.g., References 47, 54 and 65). As FIG. 5a illustrates, by focusing both temporally and spatially overlapped Pump and Stokes laser pulse trains into samples, the rate of vibrational transition can be greatly amplified by about 107 times when the energy difference of the two laser beams matches the particular chemical bond vibration, Qvib. (See, e.g., Reference 65). Accompanying such stimulated activation of one vibrational mode, one photon can be created into the Stokes beam, and simultaneously another photon can be annihilated from the Pump beam, a process called stimulated Raman gain and stimulated Raman loss, respectively. The energy difference between the Pump photon and the Stokes photon can be used to excite the vibrational mode, fulfilling energy conservation. FIG. 5b shows a high-frequency modulation procedure, where the intensity of the Stokes beam can be turned on and off at 10 MHz, and can be employed to achieve shot-noise-limited detection sensitivity by suppressing laser intensity fluctuations occurring at low frequencies. The transmitted Pump beam after the sample can be detected by a large-area photodiode, and the corresponding stimulated Raman loss signal, which also occurs at 10 MHz, can be demodulated by a lock-in amplifier. By scanning across the sample with a laser-scanning microscope, a quantitative map with chemical contrast can be produced from the targeted vibrating chemical bonds. As the SRS signal can be dependent on both Pump and Stokes laser beams, the nonlinear nature can provide a 3D optical sectioning ability.

The vibrational signal of C-D can be detected as an indicator for newly synthesized proteins that metabolically incorporate deuterium-labeled amino acids. (See, e.g., FIG. 5b). When hydrogen atoms can be replaced by deuterium, the chemical and biological activities of biomolecules remain largely unmodified. The C-D stretching motion can display a distinct vibrational frequency from all the other vibrations of biological molecules inside live cells. The reduced mass of the C-D oscillator can be increased by two folds when hydrogen can be replaced by deuterium. Based on the above Equation, $\Omega_{vib}$ can be reduced by a factor of 2. The experimentally measured stretching frequency can be shifted from ~2950 cm-1 of C—H to ~2100 cm-1 of C-D. The vibrational frequency of 2100 cm-1 can be located in a cell-silent spectral window in which no other Raman peaks exist, thus enabling detection of exogenous C-D with both high specificity and sensitivity.

Imaging optimization by metabolic incorporation of deuterium-labeled all amino acids in live HeLa cells with multicolor SRS imaging. Although leucine can be the most abundant essential amino acid, it only accounts for a small fraction of amino acids in proteins. Thus, the deuterium labeling of all the amino acids can lead to a substantial signal enhancement. Indeed, the spontaneous Raman spectrum (e.g., FIG. 33a) of HeLa cells incubated with deuterium-labeled all 20 amino acids (e.g., prepared by supplying uniformly deuterium-labeled whole set of amino acids to leucine, lysine and arginine deficient DMEM medium) can exhibit C-D vibrational peaks about five times higher than shown in FIG. 2 under the same condition. The corresponding SRS image at 2133 cm-1 (e.g., FIG. 33b) can show a significantly more pronounced signal than that in FIG. 2 under the same intensity scale. In particular, nucleoli (e.g., indicated by arrows in FIG. 33b and verified by DIC visualization) can exhibit the highest signal. Nucleoli, the active sites for ribosomal biogenesis, have been reported to involve rapid nucleolar assembly and proteomic exchange (See, e.g., Reference 68-70). Such fast protein turnover can be reflected by the spatial enrichment of newly synthesized protein signals in those subcellular areas. (See, e.g., FIG. 33b). Note that SRS imaging here can be directly performed on live cells and hence free from potential complications due to fixation and dye conjugation. Again, the off-resonant image at 2000 cm-1 can be clean and dark (e.g., FIG. 33c), proving the specificity of SRS imaging of C-D at 2133 cm-1. In addition to imaging newly synthesized proteins, SRS can readily image intrinsic biomolecules in a label-free manner. By simply adjusting the energy difference between the Pump and the Stokes beams to match the vibrational frequency of amide I, lipids and total proteins respectively. FIGS. 33d-f show the SRS images of amide I band at 1655 cm-1 primarily attributed to proteins, CH2 stretching at 2845 cm-1 predominantly for lipids and CH3 stretching at 2940 cm-1 mainly from proteins with minor contribution from lipids.

Figure 34:
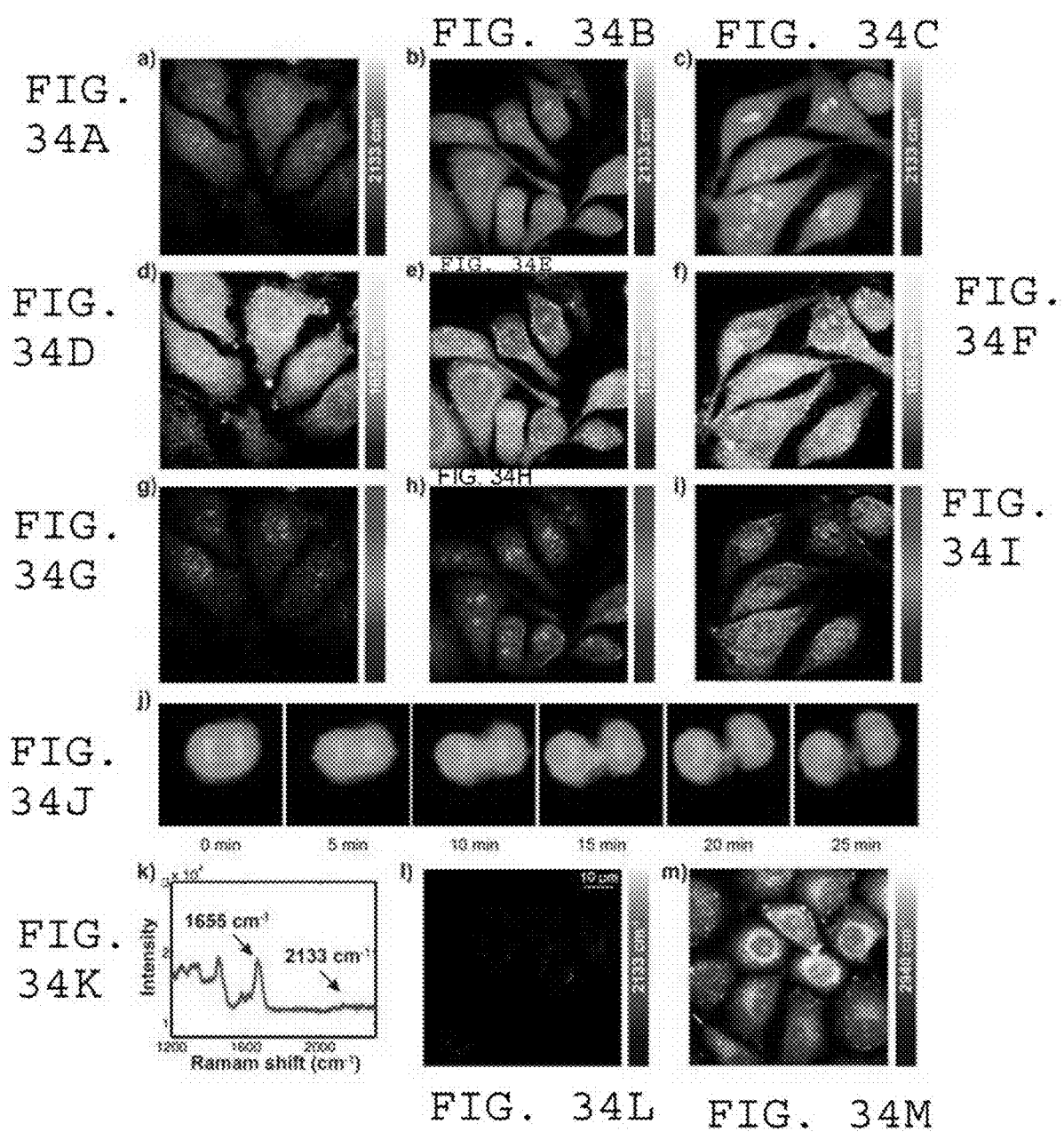
FIG. 34 is a set of exemplary images based on SRS imaging of time-dependent de novo protein synthesis and drug-induced protein synthesis inhibition effect in live HeLa cells incubated in deuterium-labeled all amino acid medium. For example, FIG. 34a-34f SRS image targeting the central 2133 cm$_{-1}$ vibrational peak of C-D displays a time-dependent signal increase (5 hrs—FIG. 34a, 12 hrs—FIG. 34b, 20 hrs—FIG. 34c) of the newly synthesized proteins, with nucleoli being gradually highlighted. As a control, the amide I (1655 cm$_{-1}$) signal remains at a steady state over time (5 hrs—FIG. 34d, 12 hrs—FIG. 34e, 20 hrs—FIG. 34f).

Exemplary Time-Dependent De Novo Protein Synthesis And Protein Synthesis Inhibition Being linearly dependent on analyte concentration, SRS contrast can be well suited for quantification of de novo protein synthesis in live cells. Here the time-dependent protein synthesis images can be shown under the same intensity scale. (See, e.g., FIGS. 348a-c). As expected, the new protein signal (e.g., 2133 cm-1) from 5-hour, 12-hour and 20-hour incubation can increase substantially over time (e.g., FIGS. 34a-c) while the amide I (e.g., 1655 cm-1) signal can remain at a steady state. (See, e.g., FIGS. 34d-f). Since protein distribution can often be heterogeneous in biological systems, a more quantitative representation by acquiring ratio images can be shown between the newly synthesized proteins and the total proteome (e.g., from either amide I or CH3). FIGS. 34g-i depict the fraction of newly synthesized proteins (e.g., 2133 cm-1) among the total proteome (e.g., 1655 cm-1) and its spatial distribution. The fraction of newly synthesized proteins growing with time from 5 hours to 20 hours can highlight nucleoli as the subcellular compartments with fast protein turnover. (See, e.g., Reference 68-70). Such quantitative ratio imaging of new versus old proteomes can be very difficult to obtain using BONCAT or mass spectroscopy without the destruction of cells. Moreover, FIG. 34j shows time-lapse SRS images of a live dividing HeLa cell after 20-hour incubation in deuterium-labeled all amino acids medium, clearly proving the viability of cells under the imaging condition.

The effect of protein synthesis inhibition by chemical drugs can be further tested to validate that the detected C-D signal indeed derives from nascent proteins. HeLa cells incubated with deuterium-labeled all amino acids together with 5 μM anisomycin, which can work as a protein synthesis inhibitor by inhibiting peptidyl transferase or the 80S ribosome system, show the absence of the C-D signal in the spontaneous Raman spectrum. (See, e.g., FIG. 34k). Furthermore, SRS imaging of the same samples (e.g., FIG. 34i) can exhibit drastically weaker signal (See, e.g., Reference 71) when compared to FIG. 34b without the protein synthesis inhibitor. As a control, the corresponding 2940 cm-1 image (e.g., FIG. 34m) of total proteome remains at a similar level as the non-drug treated counterpart in FIG. 34f. Thus, the detected C-D SRS signal (e.g., FIGS. 34a-c) can originate from deuterium-labeled nascent proteins, which can vanish upon adding the protein synthesis inhibitor.

Exemplary Demonstration on HEK293T Cells And Neuron-Like Differentiable Neuroblastoma N2A Cells Two additional mammalian cell lines can be chosen for further demonstration: human embryonic kidney HEK293T cells, and neuron-like neuroblastoma mouse N2A cells, which can be induced to differentiate with the growth of neurites (e.g., axons and dendrites). The spontaneous Raman spectrum (e.g., FIG. 35a) of HEK293T cells incubated with deuterium-labeled all amino acids for 12 hours can exhibit a 2133 cm-1 C-D channel signal nearly as high as the 1655 cm-1 amide channel signal. The resulting SRS image can show a bright signal for new proteins with an intense pattern residing in nucleoli. (See, e.g., FIG. 35b). As before, the off-resonant image (e.g., 2000 cm-1) can display vanishing background (e.g., FIG. 35c); the amide I channel (e.g., 1655 cm-1) image (e.g., FIG. 35d) can exhibit consistent overall proteome distributions similar to that in HeLa cells; CH2 channel (e.g., 2845 cm-1) image (e.g., FIG. 35e) depicts a more diffusive lipid distribution in cytoplasm compared to that in HeLa cells. Consistent with the results obtained in HeLa cells above, the ratio image (e.g., FIG. 35f) between the newly synthesized proteins (e.g., FIG. 35b) and the total proteins (e.g., FIG. 35d) highlights nucleoli for active protein turnover in HEK293T cells as well. (See, e.g., References 44-46).

In addition to showing the ability to image newly synthesized proteins inside cell body, the exemplary SRS can also be applied to tackle more complex problems, such as de novo protein synthesis in neuronal systems. (See, e.g., Reference 26-28). Under differentiation condition, N2A cells massively grow new neurites from cell bodies and form connections with other cells. FIG. 10a shows the image of newly synthesized proteins after induction for differentiation, by simultaneously differentiating the N2A cells and supplying with the deuterium labeled all amino acids for 24 hours. Similar to HeLa and HEK293T cells, N2A cell bodies can be observed to display high-level protein synthesis. Newly synthesized proteins can also be observed in a subset of, but not all neurites (e.g., FIGS. 36a and 36b), which can imply that the observed neurites in FIG. 360a can be newly grown under the differentiation condition. For a detailed visualization, FIGS. 36c and 10d show the zoomed-in regions in the dashed squares in FIGS. 36a and 36b respectively. A more comprehensive examination is illustrated by both the ratio image (e.g., FIG. 36e) between FIGS. 36c and 36d and the merged image (e.g., FIG. 36f) with 3605 designating new protein signal from FIG. 36c and 3610 designating total protein signal from FIG. 36d. On one hand, both the ratio image and the merged image highlight the neurites with higher percentage of new proteins (e.g., indicated by stars), implying these neurites can be newly grown. On the other hand, from the merged image, there can be some neurites (e.g., indicated by arrows) showing obvious signals in the green channel (e.g., total proteins) only but with no detectable signal in the red channel (e.g., new proteins).

Hence, the neurites indicated by arrows can be most likely older than their starred counterparts. In addition, the transition from 3610 to 3605 in the merged image (e.g., FIG. 360f) can imply the growth direction by which new neurites form and grow. A more relevant system to study de novo protein synthesis and neuronal activities can be hippocampal neurons, which can be known to be involved in long-term memory formation (See, e.g., Reference 26-28). SRS image (e.g., 2133 cm-1) of hippocampal neuron cells incubated with deuterium-labeled all amino acids can show a newly synthesized protein pattern in the neurites.

Example 2: In Vitro and In Vivo Labeling with Alkyne Tags

Exemplary Methods and Materials

Bond-selective stimulated Raman scattering (SRS) microscopy. FIG. 37b shows details of the microscopy setup. An integrated laser system (picoEMERALD, Applied Physics & Electronics, Inc.) was chosen as the light source for both pump and Stokes beams. Briefly, picoEMERALD provides an output pulse train at 1064 nm with 6 ps pulse width and 80 MHz repetition rate, which serves as the Stokes beam. The frequency doubled beam at 532 nm is used to synchronously Seed a picosecond optical parametric oscillator (OPO) to produce a mode-locked pulse train with 5~6 ps pulse width (the idler beam of the OPO is blocked with an interferometric filter). The output wavelength of the OPO is tunable from 720 to 990 nm, which serves as the pump beam. The intensity of the 1064 nm Stokes beam is modulated sinusoidally by a built-in electro-optic modulator at 8 MHz with a modulation depth of more than 95%. The pump beam is then spatially overlapped with the Stokes beam by using a dichroic mirror inside picoEMERALD. The temporal overlap between pump and Stokes pulse trains is ensured with a built-in delay stage and optimized by the SRS signal of pure dodecane liquid at the microscope.

Pump and Stokes beams are coupled into an inverted multiphoton laser-scanning microscope (FV1200MPE, Olympus) optimized for near-IR throughput. A 60× water objective (UPlanAPO/IR, 1.2 N.A., Olympus) with high near-IR transmission is used for all cell imaging. The pump/Stokes beam size is matched to fill the back-aperture of the objective. The forward going pump and Stokes beams after passing through the sample are collected in transmission with a high N.A. condenser lens (oil immersion, 1.4 N.A., Olympus) which is aligned following Kohler illumination. A telescope is then used to image the scanning mirrors onto a large area (10 by 10 mm) Si photodiode (FDS1010, Thorlabs) to descan beam motion during laser scanning. The photodiode is reverse biased by 64 V from a DC power supply to increase both the saturation threshold and response bandwidth. A high O.D. bandpass filter (890/220 CARS, Chroma Technology) is placed in front of the photodiode to block the Stokes beam completely and to transmit the pump beam only.

The output current of the photodiode is electronically pre-filtered by an 8-MHz band-pass filter (KR 2724, KR electronics) to suppress both the 80 MHz laser pulsing and the low-frequency fluctuations due to laser scanning cross the scattering sample. It is then fed into a radio frequency lock-in amplifier (SR844, Stanford Research Systems) terminated with 50Ω to demodulate the stimulated Raman loss signal experienced by the pump beam. The in-phase X-output of the lock-in amplifier is fed back into the analog interface box (FV10-ANALOG) of the microscope. The time constant is set for 10 µs (the shortest available with no additional filter applied). The current SRS imaging speed is limited by the shortest time constant available from the lock-in amplifier (SR844). For all imaging, 512 by 512 pixels are acquired for one frame with a 100 µs of pixel dwell time (26 s per frame) for laser scanning and 10 µs of time constant from the lock-in amplifier. Laser powers after 60× IR objective used for imaging are: 130 mW for modulated Stokes beam; 120 mW for the pump beam in 2133 cm-1, 2142 cm-1, 2000 cm-1 and 1655 cm-1 channels, 85 mW for the pump beam in 2230 cm-1 and 2300 $cm^{-1}$ channels, and 50 mW for pump beam in 2845 $cm^{-1}$ channels.

Spontaneous Raman Spectroscopy. The spontaneous Raman spectra were acquired using a laser confocal Raman microscope (Xplora, Horiba Jobin Yvon) at room temperature. A 12 mW (after the microscope objective), 532 nm diode laser was used to excite the sample through a 50×, N.A.=0.75 air objective (MPlan N, Olympus). The total data acquisition time was 300 s using the LabSpec 6 software. All the spontaneous Raman spectra have subtracted the PBS solution background.

Materials. 5-Ethynyl-2'-deoxyuridine (EdU) (T511285), 17-Octadecynoic acid (17-ODYA) (08382), DMEM medium without L-methionine, L-cystine and L-glutamine (D0422), L-methionine (M5308), L-cystine (C7602), 2-Mercaptoethanol (M3148) and Phorbol 12-myristate 13-acetate (P1585) were purchased from Sigma-Aldrich. 5-Ethynyl Uridine (EU) (E-10345), Homopropargylglycine (Hpg) (C10186), Alexa Fluor® 488 Azide (A10266), Click-iT® Cell Reaction Buffer Kit (C10269), DMEM medium (11965), FBS (10082), penicillin/streptomycin (15140), L-glutamine (25030), Neurobasal A Medium (10888) and B27 supplement (17504) were purchased from Invitrogen. RPMI-1640 Medium (30-2001) was purchased from ATCC. BCS (hyclone SH30072) was purchased from Fisher Scientific.

DMEM culture medium was made by adding 10% (vol/vol) FBS and 1% (vol/vol) penicillin/streptomycin to the DMEM medium. Methionine-deficient culture medium was made by supplying 4 mM L-glutamine, 0.2 mM L-cystine, 10% FBS and 1% penicillin/streptomycin to the DMEM medium without L-methionine, L-cystine and L-glutamine. RPMI-1640 culture medium was made of supplying the RPMI-1640 medium with 10% FBS, 1% penicillin/streptomycin and 50 µM 2-Mercaptoethanol. Neuron culture medium was made of Neurobasal A Medium adding with 1× B27 supplement and 0.5 mM glutamine. Culture medium for NIH3T3 cells was made by adding 10% (vol/vol) BCS and 1% (vol/vol) penicillin/streptomycin to the DMEM medium.

Propargylcholine synthesis. Propargylcholine was synthesized according to Jao, C. Y., Roth, M., Welti, R. & Salic, A. *Proc. Natl. Acad. Sci. USA* 106, 15332-15337 (2009). 3 mL propargyl bromide (80 wt. % solution in toluene) were added dropwise to 3 g 2-dimethylaminoethanol in 10 mL anhydrous THF on ice under argon gas protection and stirring. The ice bath was removed and the mixture was kept stirring at room temperature overnight. The white solids were filtered the next day and washed extensively with cold anhydrous THF to obtain 5 g pure propargylcholine bromide. All chemicals here are purchased from Sigma-Aldrich. NMR spectrum was recorded on a Bruker 400 (400 MHz) Fourier Transform (FT) NMR spectrometers at the Columbia University Chemistry Department. $^1$H NMR spectra are tabulated in the following order: multiplicity (s, singlet; d, doublet; t, triplet; m, multiplet), number of protons. $^1$H NMR (400 MHz, $D_2O$) δ ppm: 4.37 (d, J=2.4 Hz, 2H); 4.10 (m, 2H); 3.66 (t, J=4.8 Hz, 2H); 3.28 (s, 6H); MS (APCI+) m/z Calcd. for $C_7H_{14}NO$ $[M]^+$:128.19. Found: 128.26.

Sample preparation for SRS imaging of live cells and organisms. For all SRS imaging experiments of HeLa cells (e.g. FIG. 12), cells were first Seeded on coverslips with a density of 1×10$^5$/mL in petri dishes with 2 mL DMEM culture medium for 20 h at 37° C. and 5% $CO_2$.

1) EdU experiment, DMEM culture medium was then changed to DMEM medium (FBS-free) for 24 h for cell cycle synchronization. After synchronization, medium was replaced back to DMEM culture medium and EdU (10 mM stock in PBS) was simultaneously added to a concentration of 100 µM for 15 h.
2) EU experiment, EU (100 mM stock in PBS) was added to the DMEM culture medium directly to a concentration of 2 mM for 7 h.
3) Hpg experiment, DMEM culture medium was then changed to methionine-deficient culture medium for 1 h, followed by supplying 2 mM Hpg (200 mM stock in PBS) in the medium for 24 h.

4) Propargylcholine and EdU dual-color experiment, DMEM culture medium was changed to DMEM medium (FBS-free) for synchronization. After synchronization, medium was replaced back to DMEM culture medium by simultaneously adding both propargylcholine (25 mM stock in PBS) and EdU (10 mM stock in PBS) to the culture medium to a concentration of 1 mM and 100 µM, respectively, for 24 h.

For the propargylcholine experiment in neurons, hippocampal neurons were cultured on coverslips in 1 ml neuron culture medium for 14 d, and then propargylcholine (25 mM stock in PBS) is directly added into the medium to a final concentration of 1 mM for 24 h.

For the 17-ODYA experiment in macrophages, THP-1 cells were first Seeded on coverslips at a density of 2×105/mL in 2 ml RPMI-1640 culture medium for 24 h, followed by 72 h induction of differentiation to macrophages by incubating with 100 ng/ml Phorbol 12-myristate 13-acetate (PMA) in the medium. Medium was then replaced with RPMI-1640 culture medium containing 400 µM 17-ODYA (6:1 complexed to BSA) for 15 h.

For all of the above experiments, after incubation, the coverslip is taken out to make an imaging chamber filled with PBS for SRS imaging.

For the 17-ODYA experiment in *C. elegans*, OP50 bacterial culture was mixed well with 4 mM 17-ODYA (from 100 mM ethanol stock solution), and then Seeded onto nematode growth media (NGM) plates. After drying the plates in hood, wild type N2 day 1 adult *C. elegans* were placed onto the plates and fed for 40 h. *C. elegans* were then mounted on 2% agarose pads containing 0.1% NaN3 as anesthetic on glass microscope slides for SRS imaging.

Figure 13:
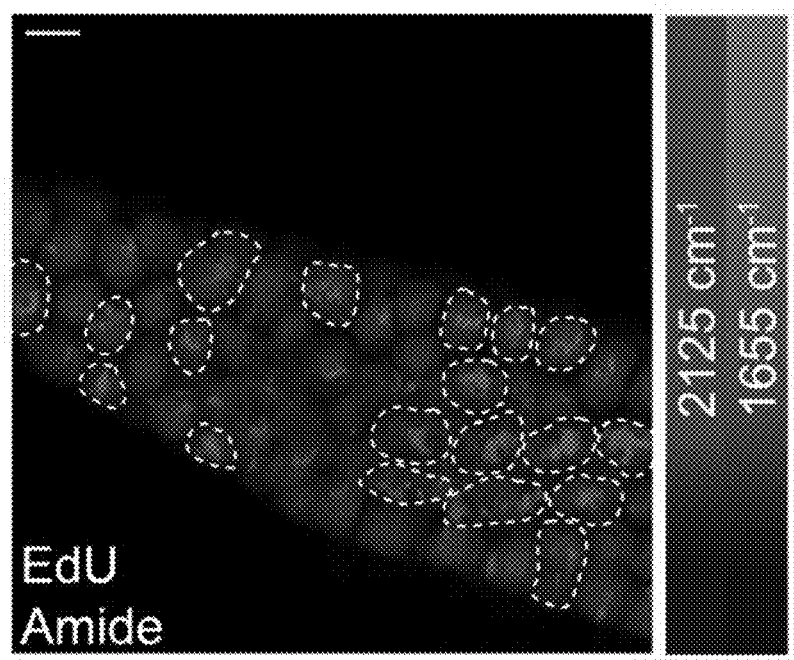
FIG. 13 shows SRS imaging of distal mitotic region of C. elegans germline incorporated with EdU. The composite image shows both the protein derived 1655 cm$^{-1}$ (amide) signal from all the germ cells, and the direct visualization of alkynes (2125 cm$^{-1}$ (EdU)) highlighting the proliferating germ cells. White circles show examples of EdU positive germ cells in the mitotic region of C. elegans germline. Scale bar, 5 μm.

SRS imaging of *C. elegans* germline after feeding with EdU. MG1693 (thymidine defective MG1655) *E. Coli* strain was cultured in 2 ml LB medium at 37° C. overnight, and transferred to 100 ml of M9 medium containing 400 µM EdU for further growth at 37° C. for 24 h. The EdU-labeled MG1693 *E. Coli* was then Seeded on M9 agar plate. Synchronized day 1 adult worms developed in 20° C. were transferred to EdU-labeled bacterial plate for 3 h, and then were dissected to take out the germline for imaging (e.g. FIG. 13).

Figure 15:
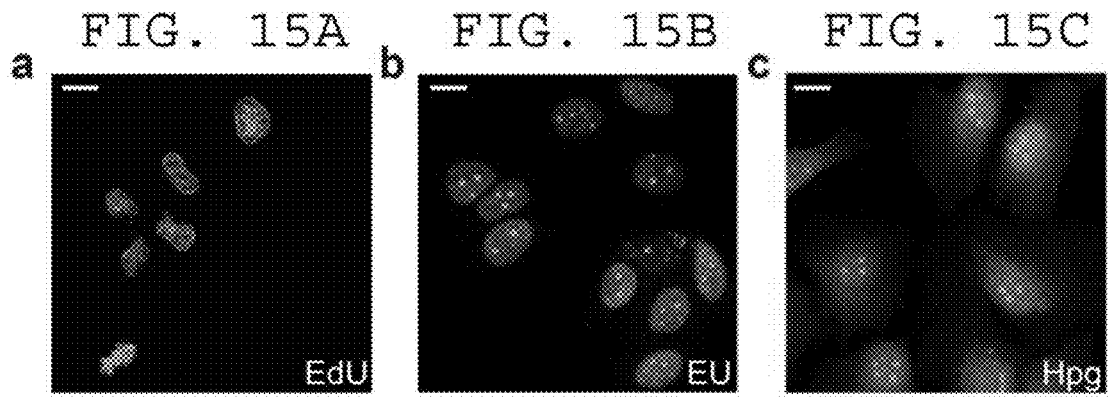
FIG. 15 shows click-chemistry based fluorescence staining of fixed HeLa cells. Fluorescence images of HeLa cells incorporated with FIG. 15a, EdU (for DNA)

Cell preparation for click chemistry-based fluorescence microscopy. All experiments (e.g. FIG. 15) were carried out following the manufacturer's protocol from Invitrogen. HeLa cells were first incubated with 10 µM EdU in DMEM culture medium for 24 h, or 1 mM EU in DMEM culture medium for 20 h, or 1 mM Hpg in methionine-deficient culture medium for 20 h, respectively. Cells were then fixed in 4% PFA for 15 min, washed twice with 3% BSA in PBS, permeabilized with 0.5% Triton PBS solution for 20 min, and performed click chemistry staining using Alexa Fluor 488 Azide in the Click-iT Cell Reaction Buffer Kit for 30 min. After washing with 3% BSA in PBS for three times, fluorescence images were obtained using an Olympus FV1200 confocal microscope with 488 nm laser excitation while the cells were immersed in PBS solution.

Figure 16:
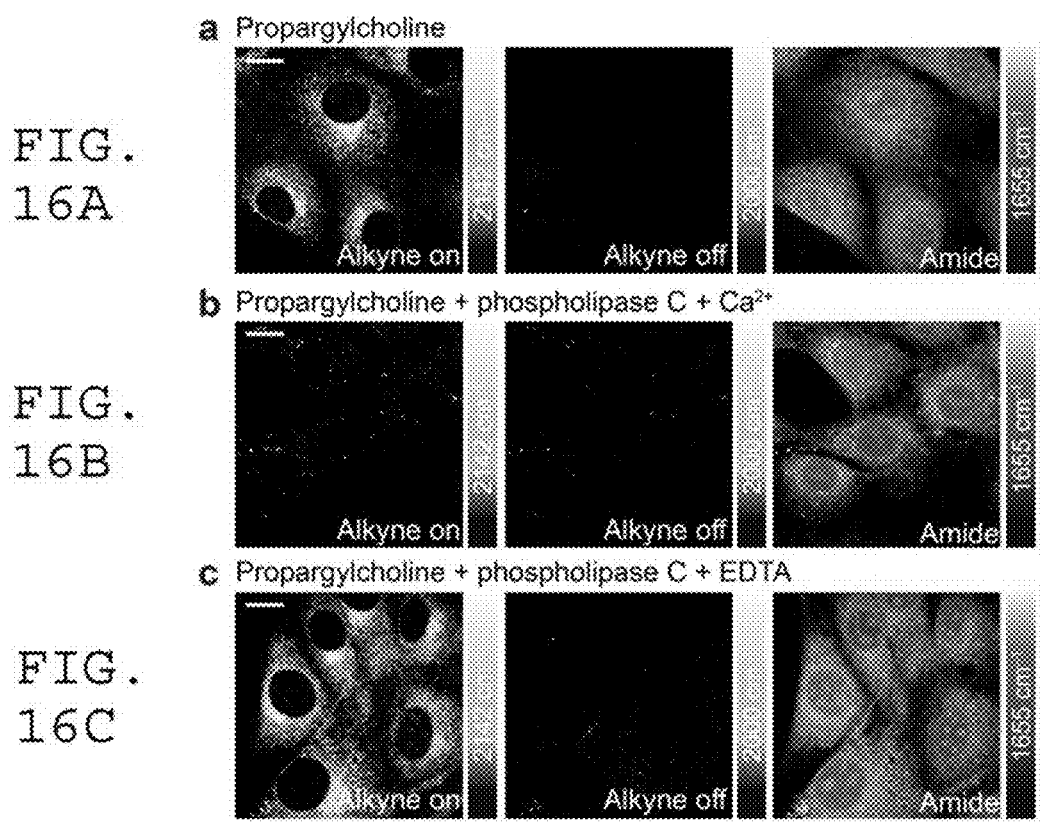
FIG. 16 shows SRS imaging of propargylcholine incorporation in NIH3T3 cells and control experiments. For example.

Enzymatic assays confirming propargylcholine incorporation into cellular choline phospholipids. We design our control experiments according to the click chemistry based assays reported in Jao, C. Y., Roth, M., Welti, R. & Salic, A. Proc. Natl. Acad. Sci. USA 106, 15332-15337 (2009) (e.g. FIG. 16). NIH 3T3 cells cultured with 0.5 □M propargylcholine for 48 hours were fixed with 4% PFA for 15 minutes, rinsed with 1 mL TBS buffer twice and incubated with 1 mL 1 mg/mL BSA in TBS buffer for 1 hour at 37° C., with or without 0.02 U/mL phospholipase C (Type XIV from *Clostridium perfringens*, Sigma), in the presence of 10 mM $CaCl_2$) (required for phospholipase C activity) (e.g. FIG. 16b) or 10 mM EDTA (e.g. FIG. 16c). The cells were then washed with TBS buffer and ready for SRS imaging.

Figure 17:
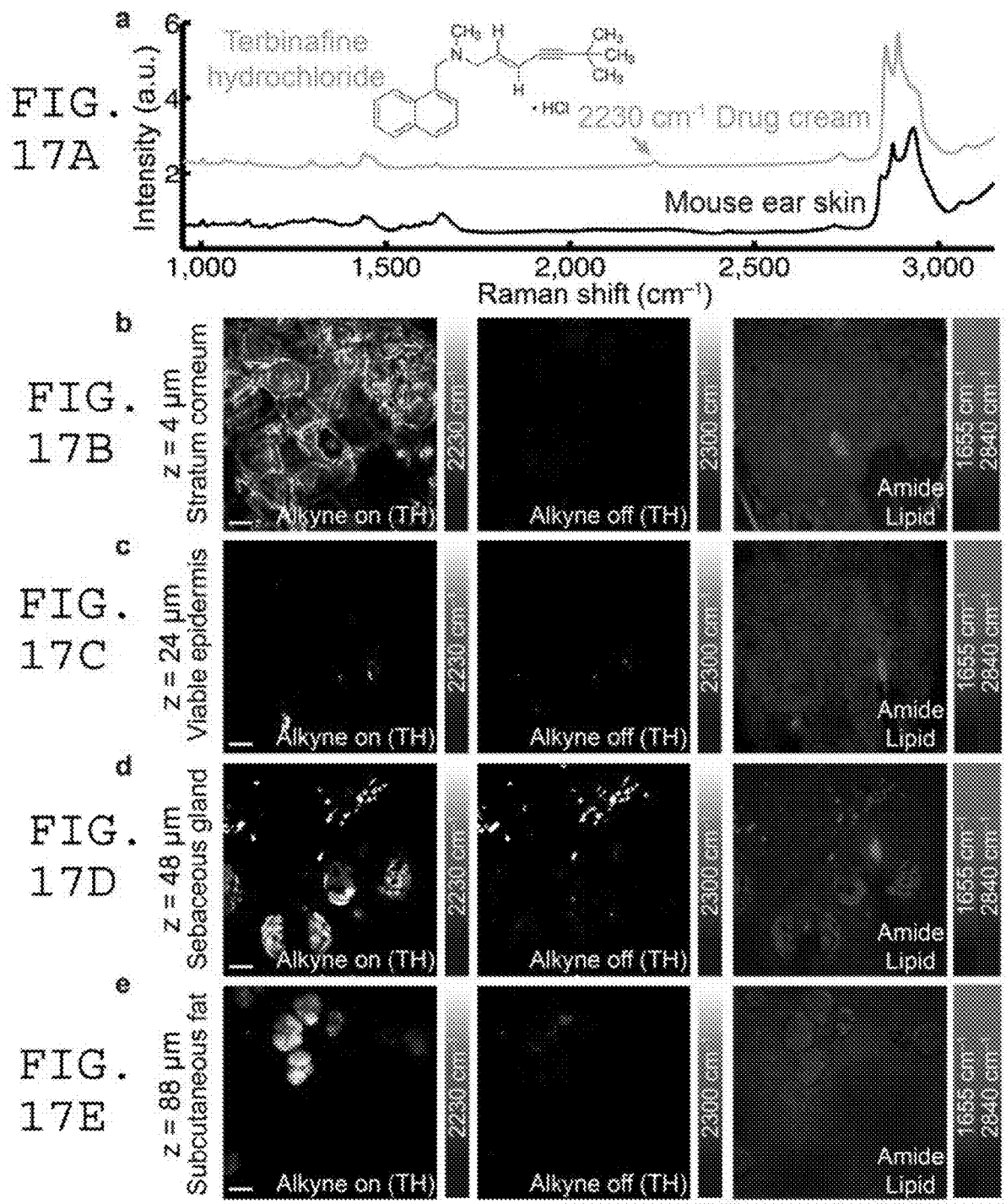
FIG. 17 shows in vivo delivery of an alkyne-bearing drug (TH in DMSO) into mouse ear. For example.

Sample preparation for drug delivery into mouse ear tissues. Either DMSO solution or Drug cream (Lamisil, Novartis) containing 1% (w/w) active terbinafine hydrochloride (TH) was applied to the ears of an anesthetized live mouse (2-3 weeks old white mouse of either sex) for 30 min, and the dissected ears from the sacrificed mouse were then imaged by SRS (e.g. FIGS. 17 and 18). The amide (1655 $cm^{-1}$) and lipid (2845 $cm^{-1}$) images have been applied with linear spectral unmixing to eliminate cross talk before composition. The experimental protocol for drug delivery on mice (AC-AAAG4703) was approved by Institutional Animal Care and Use Committee at Columbia University.

Image progressing. Images are acquired with FluoView scanning software and assigned color or overlaid by ImageJ. Graphs were assembled with Adobe Illustrator.

Example 2a: Alkyne Tags

As an effective imaging modality for small biomolecules, we report a general strategy of using stimulated Raman scattering (SRS) microscopy to image alkynes (i.e., C≡C) as nonlinear vibrational tags, shown as bond-selective SRS in FIGS. 10a-c. As shown in FIG. 10a, Spontaneous Raman spectra of HeLa cells and 10 mM EdU solution. Inset: the calculated SRS excitation profile (FWHM 6 $cm^{-1}$, element 905) is well fitted within the 2125 $cm^{-1}$ alkyne peak (FWHM 14 $cm^{-1}$, magenta). FIG. 10b shows linear dependence of stimulated Raman loss signals (2125 $cm^{-1}$) with EdU concentrations under a 100 s acquisition time. FIG. 10c shows the metabolic incorporation scheme for a broad spectrum of alkyne-tagged small precursors. a.u. arbitrary units. Alkynes possess desirable chemical and spectroscopic features. Chemically, they are small (only two atoms), exogenous (nearly non-existent inside cells), and bioorthogonal (inert to reactions with endogenous biomolecules). These properties render alkynes key players in bioorthogonal chemistry, in which precursors labeled with alkyne tags form covalent bonds with azides fused to probes such as fluorophores for detection. However, such a 'click-chemistry' approach prohibits live imaging, as it usually involves a copper-catalyzed reaction that requires cell fixation, while the copper-free version has slow kinetics and high background. Spectroscopically, the C≡C stretching motion exhibits a substantial change of polarizability, displaying a sharp Raman peak around 2125 $cm^{-1}$, which lies in a desirable cell-silent spectral region[13] (FIG. 10a). Compared to the popular carbon-deuterium (C-D) Raman tag, alkynes produce about 40 times higher peaks. However the signal is still relatively weak and extremely long acquisition times (~49 min per frame consisting of 127×127 pixels) limit dynamic imaging in live systems.

Figure 11:
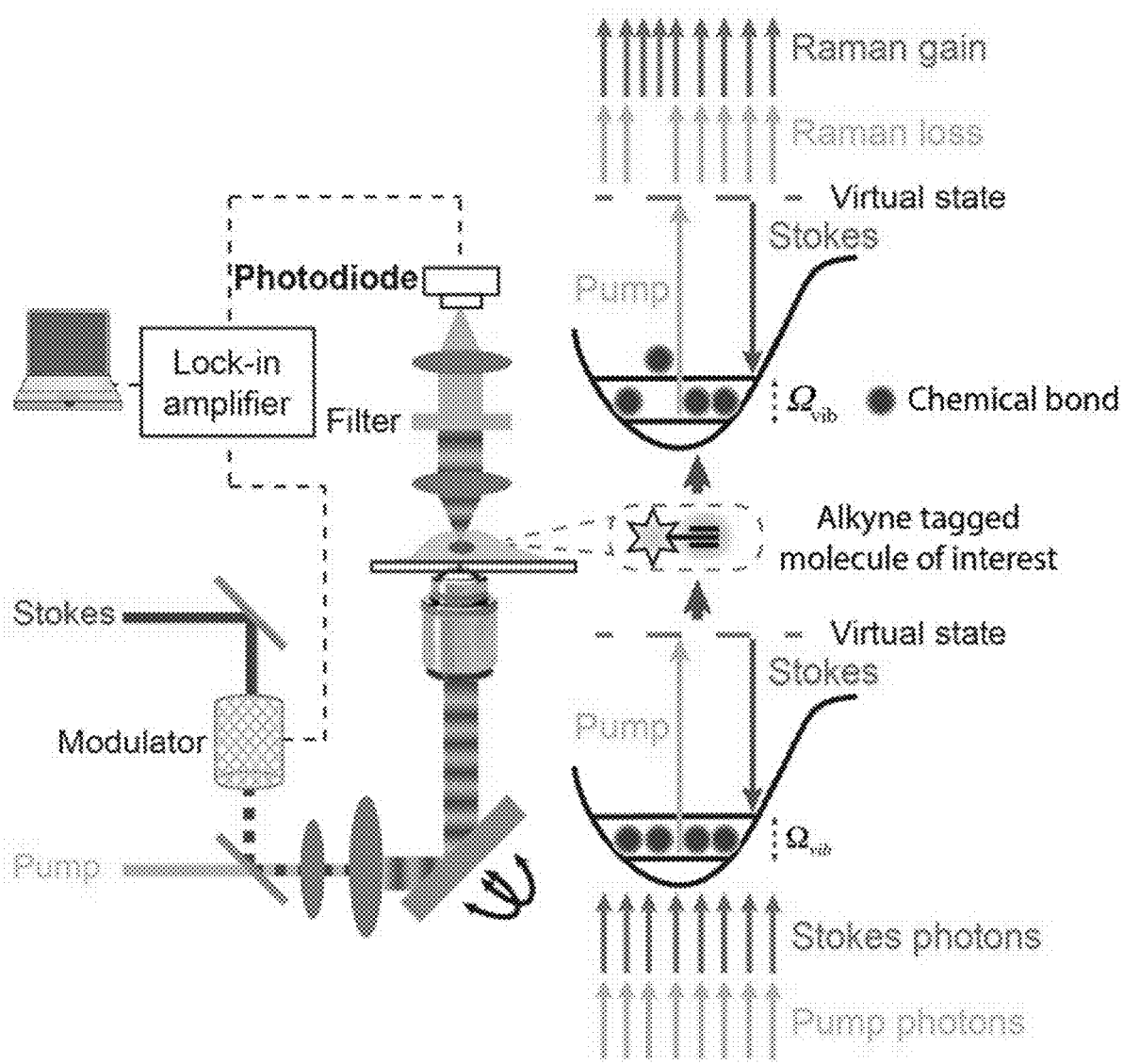
FIG. 11 illustrates the working mechanism of a stimulated Raman scattering with A Pump beam (pulsed, pico-second) and an intensity-modulated Stokes beam (pulsed, pico-second). The Pump beam (pulsed, pico-second) and an intensity-modulated Stokes beam (pulsed, pico-second) are both temporally and spatially synchronized before focused onto cells that have been metabolically labeled with alkyne-tagged small molecules of interest. When the energy difference between the Pump photon and the Stokes photon matches the vibrational frequency ($\Omega_{vib}$) of alkyne bonds, alkyne bonds are efficiently driven from their vibrational ground state to their vibrational excited state, passing through a virtual state. For each excited alkyne bond, a photon in the Pump beam is annihilated (Raman loss) and a photon in the Stokes beam is created (Raman gain). The detected pump laser intensity changes through a lock-in amplifier targeted at the same frequency as the modulation of Stokes beam serve as the contrast for alkyne distributions.

The coupling of SRS microscopy to alkyne tags that we report offers sensitivity, specificity and biocompatibility for probing complex living systems. When the energy difference between incident photons from two lasers (pump and Stokes) matches with the 2125 cm-1 mode of alkyne vibrations, their joint action will greatly accelerate the vibrational excitation of alkyne bonds. As a result of energy exchange between the input photons and alkynes, the output pump and Stokes beams will experience intensity loss and gain, respectively. Such intensity changes measured by SRS microscopy generate concentration-dependent alkyne distributions in three-dimensions (3D). FIG. 11 is an illustration showing a Pump beam (pulsed, pico-second) and an intensity-modulated Stokes beam (pulsed, pico-second) are both temporally and spatially synchronized before focused onto cells that have been metabolically labeled with alkyne-tagged small molecules of interest. When the energy difference between the Pump photon and the Stokes photon matches the vibrational frequency ($\Omega$vib) of alkyne bonds, alkyne bonds are efficiently driven from their vibrational ground state to their vibrational excited state, passing through a virtual state. For each excited alkyne bond, a photon in the Pump beam is annihilated (Raman loss) and a photon in the Stokes beam is created (Raman gain). The detected pump laser intensity changes through a lock-in amplifier targeted at the same frequency as the modulation of Stokes beam serve as the contrast for alkyne distributions.

SRS microscopy offers a number of advantages. First, SRS boosts vibrational excitation by a factor of 107, rendering a quantum leap of sensitivity (i.e., detectability and speed) over spontaneous Raman. Second, we use a 6-ps pulse width to match the excitation profile of alkyne (e.g. FIG. 10a), assuring efficient and selective nonlinear excitation. Third, SRS is free of background, whereas spontaneous Raman suffers from auto-fluorescence and coherent anti-stokes Raman scattering (CARS) suffers from non-resonant background 3. Finally, we employ near-infrared laser wavelengths for enhanced tissue penetration, intrinsic 3D sectioning (due to nonlinear excitation) and minimal phototoxicity.

We first detected the alkyne-tagged thymidine analogue 5-ethynyl-2'-deoxyuridine (EdU) in solution (e.g. FIG. 10b). Under a fast imaging speed of 100 s, we determined its detection limit to be 200 µM, corresponding to 12,000 alkynes within the laser focus. This approaches the shot-noise limit ($\Delta Ip/Ip \sim 2\times 10^{-7}$) of the pump beam, which represents the maximum theoretical sensitivity of the system. To explore the general applicability of our approach, we went on to examine a broad spectrum of small biomolecules including alkyne-tagged deoxyribonucleoside, ribonucleoside, amino acid, choline and fatty acid (FIG. 10c), whose metabolic incorporation has been thoroughly tested in bioorthogonal chemistry studies.

We imaged the metabolic uptake of EdU during de novo DNA synthesis. HeLa cells grown in media with EdU show a sharp Raman peak at 2125 cm-1 in the cell-silent region (e.g. FIG. 12a). Live-cell SRS imaging revealed EdU incorporation into the newly synthesized genomes of dividing cells (e.g. FIG. 12b, alkyne-on). Off-resonance images of the same cells, taken when the energy difference between pump and Stokes photons does not match vibrational peaks (alkyne-off), are background-free, confirming the purely chemical contrast of SRS. No EdU signal shows up in cells treated with the DNA synthesis inhibitor hydroxyurea, whereas lipids imaged at 2845 cm-1 verify that these cells are normal based on morphology. Moreover, we tracked dividing cells every 5 min during mitosis (e.g. FIG. 12c), demonstrating acquisition speed and compatibility with live dynamics that are nearly impossible with spontaneous Raman. We also showed that our method is applicable to multicellular organisms. Actively proliferating cells can be clearly distinguished in C. elegans grown in the presence of EdU as exemplified in FIG. 13, where the composite image shows both the protein derived 1655 cm-1 (amide) signal from all the germ cells, and the direct visualization of alkynes (2125 cm-1 (EdU)) highlighting the proliferating germ cells. White circles show examples of EdU positive germ cells in the mitotic region of C. elegans germline. Scale bar, 5 µm.

Next, we studied RNA transcription and turnover using the alkyne-tagged uridine analogue, 5-ethynyl uridine (EU)8 in HeLa cells (e.g. FIG. 12a). The alkyne-on image (e.g. FIG. 12d) reveals localized EU inside the nucleus with higher abundance in the nucleoli, which are major compartments of rRNA-rich ribosomal assembly, and nearly disappears in the presence of the RNA synthesis inhibitor actinomycin D. Turnover dynamics are further demonstrated by pulse-chase SRS imaging (FIG. 12e), which indicates a short nuclear RNA lifetime (~3 h) in live HeLa cells.

Figure 14:
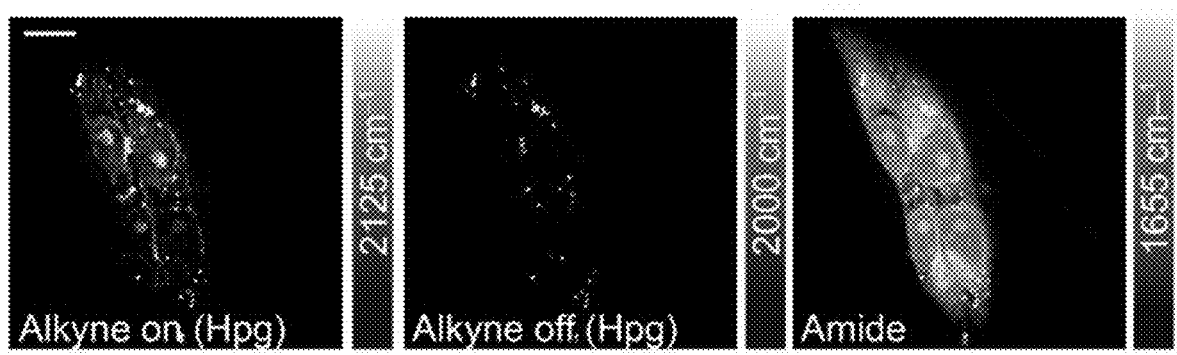
FIG. 14 shows SRS imaging of fixed HeLa cells after incorporating with 2 mM Hpg. The alkyne-on image displays the Hpg distribution for the newly synthesized proteins. For the same set of cells, the off-resonant (alkyne-off) image shows vanishing signal, and the amide image shows total protein distribution. This result confirms that the detected signal is not from freely diffusive precursor Hpg itself (which is eliminated during the fixation process). Scale bar, 10 μm.

Many intricate biological processes such as long-term memory require protein synthesis in a spatiotemporal dependent manner. We imaged L-Homopropargylglycine (Hpg), an alkyne-tagged analogue of methionine, to visualize newly synthesized proteomes. HeLa cells grown in methionine-deficient media supplemented with Hpg display an alkyne peak (e.g. FIG. 12a) about 20 times lower than that of 10 mM EdU solution (e.g. FIG. 10a). The corresponding alkyne-on image (e.g. FIG. 12f) shows the distribution of newly synthesized proteins with spatial enrichment in the nucleoli (arrow indicated), which experience rapid protein exchange. Similar to EdU in solution, the detection limit of alkynes in mammalian cells approaches 200 NM (with 100 µs pixel dwell time) based on an average signal-to-noise ratio of 2 as we obtained in HeLa cells. The Hpg signal is well retained in fixed cells (e.g. FIG. 14), indicating little contribution from freely diffusing Hpg. The alkyne-on image displays the Hpg distribution for the newly synthesized proteins. For the same set of cells, the off-resonant (alkyne-off) image shows vanishing signal, and the amide image shows total protein distribution. This result confirms that the detected signal is not from freely diffusive precursor Hpg itself (which is eliminated during the fixation process). Scale bar, 10 µm. Furthermore, adding methionine, which has a 500-fold-faster incorporation rate, to compete with Hpg causes the signal to disappear (e.g. FIG. 12f). Note that we verified the spatial patterns of EdU, EU and Hpg incorporation in live cells by performing click chemistry on fixed cells, with FIGS. 15A-C showing the fluorescence images of HeLa cells incorporated with a, EdU (for DNA); b, EU (for RNA); c, Hpg (for protein). Scale bars, 10 µm.

Lipid metabolism is critical for many functions in healthy and diseased tissues, but few non-perturbative tags are available to monitor lipids in the cell. We thus monitored the metabolic incorporation of alkyne-tagged choline and fatty acids. Hippocampal neurons grown on propargylcholine present a clear 2142 cm-1 Raman peak (e.g. FIG. 12a). Such a frequency shift from 2125 cm-1 is due to the positive charge on the nitrogen near the alkyne (FIG. 10c). As revealed by enzymatic assays (e.g. FIGS. 16a-16c), the alkyne-on signal (FIG. 12g) mainly originates from newly synthesized choline phospholipids at membranes. To label fatty acids, we incubated 17-octadecynoic acid (17-ODYA) with THP-1 macrophages, which actively scavenge cholesterol and fatty acids. In FIG. 16a, fixed NIH3T3 cells are seen after culturing with 0.5 mM propargylcholine for 48 hours. The alkyne-on image shows alkyne-tagged choline distribution. In FIG. 16b, treatment of fixed NIH3T3 cells with phospholipase C, which removes Choline head groups of phospholipids only in the presence of calcium. The alkyne-on image shows the strong decrease of incorporated propargylcholine signal, supporting its main incorporation into membrane phospholipids. For FIG. 16c, treatment of fixed NIH3T3 cells with phospholipase C in the presence of EDTA (chelating calcium). Propargylcholine signal is retained in the alkyne-on image. For FIGS. 16a-c: in the same set of cells as in alkyne-on images, the alkyne-off images show a clear background. The amide images display total protein distribution. Scale bars, 10 μm. The alkyne-on image (FIG. 12h) depicts the formation of numerous lipid droplets that indicates transformation into foam cells, a hallmark of early atherosclerosis. Multicellular organisms are also capable of taking up 17-ODYA for lipid imaging. New fatty acids in C. elegans appeared mainly inside lipid droplets upon SRS imaging, known to exist largely in the form of triglycerides (e.g. FIG. 12i). Such a fat accumulation process could serve as a useful model for studying obesity and diabetes. We were also able to perform dual-color imaging of propargylcholine (2142 cm-1) and EdU (2125 cm-1) incorporation due to the spectral sharpness and separation of their two alkyne peaks (FIG. 12j).

Finally, we tracked alkyne-bearing drug delivery (FIGS. 17a-e and 18a-b) in animal tissues by taking advantage of the intrinsic 3D sectioning property of SRS.

FIG. 17a depicts Raman spectra of a drug cream, Lamisil, containing 1% TH and mouse ear skin tissue. FIGS. 17b-e illustrate SRS imaging of tissue layers from stratum corneum (z=4 μm) to viable epidermis (z=24 μm), sebaceous gland (z=48 μm) and subcutaneous fat (z=88 μm). To facilitate tissue penetration, DMSO solution containing 1% TH was applied onto the ears of an anesthetized live mouse for 30 min and the dissected ears are imaged afterwards. For all 4 layers shown in FIGS. 17b-e, alkyne-on images display TH penetration; alkyne-off images show off-resonant background (The bright spots in d are due to two-photon absorption of red blood cells). The composite images show protein (1655 cm-1) and lipid (2845 cm-1) distributions. Scale bars, 20 μm. a.u.=arbitrary units.

FIGS. 18a-b show SRS imaging of the viable epidermis layer (z=20 μm) and the sebaceous gland layer (z=40 μm). For both a and b: the alkyne-on images display the TH penetration into mouse ear tissues through lipid phase. The composite images show both protein (1655 cm-1) and lipid (2845 cm-1) distributions. Scale bars, 20 μm.

Unlike bulky fluorophores, alkynes have little perturbation to pharmacokinetics and are common moieties in many pharmaceuticals. We chose terbinafine hydrochloride (TH), a US Federal Drug Administration approved alkyne-bearing antifungal skin drug, and imaged its drug delivery pathways inside mouse ear tissue to a depth of about 100 μm by targeting its internal alkyne at 2230 cm-1. TH images captured at various depths all exhibit patterns that highly resemble lipid distributions but not protein distributions, suggesting that TH penetrates into tissues through the lipid phase, consistent with its lipophilic nature. Our technique should be applicable to tracking other drugs after proper alkyne derivatization.

In conclusion, we report a general strategy to image small and biologically vital molecules in live cells by coupling SRS microscopy with alkyne vibrational tags. The major advantages of SRS lie in the superior sensitivity, specificity and compatibility with dynamics of live cells and animals. SRS imaging of alkynes may do for small biomolecules what fluorescence imaging of fluorophores has done for larger species.

Example 3: Synthesis of Bond-Edited Compounds

A. Synthesis of Alkyne-D-Glucose

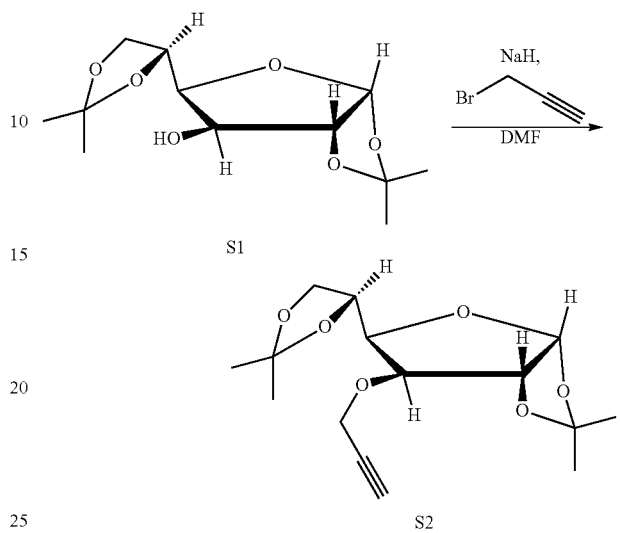

Sodium hydride (138 mg, 5.8 mmol) was added to a solution of 1,2:5,6-Di-O-isopropylidene-α-D-glucofuranose (Compound S1, 500 mg, 1.92 mmol, Aldrich D7600) in 10 mL dry DMF at 0° C. The solution was stirred at 0° C. for 30 min before propargyl bromide (80% in toluene, 0.43 mL, 3.84 mmol) was added dropwise. The reaction mixture was stirred at room temperature for 12 h before quenched with saturated ammonium chloride solution (10 mL). The mixture was extracted with ethyl acetate (2×25 mL), and the organic layer was combined, dried over anhydrous sodium sulfate, concentrated in vacuo, and purified by column chromatography on silica gel (0-50% Ethyl acetate in Hexanes) to give Compound S2 (518 mg, 90%) as a colorless oil. The 1H NMR spectrum is in accordance with previously published values (A. Hauserr et al., Synthesis, 2001, 1377).

1H NMR (400 MHz, CDCl3) δ 5.88 (d, J=3.6 Hz, 1H), 4.30-4.24 (m, 3H), 4.14 (dd, J=7.6, 2.8 Hz, 1H), 4.11-4.06 (m, 2H), 3.99 (dd, J=8.8, 5.6 Hz, 1H), 2.47 (t, J=2.4 Hz, 1H), 1.50 (s, 3H), 1.42 (s, 3H), 1.35 (s, 3H), 1.31 (s, 3H).

HRMS (FAB+) m/z Calcd. for $C_{15}H_{23}O_6$ $[M+H]^+$: 299.1495. Found: 299.1496.

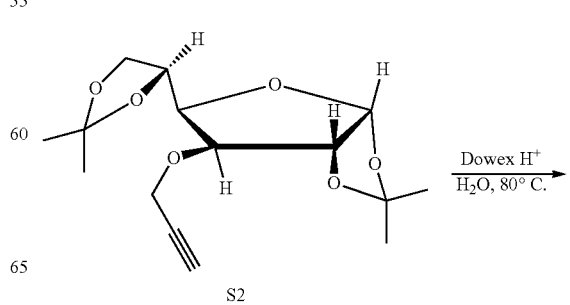

-continued

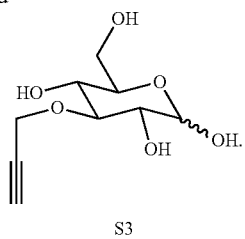

Water (10 mL) and Dowex® 50WX8 hydrogen form (600 mg, Sigma-Aldrich 217514) were added to Compound S2 (594 mg, 1.99 mmol). The mixture was heated to 80° C. for 20 h before filtered. The filtrate was concentrated in vacuo to give Compound S3 (416 mg, 1.91 mmol, 96%) as a white solid.

1H NMR (400 MHz, D2O) δ 5.13 (d, J=3.6 Hz, 1H), 4.44 (d, J=2.4 Hz, 2H), 3.79-3.73 (m, 2H), 3.70-3.61 (m, 2H), 3.51 (dd, J=9.8, 3.8 Hz 1H), 3.40 (t, J=9.6 Hz, 1H), 2.82 (s, 1H). 13C NMR (101 MHz, D2O) δ 92.1, 80.8, 79.8, 75.9, 71.4, 71.2, 69.2, 60.4, 59.9.

HRMS (FAB+) m/z Calcd. for C9H14O6Na [M+Na]+: 241.0688. Found: 241.0683.

B. Synthesis of EdU-$^{13}$C (Compound 2) and EdU-$^{13}$C2 (Compound 3)

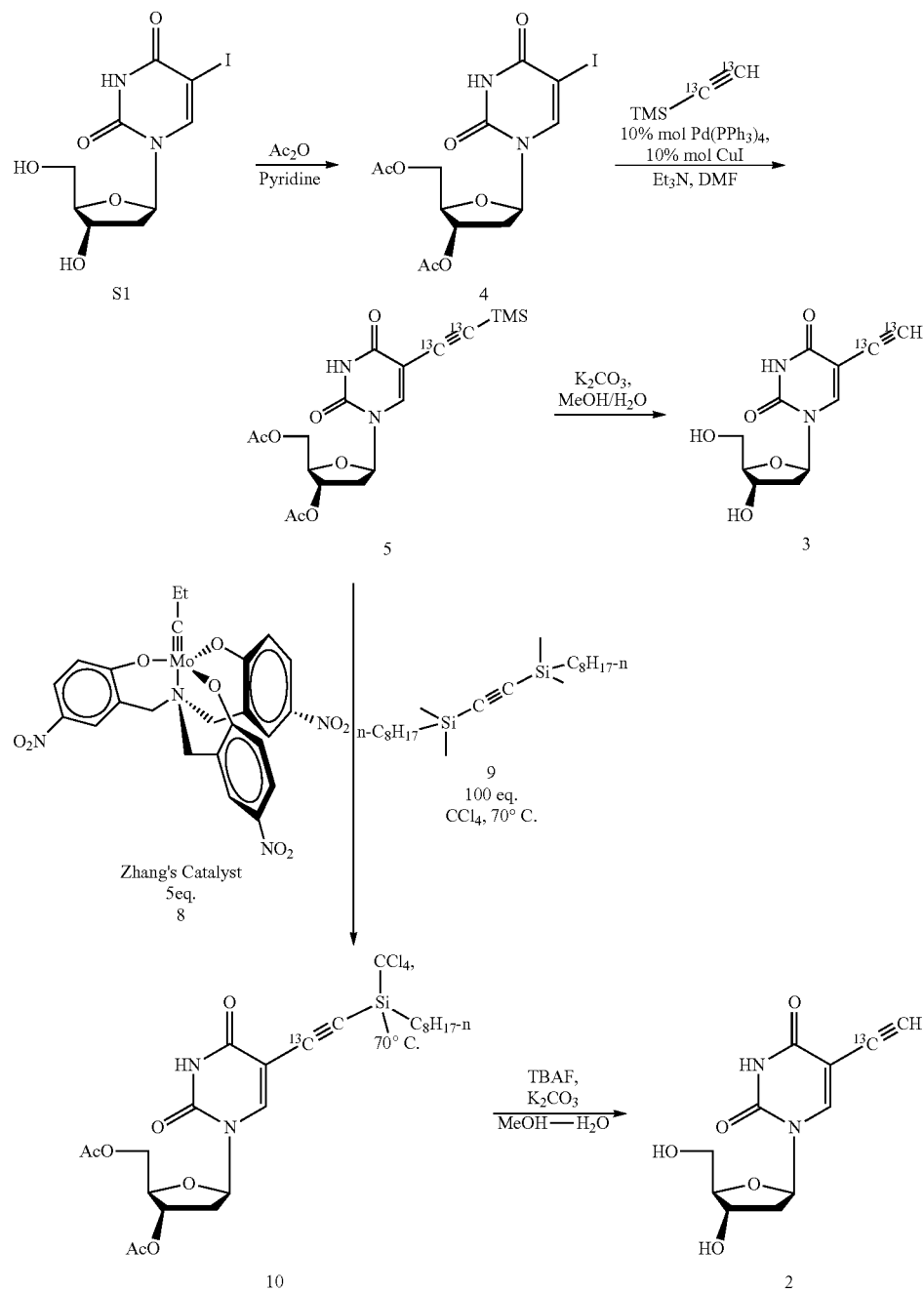

Synthesis of Compound 4:

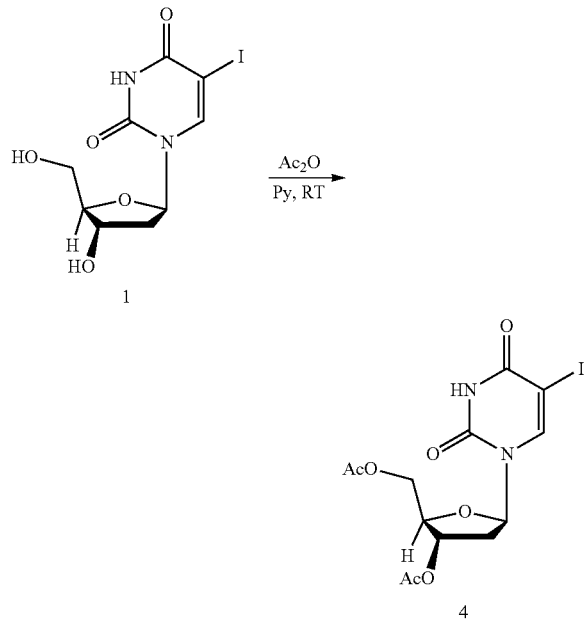

To a solution of 5-iodo-2'-deoxyuridine (Compound 1, 150 mg, 0.42 mmol) in 1.5 ml of pyridine was added 0.4 ml (0.42 mmol) acetic anhydride at 0° C. The resulting mixture was warmed up to room temperature and stirred for 4 h, then poured into 5 ml of cold 1 N NaHSO$_4$ and extracted with ethyl acetate three times. The organic layer was washed with saturated NaHCO$_3$ and brine, dried over anhydrous Na$_2$SO$_4$ and concentrated. The crude product was purified by column chromatography on silica gel (0-70% Ethyl acetate in Hexanes) to give Compound 4 (157.3 mg, 0.36 mmol, 85%) as a white solid.

1H NMR (400 MHz, CDCl3) δ ppm: 8.46 (s, 1H), 7.97 (s, 1H), 6.28 (dd, J=8.2, 5.7 Hz, 1H), 5.27-5.19 (m, 1H), 4.41 (dd, J=12.3, 3.2 Hz, 1H), 4.34 (dd, J=12.3, 2.9 Hz, 1H), 4.30 (q, J=2.9 Hz, 1H), 2.54 (ddd, J=14.3, 5.7, 2.1 Hz, 1H), 2.21 (s, 3H), 2.20-2.13 (m, 1H), 2.12 (s, 3H).

MS (APCI+) m/z Calcd. for C13H16IN2O7 [M+H]$^+$: 439.0. Found: 438.8.

Synthesis of Compound 5:

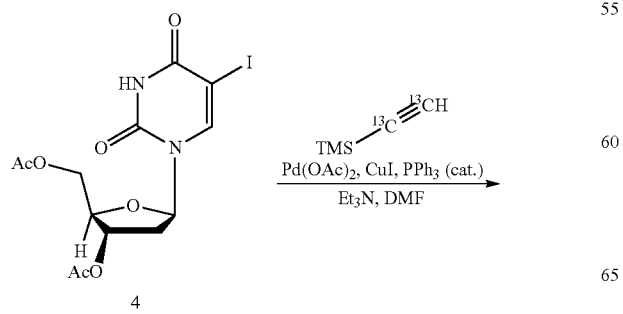

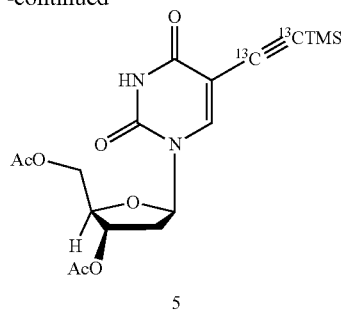

To an oven-dried vial was added Compound 4 (72 mg, 164 μmol), Pd (OAc)2 (3.6 mg, 16 μmol), PPh3 (8.6 mg, 33 μmol), CuI (3.1 mg, 16 μmol), DMF (2 ml), Et3N (50 mg, 69 μl, 492 μmol) and TMS13C≡13CH (25 mg, 250 μmol) under Ar. The yellow mixture was stirred at RT for 15 h before concentrated in vacuo. The residue was purified by column chromatography on silica gel (0-70% Ethyl acetate in Hexanes) to give Compound 5 (48.4 mg, 118 μmol, 72%) as a thin film.

1H NMR (400 MHz, Methanol-d4) δ 7.98 (d, J=5.0 Hz, 1H), 6.23 (dd, J=7.8, 6.0 Hz, 1H), 5.28 (dt, J=6.7, 2.6 Hz, 1H), 4.36 (t, J=3.1 Hz, 2H), 4.34-4.28 (m, 1H), 2.50 (ddd, J=14.5, 6.0, 2.5 Hz, 1H), 2.39 (ddd, J=14.5, 7.9, 6.6 Hz, 1H), 2.16 (s, 3H), 2.09 (s, 3H), 0.20 (d, J=2.5 Hz, 9H). 13C NMR (101 MHz, MeOD) δ 99.54 (d, J=140.5 Hz), 96.95 (d, J=140.5 Hz).

MS (APCI+) m/z Calcd. for C1613C2H25N2O7Si [M+H]$^+$: 411.2. Found: 411.0.

Synthesis of Compound 3:

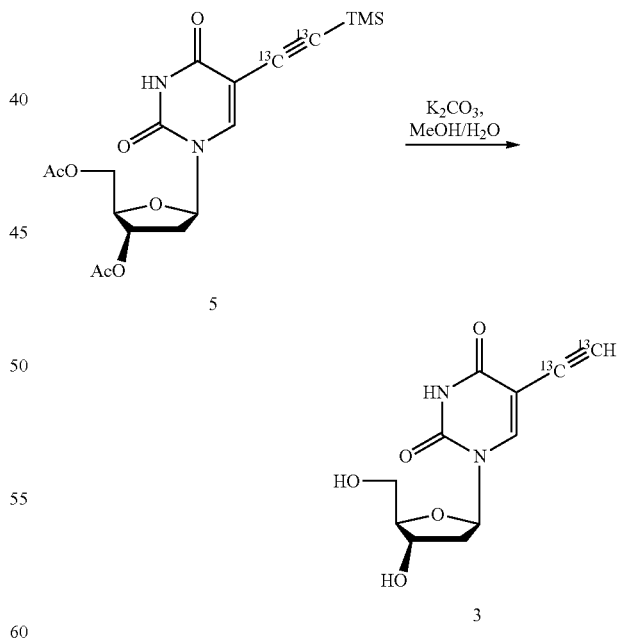

To a solution of Compound 5 (3.5 mg, 8.5 μmol) in 0.9 ml MeOH and 0.1 ml H2O was added K2CO3 (6.0 mg, 43 μmol) at RT. The reaction was stirred overnight before concentrated in vacuo. The residue was purified by reverse phase HPLC to give compound 3 (1.6 mg, 6.4 μmol, 75%) as a thin film.

HPLC condition: 20 min gradient elution using H2O: MeCN starting from 100:0 to 85:15. Retention time: 15.4 min 1H NMR (400 MHz, MeOD) δ: 8.39 (d, J=5.6 Hz, 1H); 6.24 (t, J=6.4 Hz, 1H); 4.40 (m, 1H); 3.94 (dd, J=6.4, 3.2 Hz, 1H); 3.82 (dd, J=12, 3.2 Hz, 1H); 3.73 (dd, J=12, 3.6 Hz, 1H); 3.53 (dd, J=250.4, 54.8 Hz, 1H); 2.32 (ddd, J=13.6, 6, 3.6 Hz, 1H); 2.23 (m, 1H). 13C NMR (101 MHz, MeOD) δ 82.87 (d, J=180.4 Hz), 75.85 (d, J=180.3 Hz).

MS (FAB+) m/z Calcd. for C9 13C2H13N2O5 [M+H]*: 255.09. Found: 255.11.

Synthesis of Compound 9:

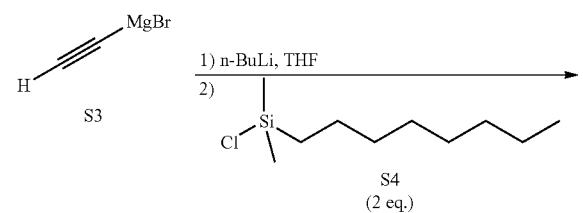

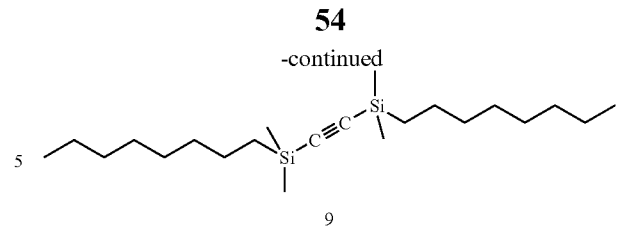

To a solution of ethynylmagnesium bromide in THF (5.0 ml, 0.5 M solution, 2.5 mmol) was added 15 ml THF under Ar. The solution was cooled to −78° C. and 2.4 ml n-BuLi in hexane (1.6 M, 3.8 mmol) was added dropwisely. After 30 min, chloro(dimethyl)octylsilane (1.21 ml, 1.06 g, 5.1 mmol) was added dropwisely. The reaction was then warmed to RT and stirred for another 3 h before filtered through a short pad of silica. The solvent was removed under reduced pressure and the residue was purified by column chromatography on silica gel (pure Hexanes) to give Compound 9 (885 mg, 2.4 mmol, 96%) as a colorless liquid.

1H NMR (400 MHz, Chloroform-d) δ 1.42-1.24 (m, 24H), 0.88 (t, J=6.6 Hz, 6H), 0.60 (dd, J=9.4, 6.2 Hz, 4H), 0.13 (s, 12H). 13C NMR (101 MHz, Chloroform-d) δ 113.94, 33.37, 32.12, 29.49, 29.43, 23.92, 22.85, 16.26, 14.27, −1.55.

HRMS (EI+) m/z Calcd. for C22H46Si2 [M]+:366.3138. Found: 366.3134.

Synthesis of Compound 10:

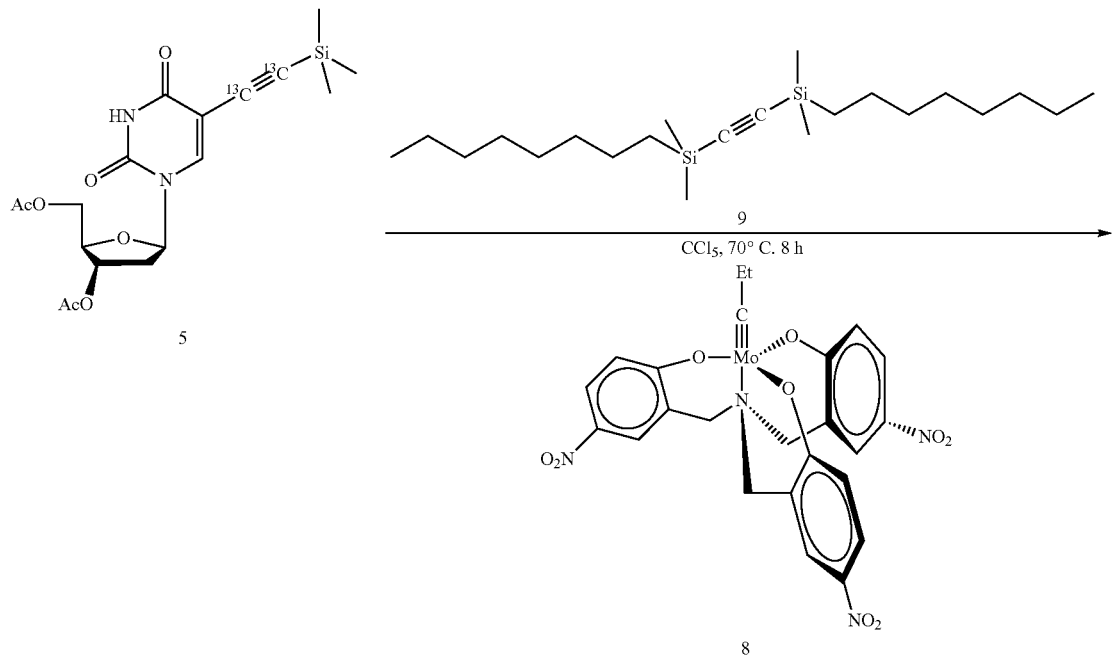

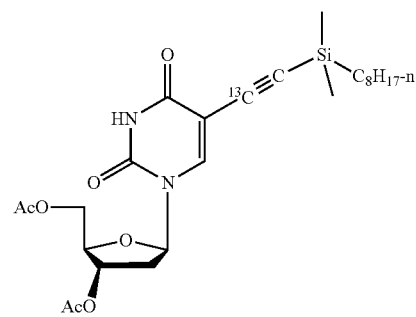

In a glove box filled with Ar, catalyst 8 (36.5 µmol, 5 eq.) was prepared in 0.5 mL dry CCl4 in situ according to the procedure documented by Jyothish and Zhang (Angew. Chem. Int. Ed. Engl. 50, 3435-8 (2011)). To the solution of catalyst 8 in CCl4 was added 9 (267 mg, 0.73 mmol) and a solution of Compound 5 (3.0 mg, 7.3 µmol) in 0.5 mL dry CCl4. The mixture was heated to 70° C. for 8 h before concentrated in vacuo. The residue was purified by column chromatography on silica gel (0-70% Ethyl acetate in Hexanes) to recover Compound 5 (0.5 mg, 1.2 µmol) and to give Compound 10 (1.0 mg, 2.0 µmol, 27%, 33% B.R.S.M.) as a thin film.

1H NMR (400 MHz, Methanol-d4) δ 7.97 (d, J=5.6 Hz, 1H), 6.23 (dd, J=7.9, 5.9 Hz, 1H), 5.28 (dt, J=6.8, 2.4 Hz, 1H), 4.36 (dd, J=5.8, 3.4 Hz, 2H), 4.31 (dd, J=6.3, 3.2 Hz, 1H), 2.50 (ddd, J=14.5, 6.1, 2.5 Hz, 1H), 2.38 (ddd, J=20.2, 7.7, 6.1 Hz, 1H), 2.15 (s, 3H), 2.09 (s, 3H), 1.30 (s, 12H), 0.90 (t, J=6.9 Hz, 3H), 0.70-0.62 (m, 2H), 0.18 (s, 6H). 13C NMR (101 MHz, MeOD) δ 97.56.

MS (FAB+) m/z Calcd. for C2413CH38N2NaO7Si [M+Na]+: 530.24. Found: 530.25.

Synthesis of Compound 2:

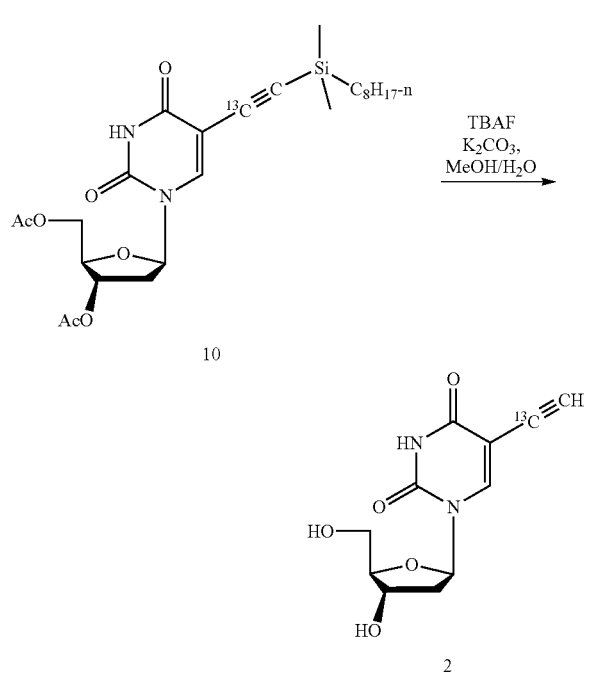

To a solution of compound 10 (0.4 mg, 0.8 µmol) in 0.5 ml MeOH and 0.05 ml H2O was added K2CO0 (2.0 mg, 14 µmol) and TBAF (20 µL, 1 M in THF) at RT. The reaction was stirred 7 h at RT before concentrated in vacuo. The residue was purified by reverse phase HPLC to give compound 2 (0.1 mg, 0.4 µmol, ~50%) as a thin film.

HPLC condition: 20 min gradient elution using H2O: MeCN starting from 100:0 to 85:15. Retention time: 15.4 min The mass of the product is determined by UV-Vis (λabs=288 nm, ε=12,000 cm-1M-1 in methanol).

1H NMR (500 MHz, Methanol-d4) δ 8.39 (d, J=5.7 Hz, 1H), 6.24 (t, J=6.5 Hz, 1H), 4.40 (dt, J=6.6, 3.6 Hz, 1H), 3.94 (q, J=3.3 Hz, 1H), 3.82 (dd, J=12.0, 3.1 Hz, 1H), 3.73 (dd, J=12.0, 3.4 Hz, 1H), 3.53 (d, J=51.3 Hz, 1H), 2.32 (ddd, J=13.6, 6.2, 3.7 Hz, 1H), 2.27-2.17 (m, 1H). 13C NMR (101 MHz, MeOD) δ 76.00. MS (ESI+) m/z Calcd. for C1013CH13N2O5 [M+H]+: 254.09. Found: 254.70.

Synthesis of EU-C$^{13}$C$_2$ (Compound 13)

Synthesis of S6:

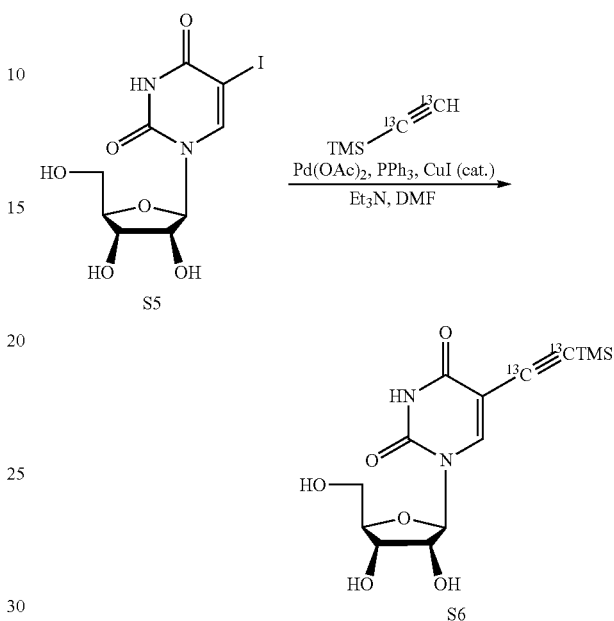

To an oven-dried vial was added compound S5 (15 mg, 50 µmol), Pd(OAc)2 (1.1 mg, 5 mol), PPh3 (2.6 mg, 10 µmol) CuI (1.0 mg, 5 µmol), DMF (1 ml), Et3N (15 mg, 20.7 µl, 150 umol) and TMS13C≡13CH (7.5 mg, 10.8 µl, 75 µmol) under Ar. The mixture was stirred at RT for 12 h before concentrated in vacuo. The residue was purified by column chromatography on silica gel (0-50% methanol in dichloromethane) to give compound S6 (9.0 mg, 26 µmol, 52%) as a thin film.

1H NMR (400 MHz, Methanol-d4) δ 8.41 (d, J=4.9 Hz, 1H), 5.91-5.83 (m, 1H), 4.21-4.13 (m, 2H), 4.07-3.98 (m, 1H), 3.88 (dd, J=12.2, 2.6 Hz, 1H), 3.75 (dd, J=12.2, 2.8 Hz, 1H), 0.20 (d, J=2.3 Hz, 9H). 13C NMR (101 MHz, MeOD) δ 99.24 (d, J=141.0 Hz), 96.95 (d, J=141.0 Hz).

MS (FAB+) m/z Calcd. for C1213C2H21N2O6Si [M+H]+: 343.12. Found: 343.17.

Synthesis of Compound 13:

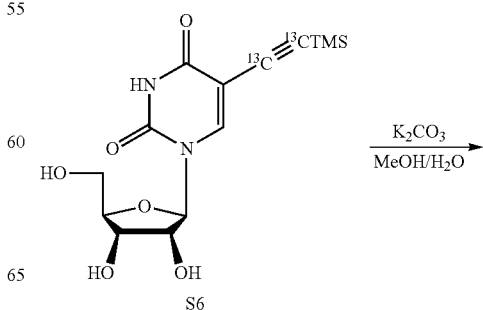

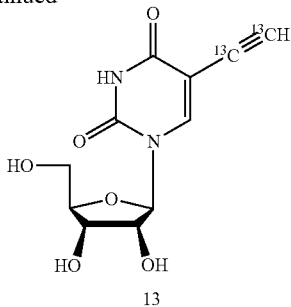

13

To a solution of compound S6 (3.0 mg, 8.8 µmol) in 0.6 ml MeOH and 0.1 ml H2O was added K2CO3 (5.0 mg, 36 µmol) at RT. The reaction was stirred overnight before concentrated in vacuo. The residue was purified by reverse phase HPLC to give compound 13 (2.2 mg, 8.1 µmol, 92%) as a thin film.

1H NMR (400 MHz, Methanol-d4) δ 8.47 (d, J=5.6 Hz, 1H), 5.93-5.83 (m, 1H), 4.21-4.13 (m, 2H), 4.06-3.98 (m, 1H), 3.88 (dd, J=12.2, 2.6 Hz, 1H), 3.75 (dd, J=12.2, 2.8 Hz, 1H), 3.54 (dd, J=250.4, 54.6 Hz). 13C NMR (101 MHz, MeOD) δ 82.90 (d, J=180.2 Hz), 75.74 (d, J=180.2 Hz).

MS (ESI+) m/z Calcd. for C913C2H13N2O6 [M+H]+: 271.08. Found: 271.51.

Figure 38:
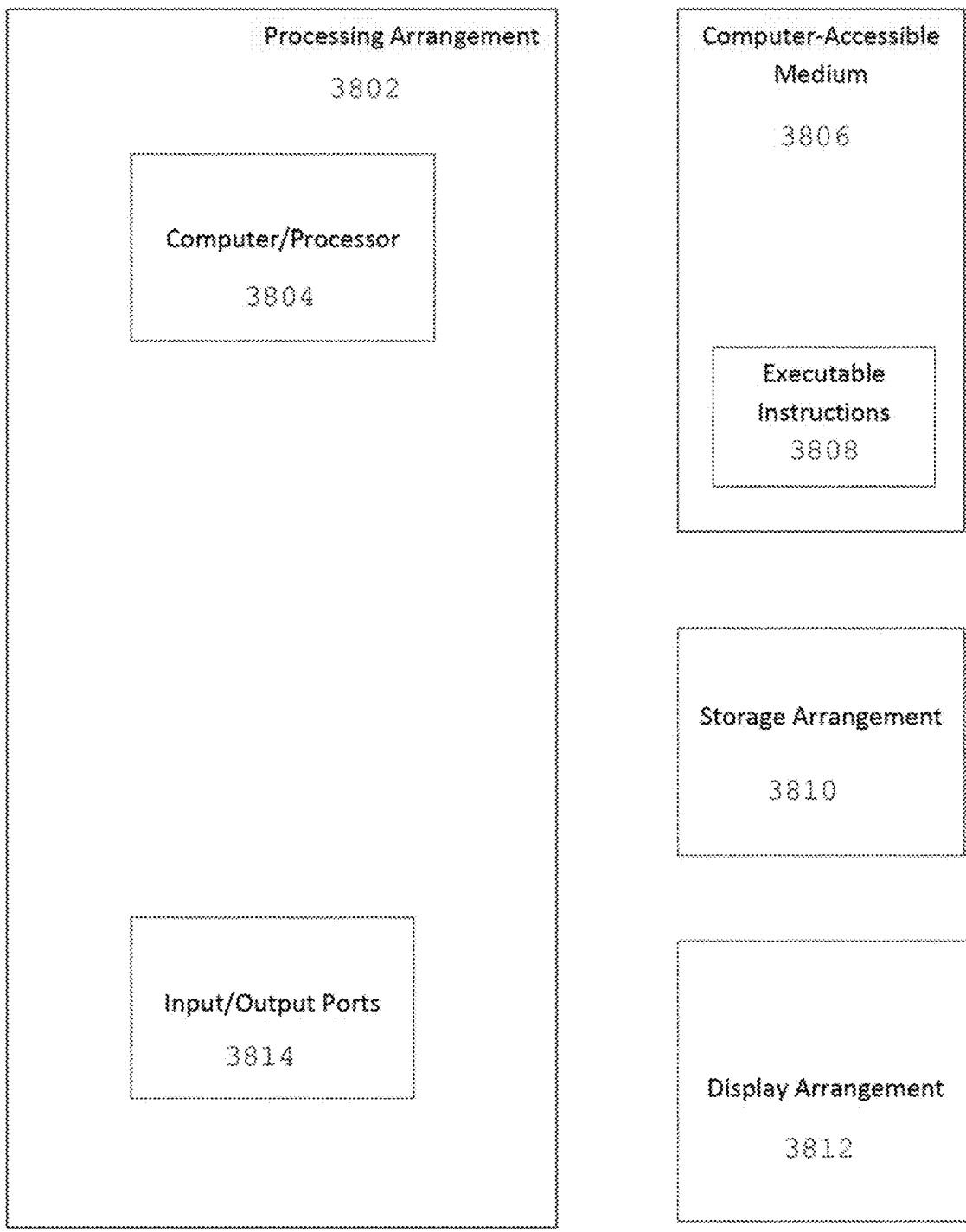
FIG. 38 is an illustration of an exemplary block diagram of an exemplary system in accordance with certain exemplary embodiments of the present disclosure.

FIG. 38 shows a block diagram of an exemplary embodiment of a system according to the present disclosure. For example, exemplary procedures in accordance with the present disclosure described herein can be performed by a processing arrangement and/or a computing arrangement 3802. Such processing/computing arrangement 3802 can be, for example entirely or a part of, or include, but not limited to, a computer/processor 3804 that can include, for example one or more microprocessors, and use instructions stored on a computer-accessible medium (e.g., RAM, ROM, hard drive, or other storage device).

As shown in FIG. 38, for example a computer-accessible medium 3806 (e.g., as described herein above, a storage device such as a hard disk, floppy disk, memory stick, CD-ROM, RAM, ROM, etc., or a collection thereof) can be provided (e.g., in communication with the processing arrangement 3802). The computer-accessible medium 3806 can contain executable instructions 3808 thereon. In addition or alternatively, a storage arrangement 3810 can be provided separately from the computer-accessible medium 3806, which can provide the instructions to the processing arrangement 3802 so as to configure the processing arrangement to execute certain exemplary procedures, processes and methods, as described herein above, for example.

Further, the exemplary processing arrangement 3802 can be provided with or include an input/output arrangement 3814, which can include, for example a wired network, a wireless network, the internet, an intranet, a data collection probe, a sensor, etc. As shown in FIG. 38, the exemplary processing arrangement 3802 can be in communication with an exemplary display arrangement 3812, which, according to certain exemplary embodiments of the present disclosure, can be a touch-screen configured for inputting information to the processing arrangement in addition to outputting information from the processing arrangement, for example. Further, the exemplary display 3812 and/or a storage arrangement 3810 can be used to display and/or store data in a user-accessible format and/or user-readable format.

Exemplary Imaging Intracellular Fluorophores With Sub-Micromolar Sensitivity Using Pre-Resonance Stimulated Raman Scattering The exemplary system, method and computer-accessible medium, according to an exemplary embodiment of the present disclosure, can utilize pr-SRS microscopy and apply such exemplary procedure to image molecules in the pre-resonance Raman regime to achieve both superb sensitivity at sub-micromolar concentration, and chemical specificity for multiplex imaging (see, e.g., FIG. 39a). SRS microscopy can be a nonlinear two-laser pump-probe Raman technique, utilizing the stimulated emission quantum amplification from the Stokes beam photons in addition to pump beam photons to facilitate the intrinsically weak Raman transition. (See, e.g., References 99 and 100). The effective stimulated Raman cross section ($\sigma_{st}$) can be defined compared to a spontaneous Raman cross section ($\sigma_{sp}$) as, for example:

$$\sigma_{st} = \sigma_{sp} G(p_{w_s}) \quad (1a)$$

where G ($p_{w_s}$) can be the stimulated Raman gain factor depending on the Stokes beam power ($p_{w_s}$). The measured G ($p_{w_s}$) can be about 107-108 with a biologically compatible Stoke beam power. (See, e.g., Reference 100). With such powerful quantum amplification, SRS microscopy has been applied in a great deal of biological studies such as video-rate imaging in vivo, brain tumors detection and drug delivery tracking. (See, e.g., References 101-103). In addition, as a nonlinear microscopy that can utilize near-infrared excitation wavelength, SRS also offers both subcellular resolution and intrinsic 3D sectioning for deep tissue imaging.

However, current SRS sensitivity can still be far from that of fluorescence microscopy. The measured SRS detection limit of a typical chemical bond such as carbon-hydrogen bond (C—H, $\sigma_{sp} \sim 10^{30}$ cm$^2$) can be about 15 mM. (See, e.g., Reference 99). Even for chemical bonds with exceptional strong Raman polarizability, such as alkynes (C≡C), the reported detection limit can be about 200 µM. (See, e.g., Reference 103). Efforts have been devoted to synthesize molecules with stronger Raman vibration, however, only a few molecules present such property, and the improvements can typically only be about 27 times. (See, e.g., Reference 104). Presently, all the SRS applications focus on probing molecules in the non-resonance region where the absorption peak energy (ω0) of the molecules can be much larger than the pump laser energy (ωpump). (See, e.g., FIG. 39b). One way to further improve SRS sensitivity can be by moving from non-resonance Raman to resonance Raman, where ω0−ωpump <Γ (e.g., Γ can be the homogeneous line width for a molecule, typically, Γ~800 cm-1), thus achieving Raman intensity gain benefiting from the coupling of electronic transition. In this exemplary case, the resonance enhanced spontaneous Raman cross-section $\sigma_{sp,RE}$ could be shown as, for example:

$$\sigma_{sp,RE} = \sigma_{sp} G_{RE} \quad (2a)$$

where, $G_{RE}$ can be the resonance enhanced Raman gain factor, which can increase when the energy difference between ω0 and ωpump can decrease. Furthermore, the effective resonance enhanced SRS cross-section can be expressed as, for example:

$$\sigma_{st,RE} = \sigma_{sp} G_{RE} G(p_{w_s}) \quad (3a)$$

To illustrate the resonance Raman enhancement in the nonlinear SRS microscopy, for example, a non-resonance SRS spectrum of Coumarin 153 can be measured, which can show an absorption peak wavelength (λmax) at about 422 nm (e.g., 23697 cm-1, ω0>>ωpump) (see, e.g., FIG. 39*b*) and a rigorous resonance SRS spectrum of IR895 with λmax=895 nm (e.g., about 11173 cm-1, ω0−ωpump=0) (see, e.g., FIG. 39*c*) by sweeping the pump laser wavelength across the range of about 895-940 nm (e.g., 11173-10638 cm-1) with a fixed Stokes laser wavelength at about 1064.2 nm (e.g., 9398 cm-1). The measured Raman cross-section for the conjugated carbon-carbon double bond (C=C) for IR895 (see, e.g., FIG. 39*c*, element 3905) can approach about 104 as compared to that of Coumarin 153, while C=C of Coumarin 153 may only be about 1.5 times of C=C (e.g., FIG. 39*b*, element 3910). However, with the increasing of the Raman intensity, a large background can appear possibly due to the competing pump-probe process of simultaneous excitation saturation, and stimulated emission of the electronic transition for IR895. Moreover, the measured Raman peak for IR895 can present an inverse Lorentzian shape due to the rigorous resonance Raman measurement for the stimulated Raman loss signal. (See, e.g., Reference 105). For a spectroscopy measurement, these complications may not be an issue with post-acquisition processing. For example, femtosecond SRS spectra of rigorous resonant fluorophores have been heavily documented and the appearance of such an intense background is also well known. (See, e.g., References 106 and 107). Nevertheless, such a background can be extremely undesirable for imaging applications, which can benefit from direct visualization of spatial information.

Close inspection for both the non-resonance SRS spectrum of Coumarin 153 (see, e.g., FIG. 39*b*) and rigorous resonance SRS spectrum of IR895 (see, e.g., FIG. 39*c*) can indicate that a rigorous resonance can bring background more than vibrational signals. Therefore, an exemplary detuning from rigorous resonance can reduce the electronically related background faster than the vibrational signal. For example, this can be rationalized since the electronically related background can benefit from the excitation of the real population, which can vanish if the pump laser energy does not match with the excitation energy, while the vibrational signal can be mediated by virtual state. Indeed, this rationalization can be supported by the SRS spectrum of Cy7.5, which can show a ratio of approximately 0.3 between on-resonance Raman signal and off-resonance Raman signal with a detuning of ω0−ωpump ~2Γ (see, e.g., FIG. 39*c*) compared to that of 0.03 for IR895 when ω0−ωpump~0. (See, e.g., FIG. 39*b*). A further detuning to ~3Γ pinpointed an ATTO740 dye (λmax=740 nm) with both a Raman intensity gain of 1000 times compared to C≡C and a clean off-resonance background (see, e.g., FIG. 39*d*) can be performed. This can be the so-called pre-resonance Raman region, which has been revealed, and can be the most suitable regime for SRS imaging for both high sensitivity and chemical specificity. This can be called the pr-SRS region when ω0−ωpump can fall within the range of 3Γ-5Γ.

An exemplary configuration and principle for pre-resonance SRS microscopy according to an exemplary embodiment of the present disclosure, is shown in FIGS. 39*a*-39*e*. For example, FIG. 39*a* illustrates a diagram of an exemplary SRS system. FIG. 39*b* illustrates an exemplary energy diagram and the corresponding non-resonance SRS spectrum of 4 mM Coumarin 153 in DMSO under power of Ppump=24 mW, Pstokes=24 mW. FIG. 39*c* shows an exemplary energy diagram and the corresponding rigorous resonance SRS spectrum of 10 µM IR895 in methanol under power of Ppump=1.2 mW, Pstokes=9.6 mW. FIG. 39*d* provides an exemplary energy diagram and the corresponding resonance SRS spectrum of 100 µM Cy7.5 in DMSO under power of Ppump=12 mW, Pstokes=9.6 mW. FIG. 39*e* shows an exemplary energy diagram and the corresponding pre-resonance SRS spectrum of 100 µM ATTO740 in DMSO under power of Ppump=24 mW, Pstokes=24 mW. For example, elements 3905, 3910, 3915 and 3920 can indicate the highest Raman peaks in the molecules that attribute to the C=C bond vibration.

Figure 40A:
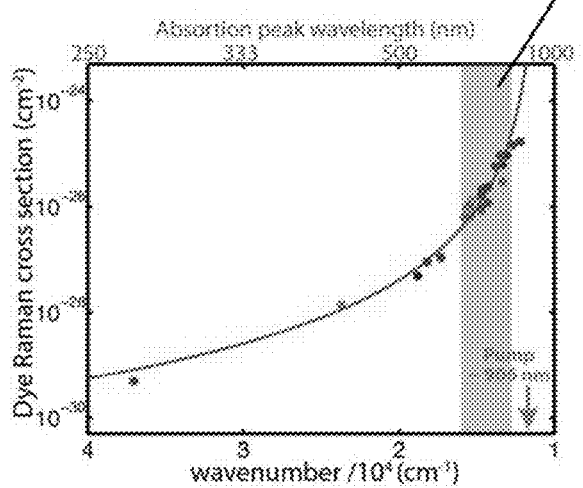
FIGS. 40a-40d are exemplary graphs of signal sensitivities according to an exemplary embodiment of the present disclosure.

To illustrate further the pr-SRS enhancement between the experiment results and theory, FIG. 40*a* shows measured $\sigma_{sp}$ (C=C) for 25 different fluorophores over a wide range of ω0. Assuming the molecular structure variation can be negligible in the consideration for pre-resonance Raman enhancement factor, the graph of FIG. 40*a* was over-plotted with the theoretically approximated pr-Raman cross-section 30 over the same ω0 range of, for example:

$$\sigma_{RE} = K\omega_0(\omega_0 - \omega_{vib})^3 \left( \frac{(\omega_{pump}^2 + \omega_0^2)}{(\omega_0^2 - \omega_{pump}^2)^2} \right)^2 \tag{4a}$$

where ωvib can be the vibrational transition energy. Based on the above, it was determined that the pre-resonance enhancement from theoretical calculations can match very well with the experimental results. The grey shaded area 4005 from FIG. 40*a* indicates the selected fluorophores most suitable for pr-SRS imaging with both high enough pre-resonant enhancement and chemical specificity. For the dyes in the shaded area 4005 from FIG. 40*a*, ATTO740 can be the best dye presenting a pre-resonance enhancement gain ($G_{pRE}$) of 105 when compared with $\sigma_{sp}$(C—H), thus $\sigma_{st,pRE}$ (ATTO740) can reach 10-18 cm$^{-2}$ with an experimental demonstrated G($p_{w_s}$)~108, approaching that of single molecule absorption cross-section at 10-16 cm$^{-2}$.

With such sensitivity, both high sensitivity and chemical specificity for the exemplary pr-SRS technique in solutions can be analyzed. By appropriately selecting the imaging condition with excitation power that can be low enough not to damage the fluorophore but high enough to mildly saturate the Raman transition of ATTO740, the measured detection limit with shot-noise limited sensitivity for ATTO740 can be about 0.7 µM with about a 1 ms time constant and about a 2 µM with about a 100 µs time constant that can be suitable for live-cell imaging (see, e.g., FIG. 40*b*). For pr-SRS, which can still probe the virtual-state mediated Raman transition benefiting from pre-resonance enhancement, the pump laser may not directly excite the fluorophore to the real electronic state. Therefore the photobleaching damage can be minimum. To demonstrate the high chemical specificity in pr-SRS, 3 dyes (Cy5, sulfo-Cy5, ATTO655) that absorb similarly around 650 nm can be selected. While the three dyes (e.g., Cy5 (e.g., element 4025), Sulfo-Cy5 (e.g., element 4030) and ATTO 655 (e.g., element 4035)) present almost indistinguishable absorption and emission spectra (see, e.g., FIG. 40*c*), ATTO655, as an oxazine dye, shows a C=C Raman peak at 1664 cm$^{-1}$ (see, e.g., FIG. 40*d* element 4010) that can be completely distinguishable from the C=C peak of cyanine dyes (Cy5, sulfo-Cy5) at 1606 cm$^{-1}$ (e.g., FIG. 40*d*, element 4010). In addition, sulfo-Cy5 can also be distinguishable from Cy5 between the 1372 cm$^{-1}$ peak and the 1359 cm$^{-1}$ peak (see, e.g., FIG. 40*d*, elements 4015 and 4020) even with a minor chemical modification of aromatic sulfonation. Thus, it can be shown spectroscopically that fluorophores with inseparable electronic spectroscopy can be easily differentiated in Raman spectrum because of the chemical selectivity from vibrational spectroscopy.

Figure 40B:
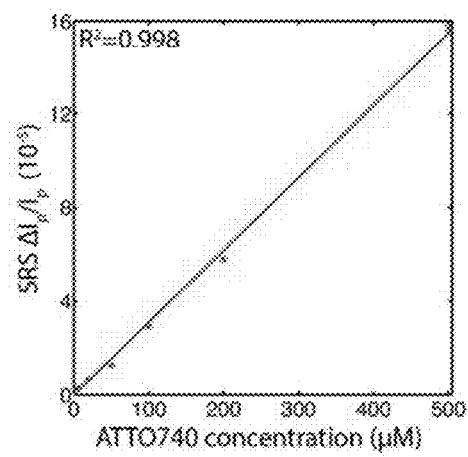
Figure 40C:
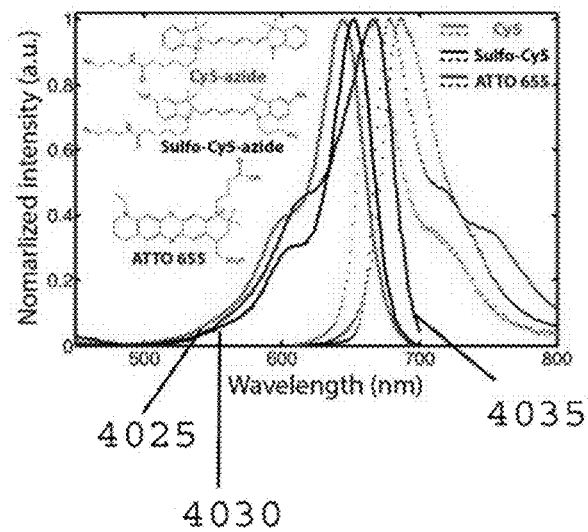
Figure 40D:
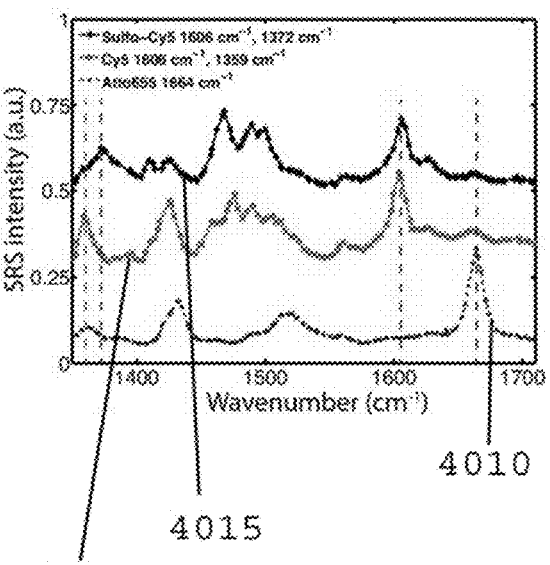

FIGS. 40a-40d show exemplary graphs of an exemplary pr-SRS signal with superb sensitivity and chemical specificity. For example, FIG. 40a illustrates a semi-log plot of the measured Raman cross-section for 25 fluorophores with various absorption peak energies. Grey shaded-area 4005 of FIG. 40a indicates the selected pre-resonance SRS region. FIG. 40b illustrates the linear dependence of stimulated Rarman loss signals at 1642 cm$^{-1}$ with ATTO740 concentrations under an about 100-μs time constant. FIG. 40c illustrates the overlapping absorption and emission spectra of Cy5, sulfo-Cy5 and ATTO655. FIG. 40d illustrates the SRS spectra of Cy5, sulfo-Cy5 and ATTO655 with discernible Raman peaks.

Pr-SRS imaging on intracellular fluorophores can be provided which have achieved exceptional image contrast with a panel of immuno-labeled specific types of intracellular proteins including tubulin, Tom20 (e.g., mitochondria marker), giantin (e.g., Golgi marker) and neurofilament heavy proteins (e.g., Neuronal Marker) with ATTO740 and Dylight 650 dyes in either cultured hippocampal neurons or HeLa cells. (See, e.g., FIGS. 41a-41e). Such high quality SRS images can be obtained for an individual type of proteins labeled with fluorophores. Besides the heightened imaging sensitivity, the specific chemical selectivity using the exemplary system, method, and computer-accessible medium according to an exemplary embodiment of the present disclosure can also be attained, where the on-resonant image at 1642 cm$^{-1}$ (λpump=905.9 nm) for ATTO740-labeled tubulin can be clearly shown, but the corresponding off-resonance signal at 1702 cm-1 (λpump=901 nm) can vanish when the energy difference between the pump and Stokes photons does not match the ovib for the C═C vibrational transition of ATTO740. Such important chemical specificity can extend beyond an achievement for standard fluorescence-based detection systems as illustrated in FIGS. 41g-41j, in which the Alexa647 labeled 5-Ethynyl-2'-deoxyuridine ("EdU") for DNA detection shows a clear Raman vibrational on-off resonance contrast by tuning λpump just to about 2 nm away from the peak. (See, e.g., FIGS. 41g and 41h). Further, the two-photon fluorescence signal remains the same by tuning the excitation laser wavelength by about 2 nm off the peak. (See, e.g., FIGS. 41i and 3j).

Indeed, FIGS. 41a-41j show exemplary pr-SRS images with superb sensitivity and chemical specificity. For example, FIG. 41a illustrates an ATTO740 immuno-labeled tubulin in hippocampal neurons targeting the 1642 cm-1 peak. FIG. 41b illustrates an ATTO740 immuno-labeled tom20 in HeLa cells at 1642 cm-1. FIG. 41c illustrates an ATTO740 immuno-labeled gaintin in HeLa cells at 1642 cm-1. FIG. 41d illustrates a Dylight650 immuno-labeled neurofilament heavy protein in hippocampal neurons at 1606 cm-1. FIG. 41e illustrates an on-resonance ATTO740 immuno-labeled tubulin in HeLa cells at 1642 cm-1. FIG. 41f illustrates an off-resonance signal at 1702 cm-1 on the same HeLa cells as in FIG. 41e. FIG. 41g illustrates an on-resonance Alexa647 labeled 5-Ethynyl-2'-deoxyuridine for newly synthesized DNA in HeLa cells at 1606 cm-1. FIG. 41h illustrates an off-resonance image at 1580 cm-1 on the same HeLa cells as in FIG. 41g. FIGS. 41i and 41j illustrate two-photon fluorescence images of the same HeLa cells as in FIG. 41g at about 810 nm (see e.g., FIG. 41i) and about 812 nm (see e.g., FIG. 41j) of the two-photon excitation peak of Alexa647.

Figures 42A, 42B, 42C, 42D:
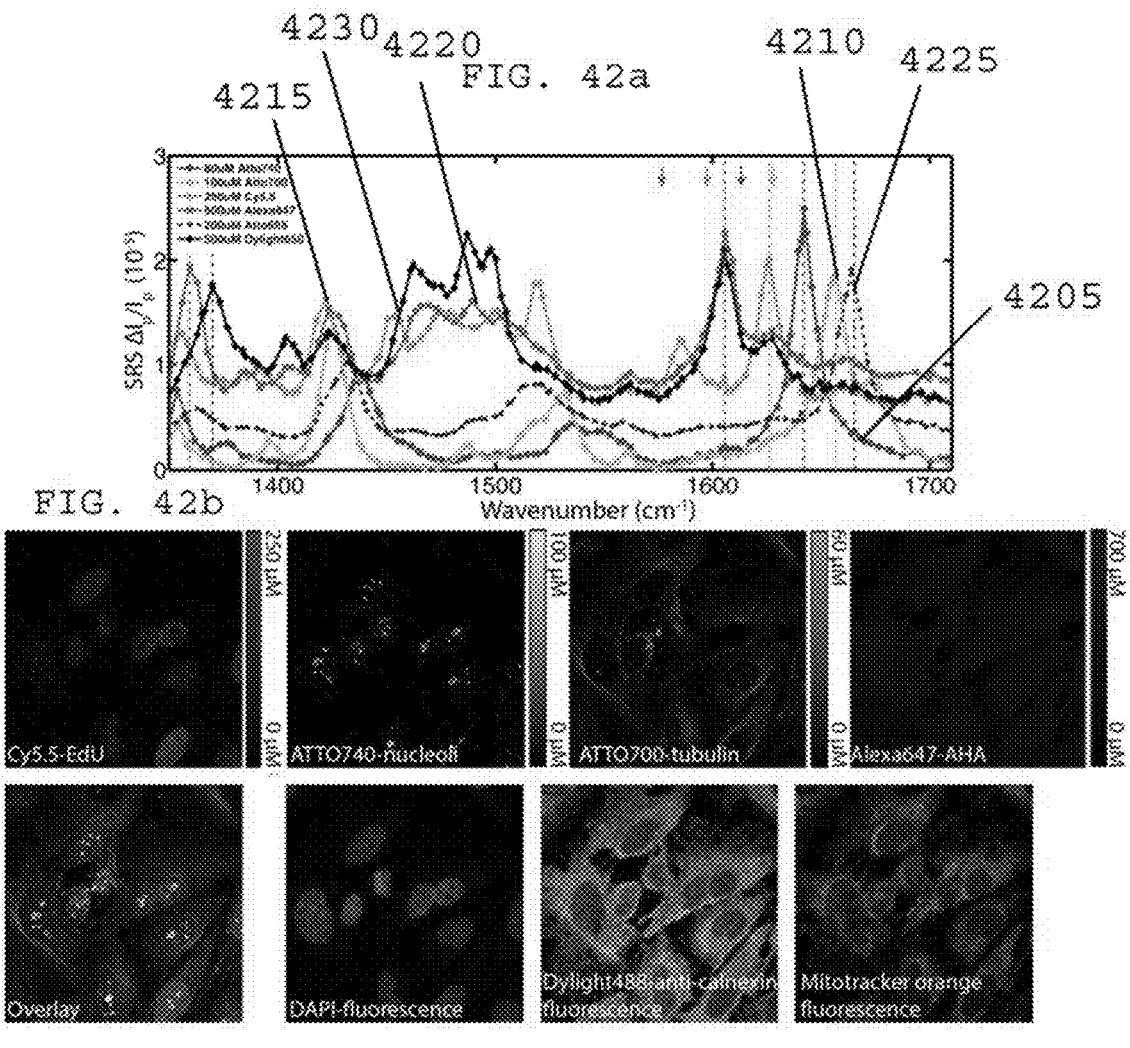
FIG. 42a is a chart of pr-SRS spectra according to an exemplary embodiment of the present disclosure.
FIGS. 42b-42d are images taken using the exemplary pr-SRS system according to an exemplary embodiment of the present disclosure.

Thus, from both the spectroscopy and imaging perspectives, the superb sensitivity and the distinct chemical specificity for the exemplary pr-SRS of fluorophores is shown. With such sensitivity and specificity, the uses of the exemplary system, method and computer-accessible medium for biomedical researches, among which large number multi-color imaging can be important. For example, FIG. 42a illustrates an exemplary graph of a 6-color channel pr-SRS multiplex imaging possibility with 6 different fluorophores which include 80 μm Atto740 (e.g., element 4205), 100 μm Atto 700 (e.g., element 4210), 250 μm Cy5.5 (e.g., element 4215), 500 μm Alexa647 (e.g., element 4220), 200 μm Atto665 (e.g., element 4225) and 500 μm Dylight650 (e.g., element 4230). Among the different fluorophores shown, each of the three dyes shows an almost overlapping absorption and emission spectra. By specifically selecting the target, FIG. 42b demonstrates the 4-color pr-SRS imaging for intracellular fluorophores with distinct and quantitative signal separation of Cy5.5 (λmax=673 nm) labeled newly synthesized DNA, ATTO740 (λmax=740 nm) labeled nucleoli fibrillarin proteins, Atto700 (λmax=700 nm) labeled α-tubulin and Alexa647 labeled newly synthesized proteins after linear combinational procedure. The 4-color overlay image (see, e.g., FIG. 42c) presents clearly defined spatial relationships between the targeted four types of molecules. Moreover, since SRS signal can be orthogonal with fluorescence signal, besides the multiplex pr-SRS imaging alone, tandem imaging with the fluorescence could further expand the numbers of simultaneously detected colors. To demonstrate such configuration, a DAPI (λmax=350 nm) that stains DNA, dylight488 (λmax=488 nm) staining calnexin (e.g., ER marker) and mito-tracker orange (e.g., 543 nm) staining mitochondria for three-color fluorescence imaging, in addition to the above 4-color multiplex pr-SRS imaging in the same set of cells, can be selected (see, e.g., exemplary images of FIG. 42d). Since, for example, the 4 dyes for pr-SRS imaging can all be with an absorption peak at about 650-740 nm with far-red emission, and the 3 dyes for fluorescence imaging can be around 350-543 nm that can be in the non-resonance SRS region with minimum resonance enhancement, both the fluorescence signal and the pr-SRS signal can be free of interference from each other. Thus, the exemplary system, method and computer-accessible medium can achieve at least 7-color imaging.

In particular, FIGS. 42a-42d illustrate simultaneous 7-color quantitative pr-SRS and fluorescence tandem imaging. For example, FIG. 42a illustrates pr-SRS spectra with 6 possible colors for 6 fluorophores of ATTO740 (1642 cm-1), ATTO700 (1657 cm-1), Cy5.5 (1626 cm-1), alexa647 (1606 cm-1, 1358 cm-1), ATTO655 (1665 cm-1) and Dylight650 (1606 cm-1, 1358 cm-1). FIG. 42b illustrates a 4-color quantitative pr-SRS imaging of Cy5.5 labeled EdU for newly synthesized DNA; ATTO740 immuno-labeled Fibrillarin protein of nucleolar marker; ATTO740 immuno-labeled alpha-tubulin; Alexa657 labeled AHA for newly synthesized proteins in the same HeLa cells. FIG. 42c illustrates an overlay of 4-color pr-SRS images in FIG. 42b. FIG. 42d illustrates tandem fluorescence imaging of DAPI labeled DNA; Dylight488 immuno-labeled Calnexin protein of Endoplasmic reticulum marker; Mitotracker orange labeled mitochondria.

Additional exemplary labels can be created for pr-SRS palette using various other vibrational moieties. Unlike C═C, which can exhibit multiple peaks in the crowded fingerprint region, triple bonds, including alkyne or nitrile, can display a single sharp Raman peak in the wide silent window (e.g., from about 1800 to about 2800 cm-1) free from cellular background. Thus pr-SRS imaging of triple bonds can greatly expand a vibrational palette with minimum cross talks. This can be non-trivial because triple bonds may need to be coupled with an electronic transition in order to gain resonance enhancement. Thus, described herein is a new family of vibrational dyes in which triple bonds can directly participate in the π-conjugation systems. For example, general dye scaffolds with optimal conjugation position of triple bonds were determined, and then their absorption peaks were tuned into the pr-SRS region, ensuring both intensity and chemical specificity. To generate more vibrational colors, an isotopic edition on the triple bonds was utilized in conjunction with exquisite electron-density tuning on the 71-conjugation system to shift the peak frequency. The resulting 10 exemplary reporters, termed Manhattan Raman scattering ("MARS") dyes (see e.g., FIGS. 43*a*-43*d*: e.g., MARS2242 element 4305, MARS2228 element 4310, MARS2215 element 4315, MARS2200 element 4320, MARS2186 element 4325, MARS2176 element 4330, MARS2159 element 4335, MARS2148 element 4340, MARS2114 element 4345 and MARS2061 element 4350), display well-resolved individual pr-SRS peaks in a cell-silent window. Except for MARS2124 whose pr-SRS spectrum can exhibit some background likely from two-photon absorption, the other 9 exemplary MARS dyes have negligible (e.g., about <15% on average) spectral cross-talk under the narrow-band (e.g., about 6 cm-1) laser excitation.

Additionally, the exemplary system, method and computer-accessible medium, according to an exemplary embodiment of the present disclosure, can utilize pr-SRS that can achieve an increased detection sensitivity down to sub-micromole and high chemical specificity for multicolor imaging. For example, a narrow region of the absorption peaks of dyes can be selected that can be suitable for pr-SRS imaging, which can benefit from pre-resonance Raman enhancement, but does not suffer from any other competing pump-probe signal contributing to a large off-resonance background. With such sensitivity and specificity, 4-color imaging can be achieved by commercially available dyes with pr-SRS alone, which can already be comparable to the typical number limit in multi-color fluorescence imaging. In tandem with fluorescence microscopy, simultaneous imaging of 3 more colors can be obtained, thus, almost doubling the number limit of multicolor fluorescence imaging. This number can be expanded furthermore with custom synthesized molecules leading to more resolvable pr-SRS colors.

Exemplary SI Methods and Materials

An integrated laser (e.g., picoEMERALD with custom modification, Applied Physics & Electronics, Inc.) can be used as the light source for both pump and Stokes beams. picoEMERALD can provide an output pulse train at 1064 nm with 6 ps pulse width and 80 MHz repetition rate, which serves as the Stokes beam. The frequency-doubled beam at 532 nm can be used to synchronously seed a picosecond optical parametric oscillator ("OPO") to produce a mode-locked pulse train (e.g., the idler beam of the OPO can be blocked with an interferometric filter) with 5~6 ps pulse width. The wavelength of the OPO can be tunable from about 720 to about 990 nm, which can serve as the pump beam. The intensity of the about 1064 nm Stokes beam can be modulated sinusoidally by a built-in electro-optic modulator ("EOM") at about 8 MHz with a modulation depth of more than about 95%. The pump beam can be spatially overlapped with the Stokes beam with a dichroic mirror inside picoEMERALD. The temporal overlap between pump and Stokes pulse trains can be ensured with a built-in delay stage and optimized by the SRS signal of pure dodecane liquid.

Pump and Stokes beams can be coupled into an inverted laser-scanning microscope (e.g., FV1200MPE, Olympus) optimized for near IR throughput. An about 60× water objective (UPlanAPO/IR, 1.2 N.A., Olympus) with high near IR transmission can be used for all cellular level imaging, and a 25× water objective (XLPlan N, 1.05 N.A., MP, Olympus) with both high near IR transmission and a large field of view can be used for brain tissue and in vivo imaging. The Pump/Stokes beam size can be matched to fill the back-aperture of the objective. The forward going Pump and Stokes beams, after passing through the sample, can be collected in transmission with a high N.A. condenser lens (e.g., oil immersion, 1.4 N.A., Olympus), which can be aligned following Kohler illumination. A telescope can then be used to image the scanning mirrors onto a large area (e.g., about 10 mm by about 10 mm) Si photodiode (e.g., FDS1010, Thorlabs) to descan beam motion during laser scanning. The photodiode can be reverse-biased by about 64 V from a DC power supply to increase both the saturation threshold and response bandwidth.

A high optical density ("O.D.") bandpass filter (e.g., 890/220 CARS, Chroma Technology) can be used to block the Stokes beam completely, and transmit the Pump beam only. The output current of the photodiode can be electronically pre-filtered by an about 8-MHz band-pass filter (e.g., KR 2724, KR electronics) to suppress both the 80 MHz laser pulsing and the low-frequency contribution due to laser scanning across the scattering sample. It can then be fed into a radio frequency lock-in amplifier (e.g., SR844, Stanford Research Systems) terminated with about 50Ω to demodulate the stimulated Raman loss signal experienced by the pump beam. The in-phase X-output of the lock-in amplifier can be fed back into the analog interface box (e.g., FV10-ANALOG) of the microscope. For all imaging, about 256 by 256 pixels can be acquired for one frame with an about 200 μs of pixel dwell time (e.g., 13 s per frame) for laser scanning and about 100 μs of time constant (e.g., 6 db filter) from the lock-in amplifier. For FIGS. 41*a*-41*f* and 4-color pr-SRS imaging at channels 1606 cm-1 and 1626 cm-1, laser powers can be Ppump=24 mW, Pstokes=48 mW. For FIGS. 41*g* and 41*h*, laser powers can be Ppump=24 mW, Pstokes=12 mW. For FIGS. 41*i* and 41*j*, laser power can be 24 mW for two-photon imaging. For 4-color pr-SRS imaging at channels 1642 cm-1, 1657 cm-1 and 2940 cm-1 (e.g., cellular background) laser powers can be Ppump=24 mW, Pstokes=48 mW.

Exemplary SRS Spectra

Stimulated Raman scattering spectra for all fluorophores can be acquired by fixing the stokes beam laser at about 1064.2 nm, and scanning the pump laser through a designated wavelength range point by point.

Exemplary Materials

Fluorophores can include, for example: 5-Ethynyl-2′-deoxyuridine (T511285, Aldrich); L-Azidohomoalanine ("AHA") (C10102, Invitrogen), Click-iT® Cell Reaction Buffer Kit (C10269, Invitrogen).

Fluorophores for SRS in FIG. 40*a* include: Benzotriazole (B11400, Sigma, λmax~270 nm); Coumarin 153 (546186, Sigma, λmax~422 nm); Rhodamine 6G (83697 Sigma, λmax~528 nm); Rhodamine B (83689 Sigma, λmax~553 nm); Sulforhodamine 101 (S7635 Sigma, λmax~580 nm); Alexa Fluor® 633 NHS Ester (A-20105, Invitrogen, λmax~633 nm); CF640R-azide (92085, Biotium, λmax~640 nm); Cy5-azide (A3030, Lumiprobe, λmax~645 nm); sulfo-cy5-azide (777323 Sigma, λmax~646 nm); Alexa647-azide (A10277, Invitrogen, λmax~650 nm); Dylight 650 NHS Ester (62265, Thermo Scientific, λmax~650 nm); Atto 655 azide (11774 Sigma, λmax~660 nm); Cy5.5-azide (178, AAT-bioquest, λmax~678 nm); ATTO680 (94875 Sigma, λmax~680 nm); Rhodamine 800 (83701 Sigma, λmax~680 nm); Alexa 680 NHS Ester (A-20008, Invitrogen, λmax~680 nm); Alexa700 NHS Ester (A-20010, Invitrogen, λmax~700 nm); ATTO700 (30674 Sigma, λmax~700 nm); ATTO725 (47156 Sigma, λmax~725 nm); ATTO740 (91394 Sigma, λmax~740 nm); Alexa750 NHS Ester (A-20011, Invitrogen); Cy7-azide (A5030, Lumiprobe, λmax~749 nm); 3,3'-Diethylthiatricarbocyanine iodide (381306 Sigma, λmax~765 nm); Cy7.5-azide (A6030, Lumiprobe, λmax~788 nm); IR820 (543365 Sigma, λmax~820 nm).

Other Fluorophores can include: IR895 (392375 Sigma, λmax~895 nm); MitoTracker® Orange CMTMRos (M-7510, Invitrogen); NucBlue® Fixed Cell ReadyProbes® Reagent ("DAPI") (R37606, Invitrogen).

Primary antibodies can include: Anti-Fibrillarin antibody—Nucleolar Marker (ab5821, Abcam); Anti-200 kD Neurofilament Heavy antibody (ab4680, Abcam); Anti-α-Tubulin antibody (T9026, Sigma); Anti-Giantin antibody (ab24586, Abcam); Anti-Tom20 Antibody (sc-11415, Santa Cruz Biotechnology); Anti-Calnexin antibody—ER Membrane Marker (ab140818, Abcam).

Secondary antibodies conjugated with fluorophores can include, e.g.: Goat-anti-Rabbit IgG-Atto 740 antibody (49559, Sigma); Goat-anti-Mouse IgG-Atto 700 antibody (2110, Hypermol); Goat anti-Chicken IgY DyLight 488 antibody (SA5-10070, Thermo Scientific).

Exemplary Sample Preparation for Intracellular Cell Imaging

For immuno-staining cells can be fixed in methanol for about 28 min or first in about 4% PFA for about 8 min and then replaced with methanol for about 20 min more. Cells can then be washed with about 10% goat serum/1% BSA/0.3M glycine solution twice before permealization in about 0.010% triton PBS for about 45 min. Primary antibody can then be added with about 1:200 dilution in about 3% BSA in 4 C overnight. After blocking with about 10% goat serum for about 30 min, secondary antibody conjugated with fluorophores can be added with about 1:100 dilution in about 10% goat serum in 4 C overnight.

For 7-color pr-SRS and fluorescence tandem imaging, HeLa cells can be seeded on a coverslip in a petri-dish with about 2 mL of DMEM for about 20 h, and then replaced with Methionine-deficient medium for about 30 min. Then about 1 mM AHA and about 100 µM EdU can be added in to medium for about 18 hr. An about 400 nM MitoTracker® Orange can be added into medium for about 30 min before fixation of the cell with about 4% PFA for about 8 min and then replaced with methanol for about 20 min more. Immuno-staining follows the procedure above. After immuno-staining, about 4 µM Cy5.5-azide can be added to the cells with click-it Cell Reaction Buffer for the reaction with EdU following the manual from Invitrogen. After washing with PBS, about 4 µM alexa647-alkyne can be added to the cells with click-it Cell Reaction Buffer for the reaction with AHA. At last, DAPI can be added to cells for 20 min following the instruction from manual.

DMEM was made of about 90% DMEM medium (e.g., 11965, invitrogen), about 10% FBS (e.g., 10082, invitrogen) and about 1× penicillin/streptomycin (e.g., 15140, invitrogen); Methionine-deficient medium was made by supplying about 4 mM L-glutamine, about 0.2 mM L-cystine, about 10% FBS and about 1% penicillin/streptomycin to the DMEM medium without L-methionine, L-cysteine and L-glutamine.

Exemplary Linear Combination Procedure

Because the exemplary SRS signal can be linearly dependent on the analyte concentration, the 4-channel pr-SRS signal for the concentrations of the ATTO740 labeled nucleoli Fibrillarin protein, ATTO700 labeled α-tubulin, Cy5.5 labeled EdU and Alexa647 labeled AHA can subtract the cellular background contribution calibrated from 2940 cm-1 channel and can be expressed in the following the exemplary matrix:

$$\begin{bmatrix} \text{cross-section} \\ \text{matrix} \end{bmatrix} \begin{bmatrix} C_{nucleoli} \\ C_{tubulin} \\ C_{EdU} \\ C_{AHA} \end{bmatrix} = \begin{bmatrix} S_{1657} - (S_{2940}/1.63) \\ S_{1626} - (S_{2940}/2.45) \\ S_{1642} - (S_{2940}/5.56) \\ S_{1606} - (S_{2940}/11.46) \end{bmatrix}, \text{ and}$$

$$\begin{bmatrix} \text{cross-section} \\ \text{matrix} \end{bmatrix} = \begin{bmatrix} \sigma_{ATTO740,1657} & \sigma_{ATTO700,1657} & \sigma_{Cy5.5,1657} & \sigma_{alexa\ 647,1657} \\ \sigma_{ATTO740,1642} & \sigma_{ATTO700,1642} & \sigma_{Cy5.5,1642} & \sigma_{alexa\ 647,1642} \\ \sigma_{ATTO740,1626} & \sigma_{ATTO700,1626} & \sigma_{Cy5.5,1626} & \sigma_{alexa\ 647,1626} \\ \sigma_{ATTO740,1606} & \sigma_{ATTO700,1606} & \sigma_{Cy5.5,1696} & \sigma_{alexa\ 647,1606} \end{bmatrix}$$

$$\begin{bmatrix} C_{nucleoli} \\ C_{tubulin} \\ C_{EdU} \\ C_{AHA} \end{bmatrix} = \begin{bmatrix} \text{cross-section} \\ \text{matrix} \end{bmatrix}^{-1} \begin{bmatrix} S_{1657} - (S_{2940}/1.63) \\ S_{1626} - (S_{2940}/2.45) \\ S_{1642} - (S_{2940}/5.56) \\ S_{1606} - (S_{2940}/11.46) \end{bmatrix}$$

Each fluorophore cross section number can be measured using about a 500 µM solution in each channel by SRS under the same power and acquisition time as in final the cellular imaging condition. Therefore, the solved molecule concentrations can be in the unit(s) of M.

Figure 44:
FIG. 44 is a set of further images taken using the exemplary pr-SRS system according to an exemplary embodiment of the present disclosure.

FIG. 44 illustrates exemplary raw images for 4-color pr-SRS microscopy at channels of 1606 cm-1, 1626 cm-1, 1642 cm-1, 1657 cm-1 and 2940 cm-1 before linear combination algorithm retrieval.

The foregoing merely illustrates the principles of the disclosure. Various modifications and alterations to the described exemplary embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.
1. Chalfie M, Tu Y, Euskirchen G, Ward W W P D (1994) Green fluorescent protein as a marker gene expression. Science 263:802-804.
2. Tsien R Y (1998) The Green Fluorescent. Annu. Rev. Biochemistry 67:509-544.
3. Resch-Genger U, Grabolle M, Cavaliere-Jaricot S, Nitschke R N T (2008) Quantum dots versus organic dyes as fluorescent labels. Nature methods 5:763-775.
4. Miyawaki A, Sawano A, Kogure T (2003) Lighting up cells: labelling proteins with fluorophores. Nature cell biology.
5. Knoll B, Keilmann F (1999) Near-field probing of vibrational absorption for chemical microscopy. Nature 399: 7-10.
6. Turrell G, Corset J (1996) raman microscopy developments and application 7. Evans C L, Xie X S (2008) Coherent anti-stokes Raman scattering microscopy: chemical imaging for biology and medicine. Annual review of analytical chemistry (Palo Alto, Calif.) 1:883-909.
8. Freudiger C, Min W, Saar B, Lu S, Holtom G (2008) Label-free biomedical imaging with high sensitivity by stimulated Raman scattering microscopy. Science 322: 1857-1861.
9. Min W, Freudiger C W, Lu S, Xie X S (2011) Coherent nonlinear optical imaging: beyond fluorescence microscopy. Annual review of physical chemistry 62:507-30.
10. Prescher J a, Bertozzi C R (2005) Chemistry in living systems. Nature chemical biology 1:13-21.
11. Sletten E M, Bertozzi C R (2009) Bioorthogonal chemistry: fishing for selectivity in a sea of functionality. Angewandte Chemie (International ed. in English) 48:6974-98.
12. Lim R K V, Lin Q (2010) Bioorthogonal chemistry: recent progress and future directions. Chemical communications (Cambridge, England) 46:1589-600.
13. Yamakoshi H et al. (2011) Imaging of EdU, an alkyne-tagged cell proliferation probe, by Raman microscopy. Journal of the American Chemical Society 133:6102-5.
14. Yamakoshi H et al. (2012) Alkyne-tag Raman imaging for visualization of mobile small molecules in live cells. Journal of the American Chemical Society 134:20681-9.
15. Bloembergen N (1967) The Stimulated Raman Effect. American Journal of Physics 35:989-1023.
16. Masters B R, So P T C, Mantulin W W (2008) Handbook of biomedical nonlinear optical microscopy. eds Masters B R, So P T C (Oxford University Press)
17. Saar B G et al. (2010) Video-rate molecular imaging in vivo with stimulated Raman scattering. Science (New York, N.Y.) 330:1368-70.
18. Salic A, Mitchison T J (2008) A chemical method for fast and sensitive detection of DNA synthesis in vivo. Proceedings of the National Academy of Sciences of the United States of America 105:2415-20.
19. Neef A B, Luedtke N W (2011) Dynamic metabolic labeling of DNA in vivo with arabinosyl nucleosides. Proceedings of the National Academy of Sciences of the United States of America 108:20404-9.
20. Jao C Y, Salic A (2008) Exploring RNA transcription and turnover in vivo by using click chemistry. Proceedings of the National Academy of Sciences of the United States of America 105:15779-84.
21. Beatty K E et al. (2006) Fluorescence visualization of newly synthesized proteins in mammalian cells. Angewandte Chemie (International ed. in English) 45:7364-7.
22. Liu J, Xu Y, Stoleru D, Salic A (2012) Imaging protein synthesis in cells and tissues with an alkyne analog of puromycin. Proceedings of the National Academy of Sciences of the United States of America 109:413-8.
23. Jao C Y, Roth M, Welti R, Salic A (2009) Metabolic labeling and direct imaging of choline phospholipids in vivo. Proceedings of the National Academy of Sciences of the United States of America 106:15332-7.
24. Hershey J W B, Sonenberg N, Mathews M B Eds. (2012) Protein synthesis and translational control. Cold Spring Harbor Laboratory Press.
25. Martin K C, Barad M, Kandel E R (2000) Local protein synthesis and its role in synapse-specific plasticity. Curr. Opin. Neurobiol. 10:587-592.
26. Kandel E R (2001) The molecular biology of memory storage: a dialogue between genes and synapses. Science 294:1030-1038.
27. Ho V M, Lee J A, Martin K C (2011) The cell biology of synaptic plasticity. Science 334:623-628.
28. Chalfie M, Tu Y, Euskirchen G, Ward W W, Prasher D C (1994) Green fluorescent protein as a marker for gene expression. Science 263:802-805.
29. Tsien R Y (1998) The green fluorescent protein. Annu. Rev. Biochem. 67:509-544.
30. Dieterich D C, Link A J, Graumann J, Tirrell D A, Schuman E M (2006) Selective identification of newly synthesized proteins in mammalian cells using bioorthogonal noncanonical amino acid tagging (BONCAT). Proc. Natl. Acad. Sci. USA 103:9482-9487.
31. Beatty K E et al. (2006) Fluorescence visualization of newly synthesized proteins inmammalian cells. Angew. Chem. 45:7364-7367.
32. Beatty K E, Tirrell D A (2008) Two-color labeling of temporally defined proteinpopulations in mammalian cells. Bioorg. Med. Chem. Lett. 18:5995-5999.
33. Roche F K, Marsick B M, Letourneau P C (2009) Protein synthesis in distal axons is notrequired for growth cone responses to guidance cues. J Neurosci. 29:638-652.
34. Dieterich D C et al. (2010) In situ visualization and dynamics of newly synthesizedproteins in rat hippocampal neurons. Nat. Neurosci. 13:897-905.
35. Tcherkezian J, Brittis P A, Thomas F, Roux P P, Flanagan J G (2010) Transmembrane receptor DCC associates with protein synthesis machinery and regulates translation. Cell 141:632-644.
36. Hinz F I, Dieterich D C, Tirrell D A, Schuman E M (2012) Non-canonical amino acid labeling in vivo to visualize and affinity purify newly synthesized proteins in larval zebrafish. ACS Chem. Neurosci. 3:40-49.
37. Liu J, Xu Y, Stoleru D, Salic A (2012) Imaging protein synthesis in cells and tissues with an alkyne analog of puromycin. Proc. Natl. Acad. Sci. USA 109:413-418.
38. Boyce M, Bertozzi C R (2011) Bringing chemistry to life. Nat. Methods 8:638-642.
39. Schoenheimer R, Rittenberg D (1936) Deuterium as an indicator in the study of intermediary metabolism. J. Biol. Chem. 111:163-168.
40. Schoenheimer R, Rittenberg D (1938) Application of isotopes to the study of intermediary metabolism. Science 87:221-226.

41. Ong S E et al. (2002) Stable isotope labeling by amino acids in cell culture, SILAC, as a simple and accurate approach to expression proteomics. Mol. Cell. Proteomics 1:376-386.
42. Mann M (2006) Functional and quantitative proteomics using SILAC. Nat. Rev. Mol. Cell. Biol. 7:952-958.
43. Harsha H C, Molina H, Pandey A (2008) Quantitative proteomics using stable isotope labeling with amino acids in cell culture. Nat. Protoc. 3:505-516.
44. Geiger T et al. (2011) Use of stable isotope labeling by amino acids in cell culture as a spike-in standard in quantitative proteomics. Nat. Protoc. 6:147-157.
45. Ingolia N T, Lareau L F, Weissman J S (2011) Ribosome profiling of mouse embryonic stem cells reveals the complexity and dynamics of mammalian proteomes. Cell. 147:789-802.
46. Potma E O, Xie X S (2008) Theory of spontaneous and coherent Raman scattering in Handbook of Biomedical Nonlinear Optical Microscopy; Masters B R, So PTC Eds. Oxford University Press: New York, N.Y., USA.
47. Zumbusch A, Holtom G R, Xie X S (1999) Three-dimensional vibrational imaging by coherent anti-Stokes Raman scattering. Phys. Rev. Lett. 82:4142-4145.
48. Evans C L, Xie X S (2008) Coherent anti-Stokes Raman scattering microscopy: chemical imaging for biology and medicine. Annu. Rev. Anal. Chem. 1:883-909.
49. Cheng J X, Xie X S (2004) Coherent anti-Stokes Raman scattering microscopy: instrumentation, theory, and applications. J. Phys. Chem. B 108:827-840.
50. Pezacki J P et al. (2011) Chemical contrast for imaging living systems: molecular vibrations drive CARS microscopy. Nat. Chem. Biol. 7:137-145.
51. Suhalim J L, Boik J C, Tromberg B J, Potma E O (2012) The need for speed. J. Biophotonics 5:387-95.
52. Ploetz E, Laimgruber S, Berner S, Zinth W, Gilch P (2007) Femtosecond stimulated Raman microscopy. Appl. Phys. B 87:389-393.
53. Freudiger C W et al. (2008) Label-free biomedical imaging with high sensitivity by stimulated Raman scattering microscopy. Science 322:1857-1861.
54. Ozeki Y, Dake F, Kajiyama S, Fukui K, Itoh K (2009) Analysis and experimental assessment of the sensitivity of stimulated Raman scattering microscopy. Opt. express. 17:3651-3658.
55. Nandakumar P, Kovalev A, Volkmer A (2009) Vibrational imaging based on stimulated Raman scattering microscopy. New J. Phys. 11:033026.
56. Saar B G et al. (2010) Video-rate molecular imaging in vivo with stimulated Raman scattering. Science 330: 1368-1370.
57. Zhang D, Slipchenko M N, Cheng J X (2011) Highly sensitive vibrational imaging by femtosecond pulse Stimulated raman Loss. J. Phys. Chem. Lett. 2:1248-1253.
58. Wang M C, Min W, Freudiger C W, Ruvkun G, Xie X S (2011) RNAi screening for fat regulatory genes with SRS microscopy. Nat. methods 8:135-138.
59. Zhang X et al. (2012) Label-free live-cell imaging of nucleic acids using stimulated Raman scattering microscopy. Chemphyschem. 13:1054-1059.
60. Fu D et al. (2012) Quantitative chemical imaging with multiplex stimulated Raman scattering microscopy. J. Am. Chem. Soc. 134: 3623-3626.
61. Ozeki Y et al. (2012) High-speed molecular spectral imaging of tissue with stimulated Raman scattering. Nature Photon. 6:845-851.
62. Einstein A (1917) On the quantum theory of radiation. Phys. Z. 18:121-128.
63. Bloembergen N (1967) The Stimulated Raman Effect. Am. J. Phys. 35:989-1023.
64. Min W, Freudiger C W, Lu S, Xie X S (2011) Coherent nonlinear optical imaging: beyond fluorescence microscopy. Annu Rev Phys Chem. 62:507-530.
65. Min W (2011) Label-free optical imaging of nonfluorescent molecules by stimulated radiation. Curr. Opin. Chem. Biol. 15:831-837.
66. Okayasu T, Ikeda M, Akimoto K, Sorimachi K (1997) The amino acid composition of mammalian and bacterial cells. Amino Acids 13:379-391.
67. Phair R D and Misteli T (2000) High mobility of proteins in the mammalian cell nucleus. Nature 404: 604-609.
68. Andersen J S et al. (2005) Nucleolar proteome dynamics. Nature 433:77-83.
69. Boisvert F M et al. (2012) A quantitative spatial proteomics analysis of proteome turnover in human cells. Mol. Cell. Proteomics. 11(3): M111.011429.
70. Piez K A and Eagle H (1958) The free amino acid pool of cultured human cells. J. Biol. Chem. 231: 533-545
71. Lechene C P, Luyten Y, McMahon G, Distel D L (2007) Quantitative imaging of nitrogen fixation by individual bacteria within animal cells. Science 317:1563-1566.
72. Zhang D S et al. (2012) Multi-isotope imaging mass spectrometry reveals slow protein turnover in hair-cell stereocilia. Nature 481:520-524.
73. van Manen H J, Lenferink A, Otto C (2008) Noninvasive imaging of protein metabolic labeling in single human cells using stable isotopes and Raman microscopy. Anal. chem. 80:9576-9582.
74. Ji Minbiao et al. (2013) Rapid, label-free detection of brain tumors with stimulated Raman scattering miscroscopy. Sci. Transl. Med. 5(201): 201ra119.
76. Saar et al. (2011) Imaging drug delivery to skin with stimulated Raman scattering microscopy. Mol. Pharm. 8(3): 969-75.
77. Cui et al. (2009) Comparing coherent and spontaneous Raman scattering under biological imaging conditions. Opt. Lett. 34(16): 773-775.
78. Petrov et al. (2007) Comparision of coherent and spontaneous Raman microspectroscopies for noninvasive detection of single bacterial endospores. Proc. Natl. Acad. Sci. USA. 104(19): 7776-9.
79. Nie, S., Chiu, D. T. & Zare, R. N. Probing individual molecules with confocal fluorescence microscopy. Science 266, 1018-1021 (1994).
80. Moerner, W. E. & Orrit, M. Illuminating single molecules in condensed matter. Science 283, 1670-1676 (1999).
81. Yuste, R. Fluorescence microscopy today. Nat. Methods 2, 902-904 (2005).
82. Denk, W., Strickler, J. H. & Webb, W. W. Two-photon laser scanning fluorescence microscopy. Science 248, 73-76 (1990).
83. Hell, S. W. & Wichmann, J. Breaking the diffraction resolution limit by stimulated emission: stimulated-emission-depletion fluorescence microscopy. Opt. Lett. 19, 780-2 (1994).
84. Betzig, E. et al. Imaging intracellular fluorescent proteins at nanometer resolution. Science 313, 1642-1645 (2006).
85. Rust, M. J., Bates, M. & Zhuang, X. Sub-diffraction-limit imaging by stochastic optical reconstruction microscopy (STORM). Nat. Methods 3, 793-795 (2006).

86. Ha, T. et al. Probing the interaction between two single molecules: fluorescence resonance energy transfer between a single donor and a single acceptor. Proc. Natl. Acad. Sci. U.S.A 93, 6264-6268 (1996).

87. Myers, A B. Molecular electronic spectral broadening in liquids and glasses. Annu. Rev. Phys. Chem. 49, 267-295 (1998).

88. Nemkovich, N., Rubinov, A. & Tomin, V. Inhomogeneous Broadening of Electronic Spectra of Dye Molecules in Solutions. Top. Fluoresc. Spectrosc. S E—8 2, 367-428 (2002).

89. Gaiduk, A., Yorulmaz, M., Ruijgrok, P. V & Orrit, M. Room-temperature detection of a single molecule's absorption by photothermal contrast. Science 330, 353-356 (2010).

90. Chong, S., Min, W. & Xie, X. S. Ground-state depletion microscopy: Detection sensitivity of single-molecule optical absorption at room temperature. J. Phys. Chem. Lett. 1, 3316-3322 (2010).

91. Kukura, P., Celebrano, M., Renn, A. & Sandoghdar, V. Single-molecule sensitivity in optical absorption at room temperature. J. Phys. Chem. Lett. 1, 3323-3327 (2010).

92. Giesen, C. et al. Highly multiplexed imaging of tumor tissues with subcellular resolution by mass cytometry. Nat. Methods 11, 417-22 (2014).

93. Angelo, M. et al. Multiplexed ion beam imaging of human breast tumors. Nat. Med. 20, 436-42 (2014).

94. Barlogie, B. et al. Flow Cytometry in Clinical Cancer Research Flow Cytometry in Clinical Cancer Researchl. 43, 3982-3997 (1983).

95. Geiger, B., Spatz, J. P. & Bershadsky, A. D. Environmental sensing through focal adhesions. Nat. Rev. Mol. Cell Biol. 10, 21-33 (2009).

96. Cheng, J.-X. & Xie, X. S. Coherent Raman Scattering Microscopy. CRC press (2012).

97. Nie, S. Probing Single Molecules and Single Nanoparticles by Surface-Enhanced Raman Scattering. Science. 275, 1102-1106 (1997).

98. Kneipp, K. et al. Single molecule detection using surface-enhanced Raman scattering (SERS). Phys. Rev. Lett. 78, 1667-1670 (1997).

99. Freudiger, C., Min, W., Saar, B., Lu, S. & Holtom, G. Label-free biomedical imaging with high sensitivity by stimulated Raman scattering microscopy. Science (80-.). 322, 1857-1861 (2008).

100. Min, W., Freudiger, C. W., Lu, S. & Xie, X. S. Coherent nonlinear optical imaging: beyond fluorescence microscopy. Annu. Rev. Phys. Chem. 62, 507-530 (2011).

101. Saar, B. G. et al. Video-rate molecular imaging in vivo with stimulated Raman scattering. Science 330, 1368-1370 (2010).

102. Ji, M. et al. Rapid, label-free detection of brain tumors with stimulated Raman scattering microscopy. Sci. Transl. Med. 5, 201ra119 (2013).

103. Wei, L. et al. Live-cell imaging of alkyne-tagged small biomolecules by stimulated Raman scattering. Nat. Methods 11, 410-2 (2014).

104. Yamakoshi, H. et al. Alkyne-tag Raman imaging for visualization of mobile small molecules in live cells. J. Am. Chem. Soc. 134, 20681-20689 (2012).

105. Results, E. Probe-frequency dependence of the resonant Inverse Raman band shape. October 89, 3945-3950 (1988).

106. McCamant, D. W., Kukura, P. & Mathies, R. A. Femtosecond Broadband Stimulated Raman: A New Approach for High-Performance Vibrational Spectroscopy. Appl. Spectrosc. 57, 1317-1323 (2003).

107. Kim, H. M., Kim, H., Yang, I., Jin, S. M. & Suh, Y. D. Time-gated pre-resonant femtosecond stimulated Raman spectroscopy of diethylthiatricarbocyanine iodide. Phys. Chem. Chem. Phys. 16, 5312-8 (2014).

108. Asher, S. A. UV resonance Raman studies of molecular structure and dynamics: applications in physical and biophysical chemistry. Annu. Rev. Phys. Chem. 39, 537-588 (1988).

What is claimed is:

1. A bond-edited compound comprising a vibrational tag, wherein the bond-edited compound exhibits at least one Raman peak in a region of 1800 cm$^{-1}$ to 2800 cm$^{-1}$, wherein the vibrational tag comprises at least one $^{13}$C atom, and wherein the bond-edited compound comprises a bond-edited dye that is conjugated to a biological molecule.

2. The bond-edited compound according to claim 1, wherein the vibrational tag further comprises —C≡$^{15}$N—.

3. The bond-edited compound according to claim 1, wherein the vibrational tag comprises —C≡$^{13}$C—, —$^{13}$C≡$^{3}$C—, or $^{13}$C≡N.

4. The bond-edited compound according to claim 1, wherein the vibrational tag comprises $^{13}$C≡$^{15}$N—.

5. A label, comprising:
   at least one bond-edited compound that is a dye comprising a vibrational tag, wherein the bond-edited compound exhibits at least one Raman peak in a region of 1800 cm$^{-1}$ to 2800 cm$^{-1}$, wherein the vibrational tag comprises —C≡$^{15}$N— or —$^{13}$C≡$^{15}$N—, and wherein the bond-edited compound comprises a bond-edited dye that is conjugated to a biological molecule.

6. The label of claim 5, wherein the at least one bond-edited compound further comprises at least one isotopically modified alkyne.

7. The label of claim 5, further comprising at least one chemical.

8. The label of claim 5, wherein the dye has a light absorption peak that is between 350 nm and 543 nm.

9. The label of claim 5, wherein the dye has a light absorption peak that is between 650 nm and 740 nm.

10. The label of claim 5, wherein the dye has a light absorption peak that is between 740 nm and 895 nm.

11. A label, comprising:
    at least one bond-edited compound that is a dye comprising a vibrational tag, wherein the bond-edited compound exhibits at least one Raman peak in a region of 1800 cm$^{-1}$ to 2800 cm$^{-1}$, wherein the label further comprises at least one light absorbing protein.

12. A label, comprising:
    at least one bond-edited compound that is a dye comprising a vibrational tag,
    wherein the bond-edited compound exhibits at least one Raman peak in a region of 1800 cm$^{-1}$ to 2800 cm$^{-1}$,
    wherein the vibrational tag comprises —C≡$^{15}$N— or —$^{13}$C≡$^{15}$N—, and
    wherein the dye has a light absorption peak that is between 350 nm and 543 nm.

13. A label, comprising:
    at least one bond-edited compound that is a dye comprising a vibrational tag,
    wherein the bond-edited compound exhibits at least one Raman peak in a region of 1800 cm-1 to 2800 cm-1,
    wherein the vibrational tag comprises —C≡$^{15}$N— or —$^{13}$C≡$^{15}$N—, and
    wherein the dye has a light absorption peak that is between 740 nm and 895 nm.

* * * * *